United States Patent
Wang et al.

(10) Patent No.: US 11,248,231 B2
(45) Date of Patent: Feb. 15, 2022

(54) COMPOSITIONS, METHODS AND SYSTEMS FOR IDENTIFYING CANDIDATE NUCLEIC ACID AGENT

(71) Applicant: Aptitude Medical Systems, Inc., Santa Barbara, CA (US)

(72) Inventors: Jinpeng Wang, Santa Barbara, CA (US); Qin Yang, Santa Barbara, CA (US); Qiang Gong, Santa Barbara, CA (US)

(73) Assignee: Aptitude Medical Systems, Inc., Santa Barbara, CA (US)

( * ) Notice: Subject to any disclaimer, the term of this patent is extended or adjusted under 35 U.S.C. 154(b) by 397 days.

(21) Appl. No.: 16/334,057

(22) PCT Filed: Sep. 27, 2017

(86) PCT No.: PCT/US2017/053578
§ 371 (c)(1),
(2) Date: Mar. 18, 2019

(87) PCT Pub. No.: WO2018/064086
PCT Pub. Date: Apr. 5, 2018

(65) Prior Publication Data
US 2019/0211335 A1    Jul. 11, 2019

Related U.S. Application Data

(60) Provisional application No. 62/401,559, filed on Sep. 29, 2016.

(51) Int. Cl.
*C12N 15/115* (2010.01)
*C40B 10/00* (2006.01)
*C12N 15/10* (2006.01)
*C12Q 1/6811* (2018.01)
(Continued)

(52) U.S. Cl.
CPC ............ *C12N 15/115* (2013.01); *C12N 15/10* (2013.01); *C12N 15/1093* (2013.01);
(Continued)

(58) Field of Classification Search
None
See application file for complete search history.

(56) References Cited

U.S. PATENT DOCUMENTS

| 5,756,291 | A | 5/1998 | Griffin et al. |
| 2006/0121489 | A1 | 6/2006 | Gorenstein et al. |

(Continued)

FOREIGN PATENT DOCUMENTS

WO    WO-2014088830 A2 *    6/2014    ........... C12N 15/115

OTHER PUBLICATIONS

Blind et al. "Aptamer Selection Technology and Recent Advances", Molecular Therapy Nucleic Acids, Dec. 31, 2015(Dec. 31, 2015), vol. 4, pp. 1-7.

(Continued)

*Primary Examiner* — Kaijiang Zhang
(74) *Attorney, Agent, or Firm* — IPro, PLLC

(57) ABSTRACT

The present disclosure provides compositions, methods and systems for generating nucleic acid agents having a desired property, such as a property for specifically binding to a target. More specifically, the present disclosure provides compositions, methods and systems for generating a pool of modified members comprising modified nucleic acid agents with an unlimited range of chemical diversity.

21 Claims, 16 Drawing Sheets

Specification includes a Sequence Listing.

(51) Int. Cl.
*C12Q 1/6834* (2018.01)
*C40B 30/04* (2006.01)
*C40B 40/06* (2006.01)

(52) U.S. Cl.
CPC ............ *C12Q 1/6811* (2013.01); *C40B 10/00* (2013.01); *C40B 30/04* (2013.01); *C40B 40/06* (2013.01); *C12N 2310/321* (2013.01); *C12N 2310/322* (2013.01); *C12Q 1/6834* (2013.01)

(56) References Cited

U.S. PATENT DOCUMENTS

| | | |
|---|---|---|
| 2008/0200340 A1 | 8/2008 | Gorenstein et al. |
| 2009/0170718 A1 | 7/2009 | Soh et al. |
| 2010/0240544 A1 | 9/2010 | Liu et al. |
| 2016/0130575 A1 | 5/2016 | Wang et al. |

OTHER PUBLICATIONS

Kimoto et al. "Generation of High-Affinity DNA Aptamers Using an Expanded Genetic Alphabet", Nature Biotechnology, May 1, 2013(May 1, 2013), vol. 31, pp. 453-457.

J. Wang, et al. "Particle Display: A Quantitative Screening Method for Generating High-Affinity Aptamers", Angewandte Chemie International Edition 126 (19), 4896-4901 (2014).

Q. Gong, et al. "Selection Strategy to Generate Aptamer Pairs that Bind to Distinct Sites on Protein Target", Analytical Chemistry 84 (12), 5365-5371 (2012).

J. Wang, et al. "Influence of Target Concentration and Background Binding on In Vitro Selection of Affinity Reagents", PLoS One 7 (8), e43940 (2012).

H. Qu, et al. "Rapid and label-free strategy to select aptamers for metal ions", ACS Nano 10 (8), 7558-7565 (2016).

* cited by examiner

SEQUENCE LISTING

```
<160> NUMBER OF SEQ ID NOS: 3

<210> SEQ ID NO 1
<211> LENGTH: 81
<212> TYPE: DNA
<213> ORGANISM: Artificial Sequence
<220> FEATURE:
<223> OTHER INFORMATION: 40-nt randomized sequence
<220> FEATURE:
<221> NAME/KEY: misc_feature
<222> LOCATION: (24)..(63)
<223> OTHER INFORMATION: n is a, c, g, or t

<400> SEQUENCE: 1
atccagagtg acgctcttca gcannnnnnn nnnnnnnnnn nnnnnnnnnn nnnnnnnnnn      60
nnntgcacac cgtcgcttag t                                                81

<210> SEQ ID NO 2
<211> LENGTH: 23
<212> TYPE: DNA
<213> ORGANISM: Artificial Sequence
<220> FEATURE:
<223> OTHER INFORMATION: modified FP

<400> SEQUENCE: 2
atccagagtg acgctcttca gca                                              23

<210> SEQ ID NO 3
<211> LENGTH: 86
<212> TYPE: DNA
<213> ORGANISM: Artificial Sequence
<220> FEATURE:
<223> OTHER INFORMATION: 40-nt randomized sequence
<220> FEATURE:
<221> NAME/KEY: misc_feature
<222> LOCATION: (27)..(66)
<223> OTHER INFORMATION: n is a, c, g, or t

<400> SEQUENCE: 3
catatgagca gcacagaggt cagatgnnnn nnnnnnnnnn nnnnnnnnnn nnnnnnnnnn      60
nnnnnnccta tgcgtgctac cgtgaa                                           86
```

COMPOSITIONS, METHODS AND SYSTEMS FOR IDENTIFYING CANDIDATE NUCLEIC ACID AGENT

CROSS-REFERENCE TO RELATED APPLICATION

This application claims the benefit of U.S. Provisional Application No. 62/401,559, filed Sep. 29, 2016.

BACKGROUND

Since their initial description, aptamers have shown considerable promise as a synthetic alternative to monoclonal antibodies. They possess numerous important advantages, including thermo stability, ease of chemical synthesis and modification, and the capacity for reversible folding, all of which are valuable characteristics for diverse applications in molecular diagnostics and therapeutics.

Unfortunately, the standard aptamer generation process (i.e., Systematic Evolution of Ligands by Exponential Enrichment (SELEX)) often fails to yield aptamers with comparable affinity and specificity relative to antibodies. Furthermore, it has been postulated that aptamers based entirely on natural nucleotides without chemical modifications only offer a limited repertoire of chemical interactions and are capable of targeting only about 30% of the human proteome. In addition, since natural nucleotides are susceptible to nuclease degradation, it will limit the in vivo half-life of the aptamers.

Thus, there is a need to incorporate modified nucleotides into the discovery process, for example, by generating libraries or pools of substantially modified or even fully modified aptamers.

However, incorporating modified nucleotides into aptamer discovery can be extremely challenging technically. For example, a typical round of an aptamer discovery process may comprise 3 steps: 1) exposing the starting library comprising numerous random nucleotide sequences to a target of interest; 2) selecting the nucleotide sequences exhibiting high affinity to the target; and 3) amplifying the selected sequences, e.g., by PCR or RT-PCR. The pool of amplified sequences from step 3 can then be used in step 1 again for the next round of selection.

There are numerous challenges when modified nucleotides are involved in the typical aptamer discovery process. For example, most of the time, nucleic acid agents comprising modified nucleotides either cannot function as a template for existing polymerases, and thus cannot be enzymatically amplified by PCR or RT-PCR, or can only be amplified with low efficiency and/or high bias.

Although chemical synthesis may be used to produce a library comprising numerous different modified nucleic acid agents, it is extremely laborious and expensive to generate and preserve them in a clonal manner (i.e. with multiple copies of the same modified nucleic acid agent clustered together in a solution) in a pool or a library that can be used for further screening, especially when the number of different nucleic acid agents in the pool is huge. Moreover, even when such an initial library can be prepared, after screening, the selected modified nucleic acid agents cannot be amplified to generate an enrich pool for a further round of screening. Because iterative screening is desired for the development of high performance aptamers, this challenge critically limits the practical range of modified nucleotides for aptamer discovery.

These challenges have hindered widespread adoption of aptamers, and there is a critical need for methods that can consistently generate aptamers with superior affinity and specificity against a wider range of targets.

SUMMARY OF THE INVENTION

The present disclosure provides compositions, methods and systems for generating nucleic acid agents having a desired property, e.g., a property of specifically binding to a target (such as a protein target). More specifically, the present disclosure provides compositions, methods and systems for generating a pool of modified nucleic acid agents with an unlimited range of chemical diversity.

The compositions, methods and systems provided in the present application enable simultaneous generation of numerous different modified nucleic acid agents (e.g., aptamers) in a clonal manner, thereby providing a pool or a library of modified nucleic acid agents in a cost-effective way. In some embodiments, the compositions, methods and systems of the present application also enable identification and/or further amplification of any modified nucleic acid agent in the pool, thereby providing enriched pools that can be used in further screening.

In one aspect, the present disclosure provides a particle comprising a plurality of nucleic acid agents immobilized thereto. The plurality of nucleic acid agents may comprise a first population (e.g., candidate nucleic acid agents) and a second population (e.g., identification nucleic acid agents); nucleic acid agents in the first population may be different from that in the second population. The first population may comprise a plurality of identical copies of a single species of candidate nucleic acid agent. The second population may comprise at least one nucleic acid agent, and the at least one nucleic acid agent may enable amplification of nucleic acid agents comprising the same nucleic acid sequence as the candidate nucleic acid agent comprised in the first population.

The at least one nucleic acid agent comprised in the second population (e.g., identification nucleic acid agent) may contain nucleic acid sequence information of the candidate nucleic acid agent in the first population. In some embodiments, the at least one nucleic acid agent comprised in the second population is a unique identifier for the candidate nucleic acid agent comprised in the first population.

In some embodiments, the at least one nucleic acid agent comprised in the second population comprises at least one identification nucleic acid agent. For example, the nucleic acid agent comprised in the second population may be the identification nucleic acid agent.

In some embodiments, the single species of candidate nucleic acid agent comprised in the first population is capable of specifically binding to a target. For example, the target may be a protein target. For example, the single species of candidate nucleic acid agent comprised in the first population may be an aptamer.

In some embodiments, each of the candidate nucleic acid agent comprised in the first population comprises at least one modification. In some embodiments, said at least one modification comprises at least one modified nucleotide (e.g., a modified nucleic acid agent).

In some embodiments, each of the candidate nucleic acid agent comprised in the first population consists essentially of modified nucleotides.

In some embodiments, none of the candidate nucleic acid agent comprised in the first population is capable of functioning directly as a template in a nucleic acid amplification reaction. For example, each of the candidate nucleic acid agent comprised in the first population may comprise at least one modified nucleotide (e.g., a modified nucleic acid agent) and may not be capable of functioning directly as a template in a nucleic acid amplification reaction.

The modified nucleotide may comprise a chemical substitution or modification at one or more positions independently selected from the group consisting of a ribose position, a deoxyribose position, a phosphate position, and a base position. For example, the modified nucleotide may comprise one or more chemical modifications at one or more positions independently selected from the group consisting of a ribose position, a deoxyribose position, a phosphate position, and a base position.

For example, the modified nucleotide may comprise one or more modifications independently selected from the group consisting of a 2'-position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, a methylation, a 3' cap, and a 5' cap.

The 5-position modified pyrimidine may be independently selected from the group consisting of 5-Carboxy-2'-deoxyuridine, 5-Aminoallyl-2'-deoxyuridine, 5-[(3-Indolyl)propionamide-N-allyl]-2'-deoxyuridine, 5-Carboxy-2'-deoxycytidine, 5-Aminoallyl-2'-deoxycytidine, Biotin-16-Aminoallyl-2'-deoxycytidine, 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

The at least one nucleic acid agent comprised in the second population (e.g., the identification nucleic acid agent) may be capable of being amplified in a nucleic acid amplification reaction and/or being sequenced. The second population may comprise a plurality of identical copies of the at least one nucleic acid agent (e.g., identification nucleic acid agent).

In some embodiments, the at least one nucleic acid agent comprised in the second population (e.g., identification nucleic acid agent) comprises the same nucleic acid sequence as that of the nucleic acid agent in the first population (e.g., candidate nucleic acid agent).

In some embodiments, the at least one nucleic acid agent comprised in the second population (e.g., the identification nucleic acid agent) is the same as the candidate nucleic acid agent in the first population, except that the at least one nucleic acid agent comprised in the second population does not comprise any modification (e.g., a modified nucleotide) while the candidate nucleic acid agent in the first population comprises at least one modification (e.g., a modified nucleotide).

The at least one nucleic acid agent comprised in the second population (e.g., the identification nucleic acid agent) may consist essentially of natural nucleotides. In some embodiments, the at least one nucleic acid agent comprised in the second population (e.g., the identification nucleic acid agent) consists of natural DNA.

A ratio of candidate nucleic acid agents comprised in the first population to that comprised in the second population (e.g., the identification nucleic acid agent) may be from about $10^{10}$:1 to about 1:1.

One or more of the nucleic acid agents (e.g., candidate nucleic acid agent and/or identification nucleic acid agent) immobilized to the particle may comprise a molecule conjugated thereto. The molecule may be selected from the group consisting of a small molecule, a fluorophore, a peptide, a therapeutically active component and a siRNA.

The particle may be non-magnetic, magnetic or paramagnetic. The particle may have at least one dimension of from about 50 nm to about 100 µm.

The plurality of nucleic acid agents immobilized to the particle may comprise from about 10 to about $10^{10}$ nucleic acid agents.

The nucleic acid agent comprised in the first population may be capable of specifically binding to a target with a $K_d$ of from about 1 pM to about 100 µM.

The nucleic acid agents immobilized to the particle may comprise single-stranded nucleic acid agents, double-stranded nucleic acid agents, or a combination thereof.

In another aspect, the present disclosure provides a particle library, wherein the library may comprise from about 10 to about $10^{15}$ different particles of the present disclosure. In some embodiments, the library is an enriched particle pool.

In some embodiments, for any particle comprised in the particle library, a nucleic acid sequence of the nucleic acid agents immobilized thereto is different from that of the nucleic acid agents immobilized to at least one other particle in the library. In some embodiments, sequence diversity of the nucleic acid agents immobilized to any particle in the library is less than that of the total nucleic acid agents comprised by all the particles in the library.

In one aspect, the present disclosure provides a method for identifying a nucleic acid agent having a desired property from a mixture of candidate nucleic acid agents. The method may comprise: a) obtaining one or more particles of the present disclosure or a library of particles of the present disclosure; b) exposing the particles to a target, thereby determining a presence or absence of the desired property; c) isolating one or more particles having immobilized thereto a nucleic acid agent having the desired property; and d) identifying the nucleic acid agent having the desired property from the isolated particles.

In the method, the target may be a protein target, a small molecule target, a whole cell, a cellular component or a liposome. The desired property may be a target binding activity or a target-binding induced activity. The target binding activity may be affinity, specificity or bi-specificity. The target-binding induced activity may be a catalytic activity, an inhibition activity, an activation activity, a structure switching activity, and/or a cooperative activity. The desired property may be a property of the nucleic acid agent of the first population. An identity of the nucleic acid agent having the desired property may be determined from the at least one nucleic acid agent comprised in the second population. For example, an identity of the nucleic acid agent having the desired property (e.g., the modified nucleic acid agent, such as an aptamer comprising one or more modified nucleotide) may be determined through sequencing the at least one nucleic acid agent comprised in the second population (e.g., the identification nucleic acid agent, such as a corresponding DNA molecule consisting of natural nucleotides).

In one aspect, the present disclosure provides a method for generating a particle of the present disclosure or a library of particles of the present disclosure.

In one aspect, the present disclosure provides a method for generating one or more modified particles with nucleic acid agents immobilized thereto, such as the particles or the library of particles of the present disclosure. The method may comprise: a) obtaining one or more template particles, each with a plurality of double-stranded nucleic acid agents immobilized thereto, each of the double-stranded nucleic acid agent may comprise a forward strand and a reverse strand. For each particle, the plurality of double-stranded nucleic acid agents may comprise a first double-stranded population (e.g., double-stranded candidate nucleic acid agent) and a second double-stranded population (e.g., double-stranded identification nucleic acid agent), the nucleic acid agents comprised in the first double-stranded population may be different from that in the second double-stranded population. The method may further comprise b) treating the template particle obtained in a) to obtain a modified particle, wherein each modified particle may comprise at least one modified candidate nucleic acid agent derived from the first double-stranded population (e.g., double-stranded candidate nucleic acid agents) and at least one identification nucleic acid agent derived from the second double-stranded population (e.g., double-stranded identification nucleic acid agent); the at least one modified nucleic acid agent (e.g., modified candidate nucleic acid agent) may contain at least one modified nucleotide and is not capable of functioning directly as a template in a nucleic acid amplification reaction; and the at least one identification nucleic acid agent may enable amplification of nucleic acid agents comprising the same nucleic acid sequence as the modified nucleic acid agent derived from the first double-stranded population.

The method may further comprise c) amplifying the at least one identification nucleic acid agent to generate one or more of the template particles of a).

In some embodiments, the one or more template particles comprise two or more particles, and for any one of the two or more particles, a nucleic acid sequence of the nucleic acid agents immobilized thereto is different from that of the nucleic acid agents immobilized to at least one other particle.

In some embodiments of the method for generating one or more modified particles, in b), treating the template particle comprises: b1) treating the template particle obtained in a) so that only the reverse strand of the nucleic acid agent comprised in the second double-stranded population (e.g., the double-stranded identification nucleic acid agents) is removed. For example, b1) may comprise treating the template particle obtained in a) with a 5' to 3' exonuclease to remove only the reverse strand of the nucleic acid agent comprised in the second double-stranded population (e.g., the double-stranded identification nucleic acid agents).

In some embodiments of the method for generating one or more modified particles, in b), treating the template particle further comprises b2) treating the particle obtained in b1) so that a substantial part of the forward strand of said nucleic acid agents in said first double-stranded population is removed (e.g., providing a partially double-stranded candidate nucleic acid agent). In some embodiments, the particle obtained in b1) may be treated with a site-specific nicking enzyme to generate nicked forward strand of nucleic acid agents comprised in said first double-stranded population (e.g., double-stranded candidate nucleic acid agents), and then further treated with an exonuclease to remove a substantial part of the forward strand of the nucleic acid agents in the first double-stranded population (e.g., thereby generating partially double-stranded candidate nucleic acid agents). In some embodiments, the particle obtained in b1) may be treated with a site-specific restriction enzyme to generate double-stranded break of nucleic acid agents comprised in the first double-stranded population (e.g., double-stranded candidate nucleic acid agents), and then further treated with an exonuclease to remove a substantial part of the forward strand of the nucleic acid agents in the first double-stranded population (e.g., thereby generating partially double-stranded candidate nucleic acid agents).

In some embodiments of the method for generating one or more modified particles, b) further comprises b3) incorporating nucleotides to generate nucleic acid strand complementary to the reverse strand of said nucleic acid agents of the first double-stranded population (e.g., reverse strand of the double-stranded candidate nucleic acid agent). For example, the nucleotides may be incorporated with a nucleic acid polymerase.

In some embodiments of the method for generating one or more modified particles, b) further comprises b4) generating a modified particle with a plurality of single-stranded nucleic acid agents immobilized thereto, the plurality of single-stranded nucleic acid agents comprise a first single-stranded population (e.g., modified candidate nucleic acid agents) and a second single-stranded population (e.g., identification nucleic acid agents); the at least one modified nucleic acid agent is comprised in the first single-stranded population and the at least one identification nucleic acid agent is comprised in the second single-stranded population.

In some embodiments of the method, the at least one modified nucleic acid agent (e.g., modified candidate nucleic acid agent) is an aptamer.

In some embodiments, the method for generating one or more modified particle comprises: a) obtaining one or more template particles, each with a plurality of double-stranded nucleic acid agents immobilized thereto, wherein the plurality of double-stranded nucleic acid agents comprises a first double-stranded population (e.g., double-stranded candidate nucleic acid agents) and a second double-stranded population (e.g., double-stranded identification nucleic acid agents). The first double-stranded population may comprise a plurality of identical copies of a single species of double-stranded candidate nucleic acid agent; the second double-stranded population may comprise at least one nucleic acid agent (e.g., double-stranded candidate nucleic acid agent), and the at least one nucleic acid agent may enable amplification of nucleic acid agents comprising the same nucleic acid sequence as the nucleic acid agent comprised in the first double-stranded population; the nucleic acid agents comprised in the first double-stranded population may be different from that in the second double-stranded population; each of the double-stranded nucleic acid agents may comprise a forward strand and a reverse strand complementary to the forward strand, and the forward strand may be attached to the particle. In some embodiments, the at least one nucleic acid agent comprised in the second double-stranded population contains nucleic acid sequence information of the nucleic acid agent in the first double-stranded population.

The method for generating one or more modified particle may further comprise b) treating the template particle obtained in a) to obtain a modified particle, wherein each modified particle comprises at least one modified nucleic acid agent (e.g., modified candidate nucleic acid agent) derived from the first double-stranded population (e.g., double-stranded candidate nucleic acid agent) and at least one identification nucleic acid agent derived from the second double-stranded population (e.g., double-stranded candidate nucleic acid agent); the at least one modified nucleic acid agent may contain at least one modified nucleotide and is not capable of functioning directly as a template in a nucleic acid amplification reaction; and the at least one identification nucleic acid agent may enable amplification of nucleic acid agents comprising the same nucleic acid sequence as the modified nucleic acid agent derived from the first double-stranded population.

In a method for generating one or more modified particle, as described in the present disclosure, b) may comprise b1) treating the particle obtained in a) so that only the reverse strand of the at least one nucleic acid agent comprised in the second double-stranded population (e.g., the double-stranded identification nucleic acid agents) is removed. For example, the reverse strand of the nucleic acid agents comprised in the first double-stranded population (e.g., the double-stranded candidate nucleic acid agents) may be resistant to 5' to 3' exonuclease digestion. In some embodiments, a 5'end of the reverse strand of the nucleic acid agents in the first double-stranded population is phosphorothioated. The reverse strand of the at least one nucleic acid agent comprised in the second double-stranded population (e.g., the double-stranded candidate nucleic acid agents) may be susceptible to 5' to 3' exonuclease digestion. In some embodiments, b1) comprises treating the particle obtained in a) with a 5' to 3' exonuclease thereby only removing the reverse strand of the at least one nucleic acid agent comprised in the second double-stranded population.

In a method for generating one or more modified particle, as described in the present disclosure, b) may further comprise b2) treating the particle obtained in b1) so that a substantial part of the forward strand of the nucleic acid agents of the first double-stranded population (e.g., double-stranded candidate nucleic acid agent) is removed and the reverse strand of the nucleic acid agents of the first double-stranded population is hybridized to a partial complement thereof attached to the particle. In b2) of the method, the forward strand of the at least one nucleic acid agent of the second double-stranded population may remain intact and attached to the particle.

In some embodiments, b2) comprises treating the particle obtained in b1) with a site-specific nicking enzyme to generate nicked forward strand of nucleic acid agents comprised in the first double-stranded population. In some embodiments, b2) comprises treating the particle obtained in b1) with a site-specific restriction enzyme to generate double-stranded break of nucleic acid agents comprised in the first double-stranded population. b2) may further comprise removing a substantial part of the forward strand of the nucleic acid agents in the first double-stranded population with an exonuclease. In some embodiments, in b2), a remaining part of the forward strand of the nucleic acid agents in the first double-stranded population (e.g., double-stranded candidate nucleic acid agents) is not removed and remains attached to the particle, serving as the partial complement, and the reverse strand of the nucleic acid agents in the first double-stranded population remains hybridized to the remaining part of the forward strand of the nucleic acid agents in the first double-stranded population.

In some embodiments of the method for generating the modified particles, the template particle in a) further comprises a third population containing a plurality of single-stranded nucleic acid agents attached thereto (e.g., single-stranded forward primers), the plurality of single-stranded nucleic acid agents of the third population serve as the partial complement in b2) and hybridize to the reverse strand of the nucleic acid agents of the first double-stranded population subsequent to removal of a substantial part of the forward strand of nucleic acid agents in the first double-stranded population.

In a method for generating the modified particles, as described in the present disclosure, b) may further comprise b3) extending the partial complement on the particle of b2) by incorporating nucleotides to generate nucleic acid strand complementary to the reverse strand of the nucleic acid agents of the first double-stranded population, wherein the incorporated nucleotides may comprise at least one modified nucleotide. For example, b3) may comprise incorporating nucleotides with a nucleic acid polymerase.

In a method for generating the modified particles, as described in the present disclosure, b) may further comprise b4) removing the reverse strand of all the nucleic acid agents attached to the particle obtained in b3), thereby generating a modified particle with a plurality of single-stranded nucleic acid agents immobilized thereto. For example, b4) may comprise de-hybridizing the reverse strand by incubation with an alkaline solution (such as a solution of NaOH).

The plurality of single-stranded nucleic acid agents immobilized to the modified particle generated in b4) may comprise a first single-stranded population (e.g., modified candidate nucleic acid agent) and a second single-stranded population (e.g., identification nucleic acid agent). The first single-stranded population may comprise a plurality of identical copies of single-stranded nucleic acid agents (e.g., the modified candidate nucleic acid agent), each of which may be complementary to the reverse strand of the nucleic acid agents in the first double-stranded population (e.g., double-stranded candidate nucleic acid agent) of the template particle and may comprise at least one modified nucleotide. The second single-stranded population may comprise at least one single-stranded nucleic acid agent (e.g., the identification nucleic acid agent), which may be identical to the forward strand of the at least one nucleic acid agent comprised in the second double-stranded population (e.g., double-stranded identification nucleic acid agent) of the template particle and may enable amplification of nucleic acid agents comprising the same nucleic acid sequence as the nucleic acid agent comprised in the first single-stranded population.

In the method for generating one or more modified particle, subsequent to b1), the particle may be encapsulated in a compartment with reagents necessary for performing at least b2). The reagents necessary for performing at least b2) may comprise one of more of the following: a nicking enzyme, a site-specific restriction enzyme, an exonuclease, a polymerase, and modified dNTPs.

In the modified particle generated in b4), the nucleic acid agents of the first single-stranded population (e.g., the modified candidate nucleic acid agents) may be capable of specifically binding to a target. The target may be a protein target. The at least one nucleic acid agent comprised in the second single-stranded population (e.g., the identification nucleic acid agent) may contain nucleic acid sequence information of the nucleic acid agent comprised in the first single-stranded population. The nucleic acid agents of the first single-stranded population (e.g., the modified candidate nucleic acid agents) may not be capable of functioning directly as a template in a nucleic acid amplification reaction.

The at least one nucleic acid agent comprised in the second single-stranded population (e.g., the identification nucleic acid agent) may be a unique identifier for the nucleic acid agent comprised in the first single-stranded population (e.g., the modified candidate nucleic acid agent).

The modified candidate nucleic acid agent (e.g., the nucleic acid agent comprised in the first single-stranded population) may be an aptamer.

In some embodiments, the modified candidate nucleic acid agent (e.g., the nucleic acid agent comprised in the first single-stranded population) consists essentially of modified nucleotides.

The modified candidate nucleotide may comprise one or more chemical modifications at one or more positions independently selected from the group consisting of a ribose position, a deoxyribose position, a phosphate position, and a base position. For example, the chemical modifications are independently selected from the group consisting of a 2'position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, methylation, a 3'cap, and a 5' cap. The 5-position modified pyrimidine may be selected from the group consisting of 5-Carboxy-2'-deoxyuridine (5-Carboxy-dU), 5-Aminoallyl-2'-deoxyuridine (5-AA-dU), 5-[(3-Indolyl)propionamide-N-allyl]-2'-deoxyuridine (Tryptamino-dU), 5-Carboxy-2'-deoxycytidine (5-Carboxy-dC), 5-Aminoallyl-2'-deoxycytidine (5-AA-dC), Biotin-16-Aminoallyl-2'-deoxycytidine (Biotin-16-AA-dC), 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

The identification nucleic acid agent (e.g., the at least one single-stranded nucleic acid agent of the second single-stranded population, or the at least one double-stranded nucleic acid agent of the second double-stranded population) may be capable of being amplified in a nucleic acid amplification reaction and/or being sequenced.

In the method for generating one or more modified particle, the second double-stranded population may comprise a plurality of identical copies of the at least one nucleic acid agent.

The at least one nucleic acid agent comprised in the second double-stranded population (e.g., double-stranded identification nucleic acid agent) may comprise the same nucleic acid sequence as that comprised in the nucleic acid agent of the first double-stranded population (e.g., double-stranded candidate nucleic acid agent).

The identification nucleic acid agent (e.g., the at least one single-stranded nucleic acid agent of the second single-stranded population) may comprise the same nucleic acid sequence as that comprised in the modified candidate nucleic acid agent (i.e., the nucleic acid agent of the first single-stranded population). For example, the identification nucleic acid agent (e.g., the at least one nucleic acid agent comprised in the second single-stranded population) may be the same as the modified candidate nucleic acid agent (e.g., the nucleic acid agent of the first single-stranded population), except that the identification nucleic acid agent does not comprise any modified nucleotide while the modified candidate nucleic acid agent comprises at least one modified nucleotide.

The identification nucleic acid agent (e.g., the at least one single-stranded nucleic acid agent of the second single-stranded population) may consist essentially of natural nucleotides. For example, the identification nucleic acid agent (e.g., the at least one single-stranded nucleic acid agent of the second single-stranded population) may consist of natural DNA.

In the method for generating one or more modified particle, a ratio of nucleic acid agents comprised in the first double-stranded population (e.g., double-stranded candidate nucleic acid agents) to that comprised in the second double-stranded population (e.g., double-stranded identification nucleic acid agents) may be from about $10^{10}:1$ to about 1:1.

In the method, one or more of the double-stranded and/or single-stranded nucleic acid agents immobilized to the particle may comprise a molecule conjugated thereto. The molecule may be selected from the group consisting of a small molecule, a fluorophore, a peptide, a therapeutically active component and an siRNA.

In the method, the particle may be non-magnetic, magnetic or paramagnetic. In some embodiments, the particle has at least one dimension of from about 50 nm to about 100 μm.

In the method, the plurality of double-stranded and/or single-stranded nucleic acid agents immobilized to the particle may comprise from about 10 to about $10^{10}$ nucleic acid agents.

In the method, the modified candidate nucleic acid agent (e.g., the single-stranded nucleic acid agent in the first single-stranded population) of the modified particle may be capable of specifically binding to a target with a $K_d$ of from about 1 pM to about 100 μM.

The method may further comprise immobilizing a plurality of double-stranded nucleic acid agents to the particle prior to a). The immobilizing may comprise using emulsion PCR.

The method may further comprise, prior to a), treating one or more particles with a plurality of identical double-stranded nucleic acid agents immobilized thereto to generate the template particles comprising the first and the second double-stranded populations.

In one aspect, the present disclosure provides use of a particle of the present disclosure or a pool/library of particles of the present disclosure in the manufacture of a reagent for identifying a nucleic acid agent having a desired property.

In one aspect, the present disclosure provides a method for generating a pool comprising a plurality of modified members (e.g., particles). The method may comprise: a) providing a pool comprising a plurality of kernel members (e.g., kernel particles), with each kernel member comprising a plurality of partially double-stranded candidate nucleic acid agents immobilized to a solid support, and each of the partially double-stranded candidate nucleic acid agents comprises a forward strand and a reverse strand longer than the forward strand, wherein the forward and reverse strand associate with each other at least partially via base-paring; and b) extending the forward strand of the partially double-stranded candidate nucleic acid agents by nucleotide polymerization using the corresponding reverse strand as a template, and at least one modified nucleotide is incorporated into the forward strand during extension to form modified candidate nucleic acid agents, thereby obtaining a pool of a plurality of modified members, with each modified member comprising a plurality of the modified candidate nucleic acid agents immobilized to the solid support; wherein a nucleic acid sequence of the candidate nucleic acid agents comprised by any kernel member is different from that of the candidate nucleic acid agents comprised by at least one other kernel member in the pool.

In some embodiments, sequence diversity of the candidate nucleic acid agents comprised by any kernel member in the pool is less than that of the total candidate nucleic acid agents comprised by all the kernel members in the pool.

In some embodiments, any one of the kernel members in the pool comprises at least $1 \times 10^2$ copies of candidate nucleic acid agents having the same nucleic acid sequence.

In some embodiments, sequence diversity of the candidate nucleic acid agents comprised by any kernel member in the pool is from 1 to 1000.

In some embodiments, a 5' end of the forward strand of the partially double-stranded candidate nucleic acid agents is attached directly or indirectly to the solid support of the kernel members.

In some embodiments, the modified candidate nucleic acid agent is not capable of functioning directly as a template in a nucleic acid amplification reaction.

In some embodiments, for each modified candidate nucleic acid agent comprised by any modified member, a corresponding identification nucleic acid agent is comprised by the same modified member, wherein the identification nucleic acid agent enables amplification of its corresponding modified candidate nucleic acid agent. For example, for each unique modified candidate nucleic acid agent comprised by any modified member, one or more corresponding identification nucleic acid agent may be comprised by the same modified member, wherein the one or more identification nucleic acid agent enables amplification of its corresponding modified candidate nucleic acid agent.

In some embodiments, the identification nucleic acid agent is immobilized to the same solid support as its corresponding modified candidate nucleic acid agent.

In some embodiments, the identification nucleic acid agent contains nucleic acid sequence information of its corresponding modified candidate nucleic acid agent. For example, the identification nucleic acid agent may be capable of being amplified in a nucleic acid amplification reaction and/or being sequenced. In some embodiments, the identification nucleic acid agent comprises the same nucleic acid sequence as that of its corresponding modified candidate nucleic acid agent. For example, the identification nucleic acid agent may be the same as its corresponding modified candidate nucleic acid agent, except that the identification nucleic acid agent does not comprise any modified nucleotide while the modified candidate nucleic acid agent comprises at least one modified nucleotide.

In some embodiments, the identification nucleic acid agent consists essentially of natural nucleotides. For example, the identification nucleic acid agent may consist of natural DNA.

In some embodiments, the identification nucleic acid agent is also comprised by the kernel member employed to generate its corresponding modified candidate nucleic acid agent.

In some embodiments, the identification nucleic acid agent comprised by the modified member and/or the kernel member is single-stranded.

In some embodiments, on any modified member, a ratio of the number of a modified candidate nucleic acid agent to that of its corresponding identification nucleic acid agent is from about $10^{10}$:1 to about 1:1.

In some embodiments, the modified candidate nucleic acid agent is capable of specifically binding to a target. The target may be a protein target. For example, the modified candidate nucleic acid agent may comprise an aptamer. In some embodiments, the modified candidate nucleic acid agent is capable of specifically binding to a target with a Kd of from about 1 pM to about 100 μM.

In some embodiments, the modified candidate nucleic acid agent consists essentially of modified nucleotides.

In some embodiments, the modified nucleotide comprises a chemical substitution or modification at one or more positions independently selected from the group consisting of a ribose position, a deoxyribose position, a phosphate position, and a base position.

In some embodiments, the modified nucleotide comprises one or more modifications independently selected from the group consisting of a 2'-position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, a methylation, a 3' cap, and a 5' cap. For example, the 5-position modified pyrimidine may be selected from the group consisting of 5-Carboxy-2'-deoxyuridine, 5-Aminoallyl-2'-deoxyuridine, 5-[(3-Indolyl)propionamide-N-allyl]-2'-deoxyuridine, 5-Carboxy-2'-deoxycytidine, 5-Aminoallyl-2'-deoxycytidine, Biotin-16-Aminoallyl-2'-deoxycytidine, 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

In some embodiments, one or more of the nucleic acid agents (e.g., the candidate nucleic acid agents and/or the identification nucleic acid agents) immobilized to the solid support comprises a molecule conjugated thereto. The molecule may be selected from the group consisting of a small molecule, a fluorophore, a peptide, a therapeutically active component and an siRNA.

In some embodiments, the solid support is a particle. For example, the solid support (e.g., the particle) may be non-magnetic, magnetic or paramagnetic. In some embodiments, the solid support has at least one dimension of from about 50 nm to about 100 μm. In some embodiments, about $10^2$ to about $10^{10}$ nucleic acid agents are immobilized to any solid support.

In some embodiments of the method, providing a pool comprising a plurality of kernel members in a) comprises: a1) providing a pool comprising a plurality of template members, with each template member comprising a plurality of double-stranded candidate nucleic acid agents immobilized to the solid support, and each double-stranded candidate nucleic acid agent comprises a forward strand and a complementary reverse strand; and a2) treating the plurality of template members of a1) to remove a substantial part of the forward strand of the double-stranded candidate nucleic acid agents, with the corresponding reverse strand immobilized on the solid support, forming the reverse strand of the partially double-stranded candidate nucleic acid agents of the kernel members.

In some embodiments, sequence diversity of the double-stranded candidate nucleic acid agents comprised by any one of the template members in the pool is less than that of the total double-stranded candidate nucleic acid agents comprised by all the template members in the pool.

In some embodiments, any one of the template members in the pool comprises at least $1 \times 10^2$ copies of double-stranded candidate nucleic acid agents having the same nucleic acid sequence.

In some embodiments, sequence diversity of the double-stranded candidate nucleic acid agents comprised by any template member in the pool is from 1 to 1000.

In some embodiments, a 5' end of the forward strand of the double-stranded candidate nucleic acid agents is attached directly or indirectly to the solid support of the template members.

In some embodiments of the method, a1) comprises generating the template members comprising the plurality of double-stranded candidate nucleic acid agents using emulsion PCR.

In some embodiments, for each double-stranded candidate nucleic acid agent comprised by any template member, a corresponding double-stranded identification nucleic acid agent is comprised by the same template member, the double-stranded identification nucleic acid agent comprises a forward strand and a complementary reverse strand, and wherein the double-stranded identification nucleic acid agent is different from its corresponding double-stranded candidate nucleic acid agent while enabling amplification thereof. For, for each unique double-stranded candidate nucleic acid agent comprised by any template member, one or more corresponding double-stranded identification nucleic acid agent may be comprised by the same template member.

In some embodiments, the double-stranded identification nucleic acid agent contains nucleic acid sequence information of its corresponding double-stranded candidate nucleic acid agent. For example, the double-stranded identification nucleic acid agent may comprise the same nucleic acid sequence as its corresponding double-stranded candidate nucleic acid agent.

In some embodiments, on any template member, a ratio of the number of a double-stranded candidate nucleic acid agent to that of its corresponding double-stranded identification nucleic acid agent is from about $10^{10}$:1 to about 1:1.

In some embodiments of the method, a2) comprises: a2-1) treating the plurality of template members of a1) to remove only the reverse strand of the double-stranded identification nucleic acid agent, and the forward strand of the double-stranded identification nucleic acid agent remains immobilized on the solid support, forming the identification nucleic acid agent on the kernel member and/or the modified member.

In some embodiments of the method, a2) further comprises a2-2) treating the plurality of template members obtained in a2-1) so that a substantial part of the forward strand of the double-stranded candidate nucleic acid agents is removed, with the reverse strand of the double-stranded candidate nucleic acid agents immobilized on the solid support, forming the reverse strand of the partially double-stranded candidate nucleic acid agents of the kernel members.

In some embodiments of the method, after extending the forward strand of the partially double-stranded candidate nucleic acid agent, the reverse strands are removed, and the modified candidate nucleic acid agents comprised by the modified members are single-stranded. For example, after extending the forward strand of the partially double-stranded candidate nucleic acid agent, the reverse strands may be removed by incubation with an alkaline solution.

In some embodiments, the reverse strand of the double-stranded candidate nucleic acid agent is resistant to 5' to 3' exonuclease digestion. For example, a 5'end of the reverse strand of the double-stranded candidate nucleic acid agent may be phosphorothioated.

In some embodiments, the reverse strand of the double-stranded identification nucleic acid agent is susceptible to 5' to 3' exonuclease digestion.

In some embodiments, a2-1) comprises treating the plurality of template members of a1) with a 5' to 3' exonuclease thereby removing only the reverse strand of the double-stranded identification nucleic acid agent.

In some embodiments, a2) comprises removing a substantial part of the forward strand of the double-stranded candidate nucleic acid agents with an exonuclease.

In some embodiments, a2-2) comprises treating the plurality of template members obtained in a2-1) with a site-specific nicking enzyme to generate nicked forward strand of the double-stranded candidate nucleic acid agents.

In some embodiments, in a2), a remaining part of the forward strand of the double-stranded candidate nucleic acid agent is not removed and remains immobilized on the solid support, serving as the forward strand of the partially double-stranded candidate nucleic acid agent on the kernel members, and the reverse strand of the double-stranded candidate nucleic acid agent remains associated with the remaining part of the forward stand, serving as the reverse strand of the partially double-stranded candidate nucleic acid agent on the kernel members.

In some embodiments, a2-2) comprises treating the plurality of template members obtained in a2-1) with a site-specific restriction enzyme to generate double-stranded break of the double-stranded candidate nucleic acid agents.

In some embodiments, the template member further comprises a plurality of single-stranded forward primers immobilized on the solid support, the single-stranded forward primers are capable of associating with the reverse strand of the double-stranded candidate nucleic acid agent subsequent to removal of a substantial part of the forward strand of the double-stranded candidate nucleic acid agent.

In some embodiments of the method, b) comprises extending the forward strand of the partially double-stranded candidate nucleic acid agents with a nucleic acid polymerase.

In some embodiments, subsequent to a2-1), each member (e.g., particle) is encapsulated in a reaction compartment. The reaction compartment may further comprise one or more of the following: a nicking enzyme, a site-specific restriction enzyme, an exonuclease, a polymerase, and modified dNTPs.

In another aspect, the present application provides a pool comprising a plurality of kernel members, with each kernel member comprising a plurality of partially double-stranded candidate nucleic acid agents immobilized to a solid support, and each of the partially double-stranded candidate nucleic acid agents comprises a forward strand and a reverse strand longer than the forward strand, wherein the forward and reverse strand associate with each other at least partially via base-paring; wherein a nucleic acid sequence of the candidate nucleic acid agents comprised by any kernel member is different from that of the candidate nucleic acid agents comprised by at least one other kernel member in the pool.

In some embodiments, sequence diversity of the candidate nucleic acid agents comprised by any kernel member in the pool is less than that of the total candidate nucleic acid agents comprised by all the kernel members in the pool.

In some embodiments, any one of the kernel members in the pool comprises at least $1\times10^2$ copies of candidate nucleic acid agents having the same nucleic acid sequence.

In some embodiments, sequence diversity of the candidate nucleic acid agents comprised by any kernel member in the pool is from 1 to 1000.

In some embodiments, a 5' end of the forward strand of the partially double-stranded candidate nucleic acid agents is attached directly or indirectly to the solid support.

In some embodiments, for each partially double-stranded candidate nucleic acid agents comprised by any kernel member, a corresponding identification nucleic acid agent is comprised by the same kernel member, wherein the identification nucleic acid agent enables amplification of its corresponding candidate nucleic acid agent. The identification nucleic acid agent may be immobilized to the same solid support as its corresponding candidate nucleic acid agent. The identification nucleic acid agent may be single-stranded. The identification nucleic acid agent may be capable of being amplified in a nucleic acid amplification reaction and/or being sequenced. For example, the identification nucleic acid agent may contain nucleic acid sequence information of its corresponding candidate nucleic acid agent. In some embodiments, the identification nucleic acid agent comprises the same nucleic acid sequence as that of its corresponding candidate nucleic acid agent.

In some embodiments, the identification nucleic acid agent consists essentially of natural nucleotides. For example, the identification nucleic acid agent may consist of natural DNA.

In some embodiments, on any kernel member, a ratio of the number of a candidate nucleic acid agent to that of its corresponding identification nucleic acid agent is from about $10^{10}$:1 to about 1:1.

In some embodiments, the solid support is a particle. The solid support may be non-magnetic, magnetic or paramagnetic. In some embodiments, the solid support has at least one dimension of from about 50 nm to about 100 μm. In some embodiments, about $10^2$ to about $10^{10}$ nucleic acid agents are immobilized to any solid support.

In another aspect, the present application provides a pool comprising a plurality of modified members, with each modified member comprising a plurality of modified candidate nucleic acid agents immobilized to a solid support, and each modified candidate nucleic acid agent comprises at least one modified nucleotide; wherein a nucleic acid sequence of the modified candidate nucleic acid agents comprised by any modified member is different from that of the modified candidate nucleic acid agents comprised by at least one other modified member in the pool.

In some embodiments, sequence diversity of the modified candidate nucleic acid agents comprised by any modified member in the pool is less than that of the total modified candidate nucleic acid agents comprised by all the modified members in the pool.

In some embodiments, any one of the modified members in the pool comprises at least $1 \times 10^2$ copies of modified candidate nucleic acid agents having the same nucleic acid sequence.

In some embodiments, sequence diversity of the modified candidate nucleic acid agents comprised by any modified member in the pool is from 1 to 1000.

In some embodiments, the modified candidate nucleic acid agents are single-stranded.

In some embodiments, a 5' end of the single-stranded modified candidate nucleic acid agent is attached directly or indirectly to the solid support.

In some embodiments, the modified candidate nucleic acid agent is not capable of functioning directly as a template in a nucleic acid amplification reaction.

In some embodiments, for each modified candidate nucleic acid agent comprised by any modified member, a corresponding identification nucleic acid agent is comprised by the same modified member, wherein the identification nucleic acid agent enables amplification of its corresponding modified candidate nucleic acid agent.

In some embodiments, the identification nucleic acid agent is immobilized to the same solid support as its corresponding modified candidate nucleic acid agent.

In some embodiments, the identification nucleic acid agent contains nucleic acid sequence information of its corresponding modified candidate nucleic acid agent.

In some embodiments, the identification nucleic acid agent is capable of being amplified in a nucleic acid amplification reaction and/or being sequenced.

In some embodiments, the identification nucleic acid agent comprises the same nucleic acid sequence as that of its corresponding modified candidate nucleic acid agent.

In some embodiments, the identification nucleic acid agent is the same as its corresponding modified candidate nucleic acid agent, except that the identification nucleic acid agent does not comprise any modified nucleotide while the modified candidate nucleic acid agent comprises at least one modified nucleotide. In some embodiments, the identification nucleic acid agent consists essentially of natural nucleotides. For example, the identification nucleic acid agent may consist of natural DNA. In some embodiments, the identification nucleic acid agent is single-stranded.

In some embodiments, on any modified member, a ratio of the number of a modified candidate nucleic acid agent to that of its corresponding identification nucleic acid agent is from about $10^{10}$:1 to about 1:1.

In some embodiments, the modified candidate nucleic acid agent is capable of specifically binding to a target. The target may be a protein target. For example, the modified candidate nucleic acid agent may comprise an aptamer.

In some embodiments, the modified candidate nucleic acid agent is capable of specifically binding to a target with a Kd of from about 1 pM to about 100 μM.

In some embodiments, the modified candidate nucleic acid agent consists essentially of modified nucleotides.

In some embodiments, the modified nucleotide comprises a chemical substitution or modification at one or more positions independently selected from the group consisting of a ribose position, a deoxyribose position, a phosphate position, and a base position.

In some embodiments, the modified nucleotide comprises one or more modifications independently selected from the group consisting of a 2'-position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, a methylation, a 3' cap, and a 5' cap. For example, the 5-position modified pyrimidine may be selected from the group consisting of 5-Carboxy-2'-deoxyuridine, 5-Aminoallyl-2'-deoxyuridine, 5-[(3-Indolyl)propionamide-N-allyl]-2'-deoxyuridine, 5-Carboxy-2'-deoxycytidine, 5-Aminoallyl-2'-deoxycytidine, Biotin-16-Aminoallyl-2'-deoxycytidine, 5-(N-benzylcarboxamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

In some embodiments, one or more of the modified candidate nucleic acid agents and/or identification nucleic acid agents immobilized to the solid support comprises a molecule conjugated thereto. The molecule may be selected from the group consisting of a small molecule, a fluorophore, a peptide, a therapeutically active component and an siRNA.

In some embodiments, the solid support is a particle. The solid support may be non-magnetic, magnetic or paramagnetic. In some embodiments, the solid support has at least one dimension of from about 50 nm to about 100 μm. In some embodiments, about $10^2$ to about $10^{10}$ nucleic acid agents are immobilized to any solid support.

In another aspect, the present application provides a pool comprising a plurality of template members, with each template member comprising a plurality of double-stranded candidate nucleic acid agents immobilized to a solid support, and each of the double-stranded candidate nucleic acid agents comprises a forward strand and a complementary reverse strand; wherein a nucleic acid sequence of the double-stranded candidate nucleic acid agents comprised by any template member is different from that of the double-stranded candidate nucleic acid agents comprised by at least one other template member in the pool.

In some embodiments, sequence diversity of the double-stranded candidate nucleic acid agents comprised by any template member in the pool is less than that of the total double-stranded candidate nucleic acid agents comprised by all the template members in the pool.

In some embodiments, any one of the template members in the pool comprises at least $1 \times 10^2$ copies of double-stranded candidate nucleic acid agents having the same nucleic acid sequence.

In some embodiments, sequence diversity of the double-stranded candidate nucleic acid agents comprised by any template member in the pool is from 1 to 1000.

In some embodiments, a 5' end of the forward strand of the double-stranded candidate nucleic acid agents is attached directly or indirectly to the solid support of the template members.

In some embodiments, for each double-stranded candidate nucleic acid agent comprised by any template member, a corresponding double-stranded identification nucleic acid agent is comprised by the same template member, the double-stranded identification nucleic acid agent comprises a forward strand and a complementary reverse strand, and wherein the double-stranded identification nucleic acid agent is different from its corresponding double-stranded candidate nucleic acid agent while enabling amplification thereof.

In some embodiments, the double-stranded identification nucleic acid agent is immobilized to the same solid support as its corresponding double-stranded candidate nucleic acid agent.

In some embodiments, the double-stranded identification nucleic acid agent contains nucleic acid sequence information of its corresponding double-stranded candidate nucleic acid agent.

In some embodiments, the double-stranded identification nucleic acid agent comprises the same nucleic acid sequence as its corresponding double-stranded candidate nucleic acid agent.

In some embodiments, on any template member, a ratio of the number of a double-stranded candidate nucleic acid agent to that of its corresponding double-stranded identification nucleic acid agent is from about $10^{10}$:1 to about 1:1.

In some embodiments, the reverse strand of the double-stranded candidate nucleic acid agent is resistant to 5' to 3' exonuclease digestion. For example, a 5'end of the reverse strand of the double-stranded candidate nucleic acid agent may be phosphorothioated.

In some embodiments, the reverse strand of the double-stranded identification nucleic acid agent is susceptible to 5' to 3' exonuclease digestion.

In some embodiments, the double-stranded identification nucleic acid agent consists essentially of natural nucleotides.

In some embodiments, the double-stranded identification nucleic acid agent consists of natural DNA.

In some embodiments, the solid support is a particle. The solid support may be non-magnetic, magnetic or paramagnetic.

In some embodiments, the solid support has at least one dimension of from about 50 nm to about 100 μm.

In some embodiments, about $10^2$ to about $10^{10}$ double-stranded nucleic acid agents are immobilized to any solid support.

In some embodiments, the template member further comprises a plurality of single-stranded forward primers immobilized on the solid support, the single-stranded forward primers are capable of hybridizing with the reverse strand of the double-stranded candidate nucleic acid agent at least partially via base-paring.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

DETAILED DESCRIPTION

Figure 1:
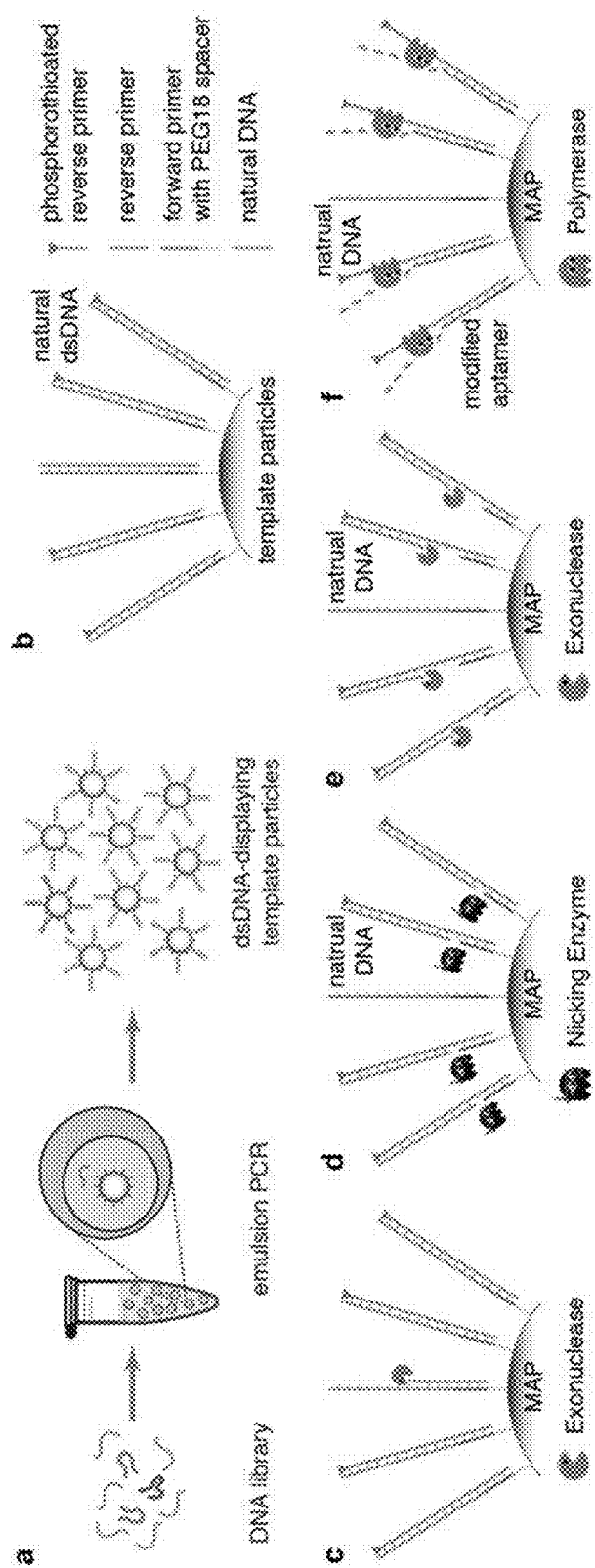
FIGS. 1a-1f illustrate an example of a process for generating a pool comprising a plurality of modified members according to the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "substantial", as used herein, generally refers to more than a minimal or insignificant amount; and "substantially" generally refers to more than minimally or insignificantly. The term "a substantial part of", as used herein, generally refers to an amount, quantity, sequence, length, concentration etc. of a part of an object that is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% of that of the entire amount, quantity, sequence, length, concentration etc. of the corresponding object.

The term "nucleic acid agent", as used herein, generally refers to a molecule comprising one or more nucleic acid subunits (e.g., nucleotide). A nucleic acid agent may include one or more subunits selected from adenosine (A), cytosine (C), guanine (G), thymine (T) and uracil (U), or analogs and variants thereof. A nucleotide can include A, C, G, T or U, or analogs and variants thereof including but not limited to peptide nucleic acid (PNA), phosphorothioated, Locked Nucleic Acids (LNA's), a 2'-O-Methyl (2'OMe) modified nucleotides, a 2'-O-(2-Methoxyethyl) (2'-O-MOE) modified nucleotides, 2'Fluoro modified nucleotides, and a 5'Inverted Dideoxy-T. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid agent is deoxyribonucleic acid (DNA) or ribonucleic acid (RNA), or derivatives thereof. A nucleic acid agent may be single-stranded or double-stranded. A nucleic acid agent may comprise one or more modifications, for example, it may comprise a phosphorothioate (PS) bond (e.g., introduced between the last few (e.g., 3-5) nucleotides at the 5' or 3' end of the nucleic acid agent), thereby being resistant to nuclease degradation (such as exonuclease degradation).

A nucleic acid agent may comprise one or more modified nucleotides. The modified nucleotide may comprise one or more chemical modifications at one or more positions independently selected from the group consisting of a ribose position, a deoxyribose position, a phosphate position, and a base position. For example, the chemical modifications are independently selected from the group consisting of a 2'-position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, methylation, a 3'cap, and a 5'cap. The 5-position modified pyrimidine may be selected from the group consisting of 5-Carboxy-2'-deoxyuridine, 5-Aminoallyl-2'-deoxyuridine, 5-[(3-Indolyl)propionamide-N-allyl]-2'-deoxyuridine, 5-Carboxy-2'-deoxycytidine, 5-Aminoallyl-2'-deoxycytidine, Biotin-16-Aminoallyl-2'-deoxycytidine, 5-(N-benzyl carboxyamide)-2'-deoxyuridine, 5-(N), 5-Aminoallyl-2'-deoxycytidine (5-AA-dC), Biotin-16-Aminoallyl-2'-deoxycytidine (Biotin-16-AA-dC), 5-(N-benzyl carboxyamide)-2'-deoxyuridine, 5-(N-isobutyl carboxyamide)-2'-deoxyuridine, 5-(N-naphthyl methyl carboxyamide)-2'-deoxyuridine, and 5-(N-tryptamino carboxyamide)-2'-deoxyuridine.

As used herein, two or more "nucleic acid agents" are the same only when: 1) they have the same nucleic acid sequences; and 2) each nucleotide in one nucleic acid agent is the same as the corresponding nucleotide in the other nucleic acid agents. In this regard, a nucleotide and its modified version, its analogue or other variants thereof are considered as different nucleotides. Accordingly, if two nucleic acid agents comprise the same nucleic acid sequence while one comprises only unmodified A, C, G, T or U, and the other one comprises modified A, C, G, T or U, they are considered different nucleic acid agents.

The term "polymerase," as used herein, generally refers to any enzyme capable of catalyzing a polymerization reaction. Examples of polymerases include, without limitation, a nucleic acid polymerase, a transcriptase or a ligase. A polymerase can be a polymerization enzyme or a polymerizing enzyme.

The term "aptamer" or "aptamer sequence", as used herein, generally refers to a nucleic acid having a specific binding affinity for a target, e.g., a target molecule, wherein such target is other than a polynucleotide that binds to said nucleic acid through a mechanism which predominantly depends on Watson/Crick base pairing.

The terms "peptide", "polypeptide" and "protein", used interchangeably herein, generally refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.

The term "sequence" as used, for example, in the context of a nucleic acid sequence (e.g., an aptamer sequence) or an amino acid sequence, generally refers to the primary structure, e.g., the order of monomeric subunits (e.g., nucleotides or amino acids). As used herein, sequences (e.g., nucleic acid sequences) with substantially identical order of monomeric subunits (e.g., nucleotides) are considered the same sequence (nucleic acid sequence).

For example, in terms of nucleic acid agents, if the order of A (or analogues, variants, derivatives thereof), C (or analogues, variants, derivatives thereof), T (or analogues, variants, derivatives thereof), G (or analogues, variants, derivatives thereof) and U (or analogues, variants, derivatives thereof) is the same in their primary sequences, these nucleic acid agents are considered as having the same nucleic acid sequence.

In some cases, two molecules (e.g., nucleic acid agents) may have the same order of monomeric subunits (e.g., the order of A (or analogues, variants, derivatives thereof), C (or analogues, variants, derivatives thereof), T (or analogues, variants, derivatives thereof), G (or analogues, variants, derivatives thereof) and U (or analogues, variants, derivatives thereof)), while one comprises unmodified subunits and the other one comprises the corresponding modified subunits, in this case, these two molecules are considered two different molecules (e.g., nucleic acid agents) with the same sequence (e.g., nucleic acid sequence). For example, a modified A is the corresponding modified nucleotide of the nucleotide A, a modified C is the corresponding modified nucleotide of the nucleotide C, a modified T is the corresponding modified nucleotide of the nucleotide T, a modified G is the corresponding modified nucleotide of the nucleotide G, and a modified U is the corresponding modified nucleotide of the nucleotide U.

The terms "label" and "detectable label" may be used interchangeably herein, and generally refer to a molecule capable of being detected, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, streptavidin or haptens) and the like.

The term "fluorescer" as used herein, generally refers to a substance or a portion thereof which is capable of exhibiting fluorescence in the detectable range. Exemplary detectable moieties suitable for use as detectable labels may include e.g., affinity tags and fluorescent proteins.

The term "affinity tag", as used herein, generally refers to a peptide segment that can be attached to a target that can be detected using a molecule that binds the affinity tag and provides a detectable signal (e.g., a fluorescent compound or protein). In principal, any peptide or protein for which an antibody or other specific binding agent is available can be used as an affinity tag.

The term "amplification", as used herein, generally refers to an increase in copy number of a nucleic acid, and it includes the generation of DNA from RNA. The amplification may be performed by any known method. The amplification method may require thermal cycling or may be performed at isothermal conditions. For example, the amplification may include polymerase chain reaction (PCR), nucleic acid sequence-based amplification (NASBA), ligase chain reaction (LCR), strand displacement amplification (SDA), rolling circle amplification (RCA), or a combination thereof. The amplification method may also include a method of RNA amplification, for example, reverse transcription (RT) or RT-PCR. Additionally, the amplification may be DNA amplification or RNA amplification. The nucleic acid amplification may be, for example, a real-time nucleic acid amplification.

The term "PCR", as used herein, generally refers to a method of amplifying a target nucleic acid from a primer pair which specifically binds to the target nucleic acid by using a polymerase. For example, the amplification of a nucleic acid by PCR repeats a cycle of denaturation, annealing, and elongation.

The term "annealing", as used herein, may be used interchangeably with the term "hybridization" and refers to binding of two complementary DNA strands in order to produce hybrid nucleic acid molecules.

The term "identifier", as used herein, generally refers to a signal, message, or information capable of differentiating one subject from another subject, or to objects containing such signal, message or information. The term "unique identifier", as used herein, generally refers to any identifier which is unique among all identifiers used for a given set of objects for a specific purpose. Generally, there is a unique and unambiguous relationship between a unique identifier and the object it identifies. An identifier may be an identification nucleic acid agent. The identification nucleic acid agent may be double-stranded or single-stranded. In the present application, an identification nucleic acid agent may be capable of revealing the identity of a corresponding candidate nucleic acid agent (which may be double-stranded or single-stranded). The identification nucleic acid agent may enable amplification of its corresponding candidate nucleic acid agent (such as a modified nucleic acid agent). For example, the identification nucleic acid agent may contain nucleic acid sequence information of its corresponding candidate nucleic acid agent. In some cases, the identification nucleic acid agent may comprise the same nucleic acid sequence as that of its corresponding candidate nucleic acid agent. When a candidate nucleic acid agent is a modified nucleic acid agent, its corresponding identification nucleic acid agent may be the same as the modified candidate nucleic acid agent, except that the identification nucleic acid agent does not comprise any modified nucleotide while the modified candidate nucleic acid agent comprises at least one modified nucleotide. The identification nucleic acid agent may be capable of being amplified in a nucleic acid amplification reaction and/or being sequenced. For example, the identity of a modified candidate nucleic acid agent may be revealed via sequencing its corresponding identification nucleic acid agent. In the present application, an identification nucleic acid agent (single-stranded or double-stranded) may consist essentially of natural nucleotides. For example, an identification nucleic acid agent may consist of natural DNA.

The term "target", as used herein, generally refers to an object to be detected. For example, a target may be a protein (e.g., an antibody), a polynucleotide, a polypeptide, a virus, a microorganism, a small molecule, a whole cell, a cellular component, a liposome, or a combination thereof. In some embodiments, suitable target may include, for example, small molecules (e.g., organic dyes), amino acids, carbohydrates, lipids, aminoglycosides, antibiotics, peptides, proteins, post-translational modification, nucleic acids, virus, whole cells and/or cellular components. Small molecule targets of interest generally may have a molecular weight of about 800 Daltons or less. Protein targets of interest may include, for example, cell surface receptors, signal transduction factors, and hormones. Cellular targets of interest may include, for example, mammalian cells, particularly human cells, stem cells, tumor cells and bacterial cells. In some embodiments, two or more types of targets (such as protein targets having different amino acid sequences) may be simultaneously tested against a single library of candidate nucleic acid agents or candidate aptamer sequences. In some embodiments, a target or a molecule associated with a target, e.g., via a binding interaction, may be detectably labeled.

The term "specific binding" or "specifically binds to" or "specific for" are used interchangeably herein and generally refer to the binding of an agent (e.g., a nucleic acid agent, such as an aptamer) to a target molecule (e.g., a protein or a part thereof), and the binding is measurably and/or statistically different from a non-specific interaction (e.g., a non-specific interaction may be binding to a reference molecule or a random molecule). Specific binding can be measured, for example, by competition with a control molecule that is similar to the target, for example, an excess of non-labeled target, in this case, specific binding is indicated if the binding of the labeled target to a candidate agent is competitively-inhibited by excess unlabeled target. Specific binding may be exhibited, for example, by a molecule having a Kd for the target of at least about 100 µM, at least about 90 µM, at least about 80 µM, at least about 70 µM, at least about 60 µM, at least about 50 µM, at least about 40 µM, at least about 30 µM, at least about 20 µM, at least about 10 µM, at least about 1 µM, at least about 500 nM, at least about 400 nM, at least about 300 nM, at least about 200 nM, at least about 150 nM, at least about 100 nM, at least about 60 nM, at least about 50 nM, at least about 40 nM, at least about 30 nM, at least about 20 nM, at least about 10 nM, at least about 8 nM, at least about 6 nM, at least about 4 nM, at least about 2 nM, at least about 1 nM, at least about 900 pM, at least about 800 pM, at least about 700 pM, at least about 600 pM, at least about 500 pM, at least about 400 pM, at least about 300 pM, at least about 200 pM, at least about 100 pM, at least about 90 pM, at least about 80 pM, at least about 70 pM, at least about 60 pM, at least about 50 pM, at least about 40 pM, at least about 30 pM, at least about 20 pM, at least about 10 pM, at least about 5 pM, at least about 1 pM, or greater.

The term "affinity", as used herein, generally refers to the strength of the sum total of non-covalent interactions between a single binding site of a molecule (e.g., an aptamer) and its binding partner (e.g., a protein).

The term "Kd" or "Kd value", as used herein, generally refers to a dissociation constant, measured by a technique appropriate for the aptamer and target pair, for example by using Ligand Binding Assays with radioactive or fluorescent measurement, Surface Plasmon Resonance (SPR), Bio-Layer Interferometry (BLI, e.g., the Octet® Systems), SRU biosystems BIND®, Isothermal Titration calorimetry (ITC), or MicroscaleThermophoresis (MST). In some embodiments, the Kd value is determined using a standard fluorescence-based ligand binding assay and saturation analysis. In one example, various concentrations of fluorescently labeled target molecules were incubated with a particle of the present disclosure for at least 3 hours at room temperature with gentle rotation. Each sample was then washed, and the remaining bound target was quantified by measuring the fluorescence of each particle using a flow cytometer. The background-subtracted fluorescence values were then fit to a saturation binding curve, e.g. by using an equilibrium binding model (for example, according to the law of mass action).

The terms "conjugate", "conjugated" and "conjugation" may be used interchangeably and generally refer to any and all forms of covalent or non-covalent linkage, and include, without limitation, direct genetic or chemical fusion, coupling through a linker or a cross-linking agent, and non-covalent association.

The term "template", as used herein, generally refers to the molecule (e.g., nucleic acid agent) to be amplified.

The term "sequencing", as used herein, generally refers to a process or reaction for determining the sequence (e.g., order of monomeric subunits, such as order of nucleotides) of a molecule (e.g., a nucleic acid agent).

The term "immobilized", as used herein, generally refers to attaching or fixing of a molecule or an agent to a substrate or a support (e.g., a particle).

The term "therapeutically active component", as used herein, generally refers to a molecule or an agent showing a therapeutic effect, e.g., for the treatment or control of disease progression.

The term "enriched", as used herein, generally refers to an increase of the amount, quantity or percentage of one or more particular objects within a population.

The term "target binding activity", as used herein, generally refers to an ability to bind to a specific target. For example, a "target binding activity" may be affinity, specificity or bi-specificity.

The term "target-binding induced activity", as used herein, generally refers to an ability induced or caused by the binding of a molecule or agent to an intended target. A "target-binding induced activity" may comprise a catalytic activity, an inhibition activity, an activation activity, a structure switching activity, and/or a cooperative activity.

The term "identity", as used herein, generally refers to information that uniquely distinguishes a molecule or agent from the other molecules or agents. For example, an identity of a nucleic acid agent may be determined or represented by its nucleic acid sequences and/or the nucleotides it comprises.

The terms "forward strand" and "reverse strand", as used herein, generally refer to the two mutually complementary strands of a double-stranded DNA in a specific configuration. For example, when the two strands are stacked up vertically on each other, the top strand is generally conceived to be the forward strand or written by having its 5'-end on the left side and 3'-end on the right side. At the same time, the bottom strand is typically conceived to be the reverse strand or written by having its 3'-end on the left side and 5'-end on the right side, unless otherwise mentioned. As used herein, the "reverse strand" is meaningful relative to the "forward strand", vice versa. These terms are used for the clarity and convenience of describing the invention and its preferred embodiments.

The term "complementary", as used herein, generally refers to polynucleotides (or sequences within one or more polynucleotides) including any nucleic acid sequences that can undergo cumulative base pairing at two or more individual corresponding positions in antiparallel orientation, as in a hybridized duplex.

The term "partial complement", as used herein, generally refers to a nucleic acid molecule with nucleic acid sequences in which at least 10%, at least 20%, at least 30%, at least 40%, at least 50%, at least 60%, at least 70%, at least 80%, or at least 90%, but less than 100%, of the residues of one nucleic acid sequence are complementary to residues in another nucleic acid sequence.

The term "site-specific", as used herein, generally refers to actions or reactions occurring at a specific site of a molecule (e.g., a nucleic acid agent).

The term "encapsulate", as used herein, generally refers to inclusion of a portion of a material in a self-contained space.

The term "compartment", as used herein, generally refers to a self-contained space within a mixture or liquid systems, such as a droplet.

The term "consists essentially of", as used herein, generally refers to a substantial part being made of the indicated components or ingredients.

The term "natural nucleic acid", as used herein, generally refers to nucleic acids occurring in nature. The term "natural DNA", as used herein, generally refers to DNA nucleic acids occurring in nature. In some embodiments, "natural nucleic acid" also comprises synthesized or modified nucleotides not impeding amplification and/or sequencing.

The term "about", when used in the context of numerical values, generally refers to a value less than 1% to 15% (e.g., less than 1%, less than 2%, less than 3%, less than 4%, less than 5%, less than 6%, less than 7%, less than 8%, less than 9%, less than 10%, less than 11%, less than 12%, less than 13%, less than 14%, or less than 15%) above or below an indicated value.

The term "particle", as used herein, generally refers to a solid support, on the surface of which, a plurality of nucleic acid agents may be immobilized. Suitable particles may have any appropriate shape.

The term "member", as used herein, generally refers to an individual unit in a pool or a library. For example, a member in a pool or a library may be a particle or any other solid support, on the surface of which, a plurality of nucleic acid agents may be immobilized.

The term "modified member", as used herein, generally refers to a member (for example, a particle or any other solid support) comprising a plurality of modified candidate nucleic acid agents immobilized thereon.

The term "kernel member", as used herein, generally refers to a member (for example, a particle or any other solid support) comprising a plurality of partially double-stranded nucleic acid agents immobilized thereon. A kernel member may be derived from a template member and may be used to generate a modified member. For example, a template member may be treated to provide a kernel member, which in turn may be treated to provide a modified member.

The term "candidate nucleic acid agents", as used herein, generally refers to one or more nucleic acid agents to be screened or tested. A candidate nucleic acid agent may be immobilized on a solid support (e.g., on the surface of a solid support). A candidate nucleic acid agent may be double-stranded or single-stranded. In some embodiments, a candidate nucleic acid agent may comprise one or more modified nucleotide to provide a modified candidate nucleic acid agent.

The term "double-stranded candidate nucleic acid agent", as used herein, generally refers to one or more double-stranded nucleic acid agent to be screened or tested. A template member (e.g., template particle) may comprise a plurality of double-stranded candidate nucleic acid agents immobilized on a solid support. A double-stranded candidate nucleic acid agent may comprise a forward strand and a complementary reverse strand, with the forward strand and the reverse strand associating with each other (e.g., by base-paring) to generate a double-stranded structure essentially in its entire length.

The term "partially double-stranded candidate nucleic acid agents", as used herein, generally refers to one or more partially double-stranded nucleic acid agent to be screened or tested. A partially double-stranded candidate nucleic acid agent may comprise a first strand (e.g., a forward strand) and a second strand (e.g., a reverse strand), wherein only a part of a first strand may associate with a part of a second strand to form a partially double-stranded structure.

A double-stranded candidate nucleic acid agent may be treated to become a partially double-stranded candidate nucleic acid agent, which may then be further treated to provide a modified candidate nucleic acid agent. The nucleic acid sequence of a modified candidate nucleic acid agent may be the same as that of the partially double-stranded or double-stranded candidate nucleic acid agent generating the modified candidate nucleic acid agent.

Nucleic acid sequence of a partially double-stranded candidate nucleic acid agent (e.g., comprised by any kernel member) may be determined by the nucleic acid sequence of the strand serving as a template in a later nucleic acid polymerization reaction. For example, a partially double-stranded candidate nucleic acid agent may comprise a forward strand and a reverse strand longer than the forward strand, and the nucleic acid sequence of the partially double-stranded candidate nucleic acid agent is the same as that of a strand complementary to the reverse strand.

The term "sequence diversity", as used herein, generally refers to the number of different nucleic acid sequences present in a population, a pool or a library comprising various nucleic acid agents. For example, a sequence diversity of "n" (e.g., 1, 2, 3, or more) means that the nucleic acid agents in a population/pool/library have "n" (e.g., 1, 2, 3, or more) different nucleic acid sequences.

Where a range of values (e.g., a numerical range) is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein, the singular forms "a," "and," and "the" include plural referents unless the context clearly dictates otherwise. Thus, for example, reference to "a particle" includes a plurality of such particles and reference to "the sequence" includes reference to one or more said sequences and equivalents thereof known to those skilled in the art, and so forth.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

In one aspect, the present disclosure provides a particle comprising a plurality of nucleic acid agents immobilized thereto. The plurality of nucleic acid agents may comprise a first population (e.g., candidate nucleic acid agents) and a second population (e.g., identification nucleic acid agents). Nucleic acid agents in the first population may be different from that in the second population. The first population may comprise a plurality of identical copies of a single species of nucleic acid agent. The second population may comprise at least one nucleic acid agent, and the at least one nucleic acid agent may enable amplification of nucleic acid agents comprising the same nucleic acid sequence as the nucleic acid agent comprised in the first population.

In a particle of the present disclosure, the at least one nucleic acid agent comprised in the second population may contain nucleic acid sequence information of the nucleic acid agent in the first population. For example, after amplifying the nucleic acid agent comprised in the second population, the obtained amplification products may have the same or substantially the same nucleic acid sequence as that of the nucleic acid agents in the first population. In some embodiments, the at least one nucleic acid agent comprised in the second population comprises or has the same nucleic acid sequence as that of the nucleic acid agents in the first population. For examples, the at least one nucleic acid agent comprised in the second population may be the same as the nucleic acid agents of the first population, except that the nucleic acid agents of the first population comprise at least one modification (e.g., one or more modified nucleotides or modified bonding, or other modification of the nucleic acid agents), while the at least one nucleic acid agent of the second population does not comprise any modification.

In some embodiments, the at least one nucleic acid agent comprised in the second population is a unique identifier for the nucleic acid agent comprised in the first population. For example, the at least one nucleic acid agent comprised in the second population may be capable of being amplified in a nucleic acid amplification reaction and/or being sequenced. In some embodiments, the identity (e.g., nucleic acid sequences, or the comprised nucleotides) of nucleic acid agents in the first population may be determined by amplifying and/or sequencing the nucleic acid agents of the second population. In some embodiments, the at least one nucleic acid agent comprised in the second population comprises at least one identification nucleic acid agent. For example, the nucleic acid agent comprised in the second population may be the identification nucleic acid agent.

In another aspect, the present disclosure provides a library of particles of the present disclosure. The library may comprise from about 10 to about $10^{15}$ different particles of the present disclosure. For example, the library may comprise at least $10^2$ different particles, at least $10^3$ different particles, at least $10^4$ different particles, at least $10^5$ different particles, at least $10^6$ different particles, at least $10^7$ different particles, at least $10^8$ different particles, at least $10^9$ different particles, at least $10^{10}$ different particles, at least $10^{11}$ different particles, at least $10^{12}$ different particles, at least $10^{13}$ different particles, at least $10^{14}$ different particles, at least $10^{15}$ different particles, at least $10^{16}$ different particles, at least $10^{17}$ different particles, or more particles. In some embodiments, the library is an enriched particle pool. For example, particles with desired properties may be selected and enriched in the pool.

In some embodiments, for any particle comprised in the particle library, a nucleic acid sequence of the nucleic acid agents immobilized thereto is different from that of the nucleic acid agents immobilized to at least one other particle. For example, the particle library may comprise multiple particles and the nucleic acid agents immobilized on one particle may be different from that immobilized on another particle. As another example, the particle library may comprise multiple particles and the nucleic acid sequence of the nucleic acid agents immobilized on one particle may be different from that of the nucleic acid agents immobilized on another particle.

In another aspect, the present application provides a pool comprising a plurality of kernel members. Each kernel member may comprise a plurality of partially double-stranded candidate nucleic acid agents immobilized to a solid support. Each of the partially double-stranded candidate nucleic acid agents may comprise a forward strand and a reverse strand longer than the forward strand. The forward and reverse strand may associate with each other at least partially via base-paring. A nucleic acid sequence of the candidate nucleic acid agents comprised by any kernel member may be different from that of the candidate nucleic acid agents comprised by at least one other kernel member in the pool. In some cases, a kernel member may be a kernel particle, which is a particle with a plurality of partially double-stranded candidate nucleic acid agent immobilized thereon. A 5' end of the forward strand of the partially double-stranded candidate nucleic acid agents may be attached directly or indirectly to the solid support comprised by the kernel member (e.g., kernel particle).

In another aspect, the present application provides a pool comprising a plurality of modified members. Each modified member may comprise a plurality of modified candidate nucleic acid agents immobilized to a solid support. Each modified candidate nucleic acid agent may comprise at least one modified nucleotide. A nucleic acid sequence of the modified candidate nucleic acid agents comprised by any modified member may be different from that of the modified candidate nucleic acid agents comprised by at least one other modified member in the pool. A modified candidate nucleic acid agent may be single-stranded. A 5' end of the single-stranded modified candidate nucleic acid agent may be attached directly or indirectly to the solid support. In addition, the modified candidate nucleic acid agent may not be capable of functioning directly as a template in a nucleic acid amplification reaction. In some cases, the modified candidate nucleic acid agent may consist essentially (or even completely) of modified nucleotides.

In a further aspect, the present application provides a pool comprising a plurality of template members. Each template member may comprise a plurality of double-stranded candidate nucleic acid agents immobilized to a solid support. Each of the double-stranded candidate nucleic acid agents may comprise a forward strand and a complementary reverse strand. A nucleic acid sequence of the double-stranded candidate nucleic acid agents comprised by any template member may be different from that of the double-stranded candidate nucleic acid agents comprised by at least one other template member in the pool. A 5' end of the forward strand of the double-stranded candidate nucleic acid agents may be attached directly or indirectly to the solid support of the template members. The reverse strand of the double-stranded candidate nucleic acid agent may be resistant to 5' to 3' exonuclease digestion. For example, a 5'end of the reverse strand of said double-stranded candidate nucleic acid agent may comprise modified nucleotides, e.g., phosphorothioated nucleotides, Locked Nucleic Acids (LNA's), 2'-O-Methyl (2' OMe) modified nucleotides, 2'-O-(2-Methoxyethyl) (2'-O-MOE) modified nucleotides, 2' Fluoromodified nucleotides, or 5' Inverted Dideoxy-Tbe phosphorothioated nucleotides.

A member (e.g., a kernel member, a modified member and/or a template member) in a pool may comprise a solid support, on the surface of which, a plurality of nucleic acid agents (single-stranded, double-stranded and/or partially double-stranded) may be immobilized. The solid support may be any suitable solid material capable of being immobilized with nucleic acid agents. It may have any shape or size. For example, a suitable solid support may comprise a particle (e.g., a bead), a slide, a well, an area of a plate, a chip, a spot in an array, etc. There may be a clear boundary between one member and any other member in the same pool. In some embodiments, no solid boundary is present to prevent fluid communication among different members in the same pool.

In some cases, a solid support may be a particle of the present application. The solid support may be non-magnetic, magnetic or paramagnetic. For example, the solid support may have at least one dimension of from about 50 nm to about 100 µm (e.g., from about 50 nm to about 1 µm, from about 50 nm to about 500 nm, from about 50 nm to about 100 nm, from about 500 nm to about 100 µm, from about 1 µm to about 100 µm, or from about 50 µm to about 100 µm).

Sequence diversity of the candidate nucleic acid agents (e.g., double-stranded candidate nucleic acid agents, partially double-stranded candidate nucleic acid agents and/or modified candidate nucleic acid agents) comprised by any member (e.g., template member, kernel member, and/or modified member) in a pool of the present disclosure may be less than that of the total candidate nucleic acid agents (e.g., double-stranded candidate nucleic acid agents, partially double-stranded candidate nucleic acid agents and/or modified candidate nucleic acid agents) comprised by all the members (e.g., template member, kernel member, and/or modified member) in that pool.

Sequence diversity of the candidate nucleic acid agents (e.g., double-stranded candidate nucleic acid agents, partially double-stranded candidate nucleic acid agents and/or modified candidate nucleic acid agents) comprised by any member (e.g., template member, kernel member, and/or modified member) in a pool according to the present disclosure may be from 1 to 1000 (e.g., less than 900, less than 800, less than 700, less than 600, less than 500, less than 400, less than 300, less than 200, less than 100, less than 50, less than 40, less than 30, less than 20, less than 15, less than 10, less than 9, less than 8, less than 7, less than 6, less than 5, less than 4, less than 3, or less than 2).

Any one of the members (e.g., template member, kernel member, and/or modified member) in a pool according to the present disclosure may comprise at least $1\times10^2$ (e.g., at least $1\times10^3$, at least $1\times10^4$, at least $1\times10^5$, at least $1\times10^6$, at least $1\times10^7$, at least $1\times10^8$, at least $1\times10^9$, at least $1\times10^{10}$, at least $1\times10^{11}$, at least $1\times10^{11}$ or more) copies of candidate nucleic acid agents (e.g., double-stranded candidate nucleic acid agents, partially double-stranded candidate nucleic acid agents and/or modified candidate nucleic acid agents, accordingly) having the same nucleic acid sequence.

In some cases, for each candidate nucleic acid agent (e.g., double-stranded candidate nucleic acid agent, partially double-stranded candidate nucleic acid agent and/or modified candidate nucleic acid agent) comprised by any member (e.g., template member, kernel member, and/or modified member, accordingly), a corresponding identification nucleic acid agent (double-stranded or single-stranded) may be comprised by the same member. The identification nucleic acid agent may enable amplification of its corresponding candidate nucleic acid agent. The identification nucleic acid agents comprised by a template member may be double-stranded, and the identification nucleic acid agents comprised by a kernel member or a modified member may be single-stranded.

On any member (e.g., template member, kernel member, and/or modified member) of a pool, a ratio of the number of a candidate nucleic acid agent to that of its corresponding identification nucleic acid agent may be from about $10^{10}$:1 to about 1:1 (e.g., from about $10^9$:1 to about 1:1, from about $10^8$:1 to about 1:1, from about $10^7$:1 to about 1:1, from about $10^6$:1 to about 1:1, from about $10^5$:1 to about 1:1, from about $10^4$:1 to about 1:1, from about $10^3$:1 to about 1:1, from about 100:1 to about 1:1, from about 90:1 to about 1:1, from about 80:1 to about 1:1, from about 70:1 to about 1:1, from about 60:1 to about 1:1, from about 50:1 to about 1:1, from about 40:1 to about 1:1, from about 30:1 to about 1:1, from about 20:1 to about 1:1, from about 15:1 to about 1:1, from about 10:1 to about 1:1, from about 9:1 to about 1:1, from about 8:1 to about 1:1, from about 7:1 to about 1:1, from about 6:1 to about 1:1, from about 5:1 to about 1:1, from about 4:1 to about 1:1, from about 3:1 to about 1:1, or from about 2:1 to about 1:1). In some embodiment, on any member of a pool, the number of a candidate nucleic acid agent to that of its corresponding identification nucleic acid agent may be in a ratio of no more than 1:10, no more than about 1:100, no more than about 1:1000, or no more than about 1:10000).

There may be from about $10^2$ to about $10^{10}$ (e.g., at least about $10^2$ nucleic acid agents, at least about $10^3$ nucleic acid agents, at least about $10^4$ nucleic acid agents, at least about $10^5$ nucleic acid agents, at least about $10^6$ nucleic acid agents, at least about $10^7$ nucleic acid agents, at least about $10^8$ nucleic acid agents, at least about $10^9$ nucleic acid agents) nucleic acid agents (candidate nucleic acid agents and/or identification nucleic acid agents) immobilized to any solid support comprised by a member of a pool according to the present application.

The identification nucleic acid agent may be immobilized to the same solid support as its corresponding candidate nucleic acid agent. In addition, an identification nucleic acid agent may be capable of being amplified in a nucleic acid amplification reaction and/or being sequenced. An identification nucleic acid agent may contain nucleic acid sequence information of its corresponding candidate nucleic acid agent. For example, an identification nucleic acid agent may comprise the same nucleic acid sequence as that of its corresponding candidate nucleic acid agent. An identification nucleic acid agent may consist essentially of natural nucleotides. For example, an identification nucleic acid agent may consist of natural DNA.

For the modified members, the identification nucleic acid agent may be the same as its corresponding modified candidate nucleic acid agent, except that the identification nucleic acid agent does not comprise any modified nucleotide while the modified candidate nucleic acid agent comprises at least one modified nucleotide.

For the template members, the reverse strand of the double-stranded identification nucleic acid agent may be susceptible to 5' to 3' exonuclease digestion. For example, the reverse strand of the double-stranded identification nucleic acid agent may not contain any modifications that render it resistant to 5' to 3' exonuclease digestion.

In some cases, the template member may further comprise a plurality of single-stranded forward primers immobilized on the solid support, the single-stranded forward primers may be capable of hybridizing with the reverse strand of the double-stranded candidate nucleic acid agent at least partially via base-paring. For example, the single-stranded forward primers may associate with the reverse strand of the double-stranded candidate nucleic acid agents to form partially double-stranded candidate nucleic acid agents of the kernel members.

In a particle of the present disclosure, the single species of nucleic acid agent comprised in the first population (e.g., candidate nucleic acid agent) may be capable of specifically binding to a target. The modified candidate nucleic acid agents comprised by the modified members of the present application may also be capable of specifically binding to a target.

The target may be a polynucleotide, a polypeptide, a nucleic acid molecule, a protein target, a small molecule target, a whole cell, a cellular component, a liposome or a combination thereof. Suitable target may include, for example, small molecule s (e.g., organic dyes), amino acids, carbohydrates, lipids, aminoglycosides, antibiotics, peptides, proteins, post-translational modification, nucleic acids, virus, whole cells and cellular components. Small molecule targets of interest generally have a molecular weight of about 800 Daltons or less. Protein targets of interest may include, for example, cell surface receptors, signal transduction factors, and hormones. Cellular targets of interest may include, for example, mammalian cells, particularly human cells; stem cells; tumor cells and bacterial cells. In some embodiments, two or more types of targets (such as protein targets having different amino acid sequences) may be simultaneously tested against a single library of candidate nucleic acid agents or candidate aptamer sequences. In some embodiments, a target molecule or a molecule associated with a target molecule, e.g., via a binding interaction, may be detectably labeled.

Suitable labels may include radioactive isotopes, fluorescers, chemiluminescers, chromophores, enzymes, enzyme substrates, enzyme cofactors, enzyme inhibitors, dyes, metal ions, metal sols, ligands (e.g., biotin, avidin, streptavidin or haptens), affinity tags and the like.

Exemplary affinity tags suitable for use may include, but are not limited to, a monoclonal antibody for the target molecule, a polyclonal antibody for the target molecule, a fluorescent antibody, a biotinylated antibody, a monocytic adaptor protein (MONA) binding peptide, a T7 binding peptide, a streptavidin binding peptide, a polyhistidine tract, protein A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), or other antigenic epitope or binding domain. See, in general, Ford et al., Protein Expression and Purification 2:95 (1991). DNA molecule s encoding affinity tags are available from commercial suppliers (e.g., Pharmacia Biotech, Piscataway, N.J.).

Any fluorescent polypeptide (also referred to herein as a fluorescent label) may be suitable for use as a detectable label. A suitable fluorescent polypeptide will be one that will readily provide a detectable signal that can be assessed qualitatively (positive/negative) and quantitatively (comparative degree of fluorescence). Exemplary fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof. Further suitable fluorescent polypeptides, as well as specific examples of those listed herein, are provided in the art and are well known.

Biotin-based labels may also be employed. Biotinylation agents that may be used include, for example, amine-reactive and thiol-reactive agents, for the biotinylation of proteins, nucleic acids, carbohydrates, carboxylic acids; see, e.g., chapter 4, Molecular Probes Catalog, Haugland, 6th Ed. 1996, hereby incorporated by reference. A biotinylated substrate can be detected by binding of a detectably labeled biotin binding partner, such as avidin or streptavidin. Similarly, a large number of haptenylation reagents are also known.

In some embodiments, the single species of nucleic acid agent comprised in the first population is or comprise an aptamer. In some embodiments, the modified candidate nucleic acid agent comprised by the modified members is or comprise an aptamer.

The nucleic acid agent comprised in the first population of the particle or the modified candidate nucleic acid agent comprised by the modified member may be capable of specifically binding to a target with a Kd of from about 1 pM to about 100 µM, at least about 90 µM, at least about 80 µM, at least about 70 µM, at least about 60 µM, at least about 50 µM, at least about 40 µM, at least about 30 µM, at least about 20 µM, at least about 10 µM, at least about 1 µM, at least about 500 nM, at least about 400 nM, at least about 300 nM, at least about 200 nM, or at least about 100 nM. For example, the nucleic acid agent comprised in the first population may be capable of specifically binding to a target with a Kd of at least about 90 nM, at least about 80 nM, at least about 70 nM, at least about 60 nM, at least about 50 nM, at least about 40 nM, at least about 30 nM, at least about 20 nM, at least about 10 nM, at least about 8 nM, at least about 6 nM, at least about 4 nM, at least about 2 nM, at least about 1 nM, at least about 900 pM, at least about 800 pM, at least about 700 pM, at least about 600 pM, at least about 500 pM, at least about 400 pM, at least about 300 pM, at least about 200 pM, at least about 100 pM, at least about 90 pM, at least about 80 pM, at least about 70 pM, at least about 60 pM, at least about 50 pM, at least about 40 pM, at least about 30 pM, at least about 20 pM, at least about 10 pM, at least about 5 pM, at least about 1 pM, or greater.

Each of the nucleic acid agent comprised in the first population of the particle or each of the modified candidate nucleic acid agent comprised by the modified carriers may comprise at least one modification. In some embodiments, the at least one modification comprises one or more modified nucleotide, in that case, the nucleic acid agent comprised in the first population is a modified nucleic acid agent.

In some embodiments, none of the nucleic acid agents comprised in the first population (e.g., none of the modified candidate nucleic acid agents) is capable of functioning directly as a template in a nucleic acid amplification reaction. For example, each of the nucleic acid agent comprised in the first population (e.g., each of the modified candidate nucleic acid agents) may comprise at least one modified nucleotide and may not be capable of functioning directly as a template in a nucleic acid amplification reaction.

In some embodiments, each of the nucleic acid agent comprised in the first population or each of the modified candidate nucleic acid agent consists essentially of modified nucleotides. In some embodiments, each of the nucleic acid agent comprised in the first population or each of the modified candidate nucleic acid agent consists completely of modified nucleotides.

The modified nucleotide may comprise one or more chemical modifications at one or more positions independently selected from the group consisting of a ribose position, a deoxyribose position, a phosphate position, and a base position. For example, the chemical modifications are independently selected from the group consisting of a 2'-position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, methylation, a 3' cap, and a 5' cap. The 5-position modified pyrimidine may be selected from the group consisting of 5-Carboxy-2'-deoxyuridine, 5-Aminoallyl-2'-deoxyuridine, 5-[(3-Indolyl)propionamide-N-allyl]-2'-deoxyuridine, 5-Carboxy-2'-deoxycytidine, 5-Aminoallyl-2'-deoxycytidine, Biotin-16-Aminoallyl-2'-deoxycytidine, 5-(N-benzylcarboxyamide)-2'-deoxyuridine, 5-Aminoallyl-2'-deoxycytidine (5-AA-dC), Biotin-16-Aminoallyl-2'-deoxycytidine (Biotin-16-AA-dC), 5-(N-benzyl carboxyamide)-2'-deoxyuridine, 5-(N-isobutyl carboxyamide)-2'-deoxyuridine, 5-(N-naphthyl methyl carboxyamide)-2'-deoxyuridine, and 5-(N-tryptaminocarboxyamide)-2'-deoxyuridine.

In a particle of the present disclosure, the second population may comprise a plurality of identical copies of nucleic acid agent. For any member of a pool according to the present disclosure, the identification nucleic acid agents (double-stranded or single-stranded) may comprise a plurality of identical copies of nucleic acid agent.

In some embodiments, the at least one nucleic acid agent comprised in the second population consists essentially of natural nucleotides. For example, the at least one nucleic acid agent comprised in the second population may consist of natural DNA.

In a particle of the present disclosure, the nucleic acid agents comprised in the first population and those comprised in the second population may be in a ratio of from about $10^{10}$:1 to about 1:1. For example, in a ratio of from about $10^9$:1 to about 1:1, from about $10^8$:1 to about 1:1, from about $10^7$:1 to about 1:1, from about $10^6$:1 to about 1:1, from about $10^5$:1 to about 1:1, from about $10^4$:1 to about 1:1, from about $10^3$:1 to about 1:1, from about 100:1 to about 1:1, from about 90:1 to about 1:1, from about 80:1 to about 1:1, from about 70:1 to about 1:1, from about 60:1 to about 1:1, from about 50:1 to about 1:1, from about 40:1 to about 1:1, from about 30:1 to about 1:1, from about 20:1 to about 1:1, from about 15:1 to about 1:1, from about 10:1 to about 1:1, from about 9:1 to about 1:1, from about 8:1 to about 1:1, from about 7:1 to about 1:1, from about 6:1 to about 1:1, from about 5:1 to about 1:1, from about 4:1 to about 1:1, from about 3:1 to about 1:1, or from about 2:1 to about 1:1. In some embodiment, the nucleic acid agents comprised in the first population and those comprised in the second population may be in a ratio of no more than 1:10, no more than about 1:100, no more than about 1:1000, or no more than about 1:10000.

In another aspect, the present disclosure provides a method for identifying a nucleic acid agent having a desired property from a mixture of candidate nucleic acid agents. The method may comprise: a) obtaining one or more particles (or library/pool of particles) of the present disclosure; b) exposing the particles (or library/pool of particles) to a target, thereby determining a presence or absence of the desired property; c) isolating one or more particles having immobilized thereto a candidate nucleic acid agent having the desired property; and d) identifying the candidate nucleic acid agent having the desired property from the isolated particles.

The target may be a polynucleotide, a polypeptide, a nucleic acid molecule, a protein target, a small molecule target, a whole cell, a cellular component, a liposome or a combination thereof. The target may be as described in other parts of the present disclosure. In some embodiments, the target is selected from the group consisting of a protein target, a small molecule target, a whole cell, a cellular component or a liposome.

In the present disclosure, a desired property may be a target binding activity or a target binding induced activity. The target binding activity may be affinity, specificity or bi-specificity. The target-binding induced activity may be a catalytic activity, an inhibition activity, an activation activity, a modification of an inhibition activity or activation activity, a structure switching activity, and/or a cooperative activity.

The desired property may be a property of the nucleic acid agent of the first population. For example, nucleic acid agents in the first population may be able to specifically bind to a target (e.g., a protein target). An identity of the nucleic acid agent having the desired property (e.g., the modified nucleic acid agent, such as an aptamer comprising one or more modified nucleotide) may be determined from the nucleic acid agent comprised in the second population (e.g., the identification nucleic acid agent, such as a corresponding DNA molecule consisting of natural nucleotides). For example, nucleic acid sequence of the nucleic acid agent having the desired property may be determined by amplifying and/or sequencing the nucleic acid agents in the second population.

A method for identifying a nucleic acid agent having a desired property according to the present disclosure may comprise quantifying a signal from the detectable labels (e.g., a label attached to the nucleic acid agent or to the target). In some embodiments, the method includes isolating and/or enriching a population of the plurality of particles based on the quantitated signal. In some embodiments, the method includes introducing one or more mutations into one or more nucleic acid agents or into one or more nucleic acid agents having the desired property. In some embodiments, the method comprises iteratively repeating one or more of the steps.

In some embodiments, the intensity of the signal from the detectable labels is indicative of a binding interaction between the nucleic acid agents immobilized to the particle of the present disclosure and one or more detectably labeled targets. The signal may increase with an increase in binding affinity between the nucleic acid agents and the detectably labeled target.

The nucleic acid agent having the desired property may be amplified with an amplification method as described above, e.g., PCR, reverse transcriptase PCR or primer extension as appropriate in view of the nucleic acid agent sequences or aptamer sequences to be amplified.

Isolation and/or sorting may be conducted using a variety of methods and/or devices known by those skilled in the art, such as flow cytometry (e.g., Fluorescence Activated Cell Sorting (FACS) or Ramen flow cytometry), fluorescence microscopy, optical tweezers, micro-pipettes, and microfluidic magnetic separation devices and methods. In some embodiments, where the detectably labeled target is a fluorescently labeled target, Fluorescence Activated Cell Sorting (FACS) may be employed to quantitatively sort particle immobilized nucleic acid agents or aptamers based on one or more fluorescence signals. One or more sort gates or threshold levels may be utilized in connection with one or more detectable labels to provide quantitative sorting over a wide range of nucleic acid agent-target interactions or aptamer sequence-target interactions. In addition, the screening stringency may be quantitatively controlled, e.g., by modulating the target concentration and setting the position of the sort gates.

Where, for example, the fluorescence signal is related to the binding affinity of a nucleic acid agent (e.g., an aptamer) to a target, the sort gates and/or stringency conditions may be adjusted to select for nucleic acid agents (e.g., aptamers) having a desired affinity or desired affinity range for the target. In some cases, it may be desirable to isolate the highest affinity nucleic acid agent or aptamers from a particular library of nucleic acid agents or aptamer sequences. However, in other cases nucleic acid agents or aptamers falling within a particular range of binding affinities may be isolated.

In one aspect, the present disclosure provides a method for generating a particle, a library of particles, or a pool of members according to the present disclosure.

In one aspect, the present disclosure provides a method for generating one or more modified particles with nucleic acid agents immobilized thereto, such as the particles or the library of particles of the present disclosure. The method may comprise: a) obtaining one or more template particles, each with a plurality of double-stranded nucleic acid agents immobilized thereto, each of the double-stranded nucleic acid agent may comprise a forward strand and a reverse strand. The reverse strand may be complementary to the forward strand. The forward strand may be attached to the particle (e.g., via a forward primer).

In some embodiments, the method further comprises immobilizing a plurality of double-stranded nucleic acid agents to the particle prior to a). For example, a plurality of specifically designed forward primers may be immobilized to the particles, and then, nucleic acid amplifications (e.g., PCR reaction, such as emulsion PCR) may be performed to immobilize the plurality of double-stranded nucleic acid agents to the particle.

For each template particle, the plurality of double-stranded nucleic acid agents may comprise a first double-stranded population (e.g., double-stranded candidate nucleic acid agents) and a second double-stranded population (e.g., double-stranded identification nucleic acid agents), the nucleic acid agents comprised in the first double-stranded population may be different from that in the second double-stranded population.

The first and the second double-stranded populations may be generated directly during the immobilization process, e.g., via the nucleic acid amplifications (e.g., PCR reaction, such as emulsion PCR), for example, by using different reverse primers for the emulsion PCR. For example, a reverse primer with (protected) nuclease-resistant phosphorothioated (PS) backbone may be used in the emulsion PCR to generate the first double-stranded population, and simultaneously, a reverse primer without (unprotected) nuclease-resistant phosphorothioated (PS) backbone may be used in the emulsion PCR to generate the second double-stranded population. In some embodiments, the ratio of the protected and unprotected reverse primers in the PCR reaction mixture is predetermined to control the ratio of nucleic acid agents comprised by the first and the second double-stranded population.

In some embodiments, only one population of double-stranded nucleic acid agents may be present on the particles after the immobilization process, e.g., after the nucleic acid amplifications (e.g., PCR reaction, such as emulsion PCR). Then, these particles comprising only one population of double-stranded nucleic acid agents may be further treated (e.g., partially digested) to generate the first double-stranded nucleic acid population and the second double-stranded population. Thus, in some embodiments, the method further comprises, prior to a), treating one or more particles with a plurality of identical double-stranded nucleic acid agents immobilized thereto (e.g., with partial digestion) to generate the template particles comprising the first and the second double-stranded populations.

In some embodiments, the first double-stranded population comprises a plurality of identical copies of a single species of nucleic acid agent; the second double-stranded population comprises at least one nucleic acid agent, and the at least one nucleic acid agent of the second double-stranded population enables amplification of nucleic acid agents comprising the same nucleic acid sequence as the nucleic acid agent comprised in the first double-stranded population.

In some embodiments, the at least one nucleic acid agent comprised in the second double-stranded population contains nucleic acid sequence information of the nucleic acid agent in the first double-stranded population. The at least one nucleic acid agent comprised in the second double-stranded population may comprise the same nucleic acid sequence as that comprised in the nucleic acid agent of the first double-stranded population.

The second double-stranded population may comprise a plurality of identical copies of the at least one nucleic acid agent.

The method may further comprise b) treating the template particle obtained in a) to obtain a modified particle, wherein each modified particle may comprise at least one modified nucleic acid agent derived from the first double-stranded population and at least one identification nucleic acid agent derived from the second double-stranded population; the at least one modified nucleic acid agent may contain at least one modified nucleotide and is not capable of functioning directly as a template in a nucleic acid amplification reaction; and the at least one identification nucleic acid agent may enable amplification of nucleic acid agents comprising the same nucleic acid sequence as the modified nucleic acid agent derived from the first double-stranded population.

In the method, b) may comprise: b1) treating the template particle obtained in a) so that only the reverse strand of the nucleic acid agent comprised in the second double-stranded population is removed. For example, b1) may comprise treating the template particle obtained in a) with a 5' to 3' exonuclease to remove only the reverse strand of the nucleic acid agent comprised in the second double-stranded population.

For example, the reverse strand of nucleic acid agents comprised in the first double-stranded population may be resistant to 5' to 3' exonuclease digestion. For example, a 5'end of the reverse strands of nucleic acid agents in the first double-stranded population may comprise modified nucleotides, such as phosphorothioated, Locked Nucleic Acids (LNA's), 2'-O-Methyl (2'OMe) modified nucleotides, 2'-O-(2-Methoxyethyl) (2'-O-MOE) modified nucleotides, 2' Fluoromodified nucleotides, or 5' Inverted Dideoxy-T. A reverse strand of the at least one nucleic acid agent comprised in the second double-stranded population may be susceptible to 5' to 3' exonuclease digestion. For example, the reverse strand of the at least one nucleic acid agent comprised in the second double-stranded population may not contain any modifications that render it resistant to 5' to 3' exonuclease digestion.

For example, the reverse strand of the nucleic acid agents comprised in the first double-stranded population may be resistant to 5' to 3' exonuclease digestion. In some embodiments, a 5'end of the reverse strand of the nucleic acid agents in the first double-stranded population is phosphorothioated, and the reverse strand of the at least one nucleic acid agent comprised in the second double-stranded population is susceptible to 5' to 3' exonuclease digestion. Thus, by treating the template particle obtained in a) with a 5' to 3' exonuclease, only the reverse strand of the nucleic acid agent comprised in the second double-stranded population may be removed.

In the method for generating a particle of the present disclosure, removing only the reverse strand of the at least one nucleic acid agent in the second double-stranded population may comprise treating the particle with a 5' to 3' exonuclease, such as a T5 exonuclease, an Exonuclease VIII, truncated, or a T7 exonuclease. For example, since the reverse strand of nucleic acid agents in the first double-stranded population may be resistant to 5' to 3' exonuclease digestion, while the reverse strand of nucleic acid agents in the second double-stranded population may be susceptible to 5' to 3' exonuclease digestion, treating the particle with a 5' to 3' exonuclease may only digest and remove the reverse strand of nucleic acid agents in the second double-stranded population. The exonuclease digestion may be carried out at a temperature of at least about 15° C., at least about 20° C., at least about 25° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 41° C., at least about 42° C., at least about 43° C., at least about 44° C., at least about 45° C., at least about 46° C., at least about 47° C., at least about 48° C., at least about 49° C., or at least about 50° C.

In the method, b) may further comprise b2) treating the particle obtained in b1) so that a substantial part of the forward strand of the nucleic acid agents in the first double-stranded population is removed. In some cases, the reverse strand of the nucleic acid agents of the first double-stranded population may be hybridized to a partial complement thereof attached to the particle. In the process of b2), the forward strand of the at least one nucleic acid agent of the second double-stranded population may remain intact and attached to the particle.

In some embodiments, during the process of b2), the particle obtained in b1) may be treated with a site-specific nicking enzyme to generate nicked forward strand of nucleic acid agents comprised in said first double-stranded population, and then further treated with an exonuclease to remove a substantial part of the forward strand of the nucleic acid agents in the first double-stranded population.

Any enzyme suitable for site-specifically generating a nicked forward strand may be employed, for example, a nicking enzyme may be selected from Nt.AlwI, Nt.BbvCI, Nt.BsmAI, Nt.BspQI, Nt.BstNBI, Nb.BbvCI, Nb.BsmI, Nb.BsrDI, Nb.BssSI, N b.BtsI, or a combination thereof. For example, after nicking, a nicked forward strand may be generated, rendering it susceptible to exonuclease digestion. The nicking reaction may be carried out at a temperature of at least about 30° C., at least about 35° C., at least about 40° C., at least about 45° C., at least about 46° C., at least about 47° C., at least about 48° C., at least about 49° C., at least about 50° C., at least about 51° C., at least about 52° C., at least about 53° C., at least about 54° C., at least about 55° C., at least about 56° C., at least about 57° C., at least about 58° C., at least about 59° C., at least about 60° C., at least about 65° C. or at least about 70° C.

For example, the nicking enzyme may recognize a specific site in the double-stranded nucleic acid agents of the first double-stranded population and hydrolyze only one of the two strands thereof (for example, hydrolyze the forward strand of nucleic acid agents in the first double-stranded population), to produce a "nicked" strand. Since the reverse strand of the nucleic acid agents in the second double-stranded population has been removed in the process of b1), the nicking enzyme could not recognize and hydrolyze (e.g., cut) the forward strand of the nucleic acid agents in the second double-stranded population (because it is single-stranded now, which cannot be recognized by the nicking enzyme). Thus, a nicked forward strand of nucleic acid agents comprised in the first double-stranded population may be generated, which may then be digested by an exonuclease to remove a substantial part thereof, while the forward strand of the at least one nucleic acid agent of the second double-stranded population may remain intact and attached to the particle.

In some embodiments, during the process of b2), the particle obtained in b1) may be treated with a site-specific restriction enzyme to generate double-stranded break of nucleic acid agents comprised in the first double-stranded population, and then further treated with an exonuclease to remove a substantial part of the forward strand of the nucleic acid agents in the first double-stranded population.

Any enzyme suitable for site-specifically generating a double-stranded break of nucleic acid agents may be employed, for example, a site-specific restriction enzyme may be selected from NdeI, EcoRI, XhoI, HindIII, Ncos, AgeI, BamHI, KpnI, MfeI, SalI, or a combination thereof. For example, after treating the particles with a site-specific restriction enzyme, double-stranded breaks may be generated, rendering the forward strand of the nucleic acid agents of the first double-stranded population susceptible to 5' to 3' exonuclease digestion. The site-specific restriction enzyme digestion may be carried out at a temperature of at least about 25° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 41° C., at least about 42° C., at least about 43° C., at least about 44° C., at least about 45° C., at least about 46° C., at least about 47° C., at least about 48° C., at least about 49° C., at least about 50° C., or at least about 55° C.

For example, the site-specific restriction enzyme may recognize a specific site in the double-stranded nucleic acid agents of the first double-stranded population and expose the 5' end of the forward strand of nucleic acid agents in the first double-stranded population after generating a double-stranded break. Since the reverse strand of the nucleic acid agents in the second double-stranded population has been removed in the process of b1), the site-specific restriction enzyme could not recognize and digest (e.g., cut) the forward strand of the nucleic acid agents in the second double-stranded population (because it is single-stranded now, which cannot be recognized by the restriction enzyme). Thus, the forward strand of nucleic acid agents comprised in the first double-stranded population may be cut with its 5' end exposed, which may then be digested by an exonuclease to remove a substantial part thereof, while the forward strand of the at least one nucleic acid agent of the second double-stranded population may remain intact and attached to the particle.

To remove a substantial part of the forward strands of nucleic acid agents in the first double-stranded population, the particle may further be treated with an exonuclease. For example, after a particle is treated with a site-specific nicking enzyme or a site-specific restriction enzyme, an exonuclease (e.g., a 5' to 3'exonuclease) may be added to the reaction system or to the obtained particle. In some embodiments, after treating the particle with a nicking enzyme or a site-specific restriction enzyme, 5'ends of the forward strand of nucleic acid agents in the first double-stranded population may be exposed at the nicked or restriction enzyme recognition site and become susceptible to 5' to 3'exonuclease digestion, then, these forward strands may be digested and removed starting from the nicked site or restriction enzyme recognition site. The exonuclease digestion may be carried out at a temperature of at least about 15° C., at least about 20° C., at least about 25° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 41° C., at least about 42° C., at least about 43° C., at least about 44° C., at least about 45° C., at least about 46° C., at least about 47° C., at least about 48° C., at least about 49° C., or at least about 50° C.

In some embodiments, in b2), a remaining part of the forward strand of the nucleic acid agents in the first double-stranded population is not removed and remains attached to the particle, serving as the partial complement, and the reverse strand of the nucleic acid agents in the first double-stranded population remains hybridized to the remaining part of the forward strand of the nucleic acid agents in the first double-stranded population.

In some embodiments of the method for generating the modified particles, the template particle in a) further comprises a third population containing a plurality of single-stranded nucleic acid agents attached thereto (e.g., immobilized forward primers complementary to the reverse strand of nucleic acid agents of the first double-stranded population), the plurality of single-stranded nucleic acid agents of the third population serve as the partial complement in b2) and hybridize to the reverse strand of the nucleic acid agents of the first double-stranded population subsequent to removal of a substantial part of the forward strand of nucleic acid agents in the first double-stranded population.

For example, the single-stranded nucleic acid agent of the third population may comprise a sequence homologous or identical to a stretch of sequence at the 5' end of the forward strand of nucleic acid agents in the first double-stranded population, thereby being capable of hybridizing to a stretch of complementary sequence at or adjacent to the 3' end of the reverse strand of nucleic acid agents in the first double-stranded population. A ratio between the combined number of double-stranded nucleic acid agents of the first and second population immobilized to the template particle in step a) and that of the single-stranded nucleic acid agents of the third population immobilized to the template particle in step a) is from about 10:1 to about 1:10. For example, the ratio between the number of double-stranded nucleic acid agents of the first and second double-stranded population immobilized to the template particle of a) and that of the single-stranded nucleic acid agents of the third population immobilized to the template particle of a) may be from about 2:1 to about 1:2, e.g., may be about 1:1. The hybridization may be carried out at a temperature of at least about 45° C., at least about 50° C., at least about 51° C., at least about 52° C., at least about 53° C., at least about 54° C., at least about 55° C., at least about 56° C., at least about 57° C., at least about 58° C., at least about 59° C., at least about 60° C., at least about 61° C., at least about 62° C., at least about 63° C., at least about 64° C., at least about 65° C., at least about 66° C., at least about 67° C., at least about 68° C., at least about 69° C., at least about 70° C., or at least about 75° C.

In some embodiments, the reverse strand of the nucleic acid agents of the first double-stranded population detaches from the particle and is re-attached by annealing to the partial complement thereof attached to the particle. The annealing may occur at a temperature of at least about 45° C., at least about 50° C., at least about 51° C., at least about 52° C., at least about 53° C., at least about 54° C., at least about 55° C., at least about 56° C., at least about 57° C., at least about 58° C., at least about 59° C., at least about 60° C., at least about 61° C., at least about 62° C., at least about 63° C., at least about 64° C., at least about 65° C., at least about 66° C., at least about 67° C., at least about 68° C., at least about 69° C., at least about 70° C., or at least about 75° C.

In the method, b) may further comprise b3) incorporating nucleotides to generate nucleic acid strand complementary to the reverse strand of the nucleic acid agents of the first double-stranded population. In some cases, the partial complement on the particle of b2) may be extended with incorporation of nucleotides to generate nucleic acid strand complementary to the reverse strand of the nucleic acid agents of the first double-stranded population. For example, the nucleotides may be incorporated with a nucleic acid polymerase. The incorporated nucleotides may comprise at least one modified nucleotide.

Any suitable polymerase may be used, for example, a polymerase may be selected from Bst 3.0 DNA Polymerase, Bst 2.0 DNA Polymerase, Therminator™ DNA Polymerase, Deep VentR™ DNA Polymerase, Deep VentR™ (exo−) DNA Polymerase, OneTaq® Hot Start DNA Polymerase, Sulfolobus DNA Polymerase IV, phi29 DNA Polymerase, Klenow Fragment (3'→5' exo-), DNA Polymerase I, Large (Klenow) Fragment, KOD Hot Start DNA Polymerase, KOD Xtreme™ Hot Start DNA Polymerase, or a combination thereof. Nucleic acid strands synthesis (i.e., strand extension with incorporation of nucleotides) may be carried out at a temperature of at least about 45° C., at least about 50° C., at least about 51° C., at least about 52° C., at least about 53° C., at least about 54° C., at least about 55° C., at least about 56° C., at least about 57° C., at least about 58° C., at least about 59° C., at least about 60° C., at least about 61° C., at least about 62° C., at least about 63° C., at least about 64° C., at least about 65° C., at least about 66° C., at least about 67° C., at least about 68° C., at least about 69° C., at least about 70° C., or at least about 75° C.

In the method, b) may further comprise b4) generating a modified particle with a plurality of single-stranded nucleic acid agents immobilized thereto, the plurality of single-stranded nucleic acid agents comprises a first single-stranded population and a second single-stranded population; the at least one modified nucleic acid agent is comprised in the first single-stranded population and the at least one identification nucleic acid agent is comprised in the second single-stranded population.

For example, b4) may comprise removing the reverse strand of all the nucleic acid agents attached to the particle obtained in b3), thereby generating the modified particle with the plurality of single-stranded nucleic acid agents immobilized thereto. To remove the reverse strand of all the nucleic acid agents attached to the particle in b4), a particle may be incubated with an alkaline solution thereby de-hybridizing the reverse strand from the forward strand. For example, the alkaline solution may comprise NaOH, Triton X-100, Sodium Dodecyl Sulfate (SDS), NaCl, Tris, EDTA, and/or Tween 20. Alternatively, or in addition, the particle may be treated with heating, or an enzyme (e.g., a helicase, or an exonuclease) to de-hybridize the reverse strand from the forward strand.

In some embodiments, b4) comprises de-hybridizing the reverse strand by incubation with an alkaline solution (such as a solution of NaOH).

The first single-stranded population may comprise a plurality of identical copies of single-stranded nucleic acid agents (e.g., the modified nucleic acid agent), each of which may be complementary to the reverse strand of the nucleic acid agents in the first double-stranded population of the template particle and may comprise at least one modified nucleotide. The second single-stranded population may comprise at least one single-stranded nucleic acid agent (e.g., the identification nucleic acid agent), which may be identical to the forward strand of the at least one nucleic acid agent comprised in the second double-stranded population of the template particle and may enable amplification of nucleic acid agents comprising the same nucleic acid sequence as the nucleic acid agent comprised in the first single-stranded population.

In the method for generating one or more modified particle, subsequent to b1), the particle may be encapsulated in a compartment with reagents necessary for performing at least b2). The reagents necessary for performing at least b2) may comprise one of more of the following: a nicking enzyme, a site-specific restriction enzyme, an exonuclease, a polymerase, and modified dNTPs. For example, after removing only the reverse strand of the at least one nucleic acid agent comprised in the second double-stranded population, the particle may be encapsulated into a compartment (e.g., a droplet) together with reagents necessary for removing a substantial part of the forward strands of nucleic acid agents in the first double-stranded population, for generating the nucleic acid strand complementary to the reverse strand of nucleic acid agents in the first double-stranded population, and/or for removing the reverse strand of all the nucleic acid agents attached to the particle of b4). For example, the reagents may comprise one of more of the following: a nicking enzyme, a site-specific restriction enzyme, an exonuclease, a polymerase, modified dNTPs, natural dNTPs, a suitable buffer, one or more salts, and a detergent. The particles may be contained in a solution, and the solution may be prepared such that each compartment (e.g., droplet) may only contain one or a few particles with nucleic acid agents immobilized thereto.

The method may further comprise c) amplifying the at least one identification nucleic acid agent to generate one or more of the template particles of a).

In some embodiments, the one or more template particles comprise two or more particles, and for any one of the two or more particles, a nucleic acid sequence of the nucleic acid agents immobilized thereto is different from that of the nucleic acid agents immobilized to at least one other particle. For example, the two or more particles may comprise multiple particles and the nucleic acid agents immobilized on one particle may be different from that immobilized to another particle. As another example, the two or more particles may comprise multiple particles and the nucleic acid sequence of the nucleic acid agents immobilized on one particle may be different from that of the nucleic acid agents immobilized on another particle.

In another aspect, the present disclosure provides a method for generating a pool comprising a plurality of modified members. The plurality of modified members may be a plurality of individual solid supports, each immobilized with a plurality of modified candidate nucleic acid agents. The method may comprise a) providing a pool comprising a plurality of kernel members, with each kernel member comprising a plurality of partially double-stranded candidate nucleic acid agents immobilized to a solid support. Each of the partially double-stranded candidate nucleic acid agents may comprise a forward strand and a reverse strand longer than the forward strand. The forward and reverse strand may associate with each other at least partially via base-paring. For example, the forward strand may, in its entire length, hybridize to the reverse strand, forming the partially double-stranded structure, while the rest portion of the reverse strand remains single-stranded.

The method may further comprise b) extending the forward strand of the partially double-stranded candidate nucleic acid agents by nucleotide polymerization using the corresponding reverse strand as a template. At least one modified nucleotide may be incorporated into the forward strand during extension to form modified candidate nucleic acid agents, thereby obtaining a pool of a plurality of modified members. Each modified member may comprise a plurality of the modified candidate nucleic acid agents immobilized to the solid support. The solid support comprised by the modified members may be the same as those comprised by the kernel members.

A nucleic acid sequence of the candidate nucleic acid agents comprised by any kernel member may be different from that of the candidate nucleic acid agents comprised by at least one other kernel member in the pool. For example, at least two kernel members in the same pool comprise nucleic acid agents having different nucleic acid sequences.

Sequence diversity of the candidate nucleic acid agents comprised by any kernel member in the pool may be less than that of the total candidate nucleic acid agents comprised by all the kernel members in the pool. Sequence diversity of the candidate nucleic acid agents comprised by any kernel member in the pool may be from 1 to 1000 (e.g., less than 900, less than 800, less than 700, less than 600, less than 500, less than 400, less than 300, less than 200, less than 100, less than 50, less than 40, less than 30, less than 20, less than 15, less than 10, less than 9, less than 8, less than 7, less than 6, less than 5, less than 4, less than 3, or less than 2). In some embodiments, any single kernel member only comprises nucleic acid agents having the same nucleic acid sequences.

Any one of the kernel members in the pool may comprise at least $1\times10^2$ (e.g., at least $1\times10^3$, at least $1\times10^4$, at least $1\times10^5$, at least $1\times10^6$, at least $1\times10^7$, at least $1\times10^8$, at least $1\times10^9$, at least $1\times10^{10}$, at least $1\times10^{11}$, at least $1\times10^{11}$ or more) copies of candidate nucleic acid agents having the same nucleic acid sequence.

A 5' end of the forward strand of the partially double-stranded candidate nucleic acid agents may be attached directly or indirectly to the solid support.

In some cases, the candidate nucleic acid agents (double-stranded, single-stranded or partially single-stranded) may be attached to the solid support via a linker. The linker may be cleavable or non-cleavable. In some embodiments, the linker may be an amino-modified nucleic acid primer.

In the method, for each modified candidate nucleic acid agent comprised by any modified member, a corresponding identification nucleic acid agent may be comprised by the same modified member. The identification nucleic acid agent may enable amplification of its corresponding modified candidate nucleic acid agent. The identification nucleic acid agent may be immobilized to the same solid support as its corresponding modified candidate nucleic acid agent.

In some embodiments, both the kernel member and the modified member comprise the identification nucleic acid agents. For example, the identification nucleic acid agent comprised by a modified member is also comprised by the kernel member employed to generate the corresponding modified candidate nucleic acid agent. In some embodiments, the identification nucleic acid agent comprised by the modified member and/or the kernel member is single-stranded.

For providing a pool comprising a plurality of kernel members, the method may comprise a1) providing a pool comprising a plurality of template members, with each template member comprising a plurality of double-stranded candidate nucleic acid agents immobilized to the solid support. Each double-stranded candidate nucleic acid agent may comprise a forward strand and a complementary reverse strand. A 5' end of the forward strand of the double-stranded candidate nucleic acid agents may be attached directly or indirectly to the solid support of the template members (such as via a cleavable or non-cleavable linker, e.g., a cleavable amino-modified nucleic acid primer).

For providing a pool comprising a plurality of kernel members, the method may further comprise, subsequent to a1), a2) treating the plurality of template members of a1) to remove a substantial part of the forward strand of the double-stranded candidate nucleic acid agents, with the corresponding reverse strand immobilized on the solid support, forming the reverse strand of the partially double-stranded candidate nucleic acid agents of the kernel members.

Sequence diversity of the double-stranded candidate nucleic acid agents comprised by any one of the template members in the pool may be less than that of the total double-stranded candidate nucleic acid agents comprised by all the template members in the pool. Sequence diversity of the double-stranded candidate nucleic acid agents comprised by any template member in the pool may be from 1 to 1000 (e.g., less than 900, less than 800, less than 700, less than 600, less than 500, less than 400, less than 300, less than 200, less than 100, less than 50, less than 40, less than 30, less than 20, less than 15, less than 10, less than 9, less than 8, less than 7, less than 6, less than 5, less than 4, less than 3, or less than 2). In some embodiments, any single template member only comprises nucleic acid agents having the same nucleic acid sequences.

Any one of the template members in the pool may comprise at least $1 \times 10^2$ (e.g., at least $1 \times 10^3$, at least $1 \times 10^4$, at least $1 \times 10^5$, at least $1 \times 10^6$, at least $1 \times 10^7$, at least $1 \times 10^8$, at least $1 \times 10^9$, at least $1 \times 10^{10}$, at least $1 \times 10^{11}$, at least $1 \times 10^{11}$ or more) copies of double-stranded candidate nucleic acid agents having the same nucleic acid sequence.

In some embodiments, the method may further comprise generating the template members comprising the plurality of double-stranded candidate nucleic acid agents by immobilizing the double-stranded candidate nucleic acid agents to the solid support. For example, a plurality of specifically designed forward primers may be immobilized to the solid support, and then, nucleic acid amplifications (e.g., PCR reaction, such as emulsion PCR) may be performed to immobilize the plurality of double-stranded candidate nucleic acid agents to the solid support.

For each double-stranded candidate nucleic acid agent comprised by any template member, a corresponding double-stranded identification nucleic acid agent may be comprised by the same template member. The double-stranded identification nucleic acid agent may comprise a forward strand and a complementary reverse strand, and wherein the double-stranded identification nucleic acid agent is different from its corresponding double-stranded candidate nucleic acid agent while enabling amplification thereof.

The double-stranded candidate nucleic acid agents and the double-stranded identification nucleic acid agents may be generated directly during the immobilization process, e.g., via the nucleic acid amplifications (e.g., PCR reaction, such as emulsion PCR), for example, by using different reverse primers for the emulsion PCR. For example, a reverse primer with (protected) nuclease-resistant phosphorothioated (PS) backbone may be used in the emulsion PCR to generate the double-stranded candidate nucleic acid agents, and simultaneously, a reverse primer without (unprotected) nuclease-resistant phosphorothioated (PS) backbone may be used in the emulsion PCR to generate the double-stranded identification nucleic acid agents. In some embodiments, the ratio of the protected and unprotected reverse primers in the PCR reaction mixture is predetermined to control the ratio between the double-stranded candidate nucleic acid agents and double-stranded identification nucleic acid agents.

In some embodiments, only one population of double-stranded nucleic acid agents may be present on the solid support after the immobilization process, e.g., after the nucleic acid amplifications (e.g., PCR reaction, such as emulsion PCR). Then, these template members comprising only one population of double-stranded nucleic acid agents may be further treated (e.g., partially digested) to generate the double-stranded candidate nucleic acid agents and the double-stranded identification nucleic acid agents.

In some embodiments, treating the plurality of template members of a1) to remove a substantial part of the forward strand of the double-stranded candidate nucleic acid agents comprises: a2-1) treating the plurality of template members of a1) to remove only the reverse strand of the double-stranded identification nucleic acid agent, and the forward strand of the double-stranded identification nucleic acid agent remains intact and immobilized on the solid support, forming the identification nucleic acid agent on the kernel member and/or the modified member. For example, a2-1) may comprise treating the template members obtained in a1) with a 5' to 3' exonuclease to remove only the reverse strand of the double-stranded identification nucleic acid agent.

For example, the reverse strand of the double-stranded candidate nucleic acid agents may be resistant to 5' to 3' exonuclease digestion. For example, a 5'end of the reverse strands of the double-stranded candidate nucleic acid agents may comprise modified nucleotides, such as phosphorothioated, Locked Nucleic Acids (LNA's), 2'-O-Methyl (2'OMe) modified nucleotides, 2'-O-(2-Methoxyethyl) (2'-O-MOE) modified nucleotides, 2' Fluoromodified nucleotides, or 5' Inverted Dideoxy-T. A reverse strand of the double-stranded identification nucleic acid agents may be susceptible to 5' to 3' exonuclease digestion. For example, the reverse strand of the double-stranded identification nucleic acid agents may not contain any modifications that render it resistant to 5' to 3' exonuclease digestion.

For example, the reverse strand of the double-stranded candidate nucleic acid agents may be resistant to 5' to 3' exonuclease digestion. In some embodiments, a 5' end of the reverse strand of the double-stranded candidate nucleic acid agents is phosphorothioated, and the reverse strand of the double-stranded identification nucleic acid agents is susceptible to 5' to 3' exonuclease digestion. Thus, by treating the template members obtained in a1) with a 5' to 3' exonuclease, only the reverse strand of the double-stranded identification nucleic acid agents may be removed.

In the method for generating the pool of modified members, removing only the reverse strand of the double-stranded identification nucleic acid agents may comprise treating the template members with a 5' to 3' exonuclease, such as a T5 exonuclease, an Exonuclease VIII, truncated, or a T7 exonuclease. For example, since the reverse strand of the double-stranded candidate nucleic acid agents may be resistant to 5' to 3' exonuclease digestion, while the reverse strand of double-stranded identification nucleic acid agents may be susceptible to 5' to 3' exonuclease digestion, treating the template members with a 5' to 3' exonuclease may only digest and remove the reverse strand of the double-stranded identification nucleic acid agents. The exonuclease digestion may be carried out at a temperature of at least about 15° C., at least about 20° C., at least about 25° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 41° C., at least about 42° C., at least about 43° C., at least about 44° C., at least about 45° C., at least about 46° C., at least about 47° C., at least about 48° C., at least about 49° C., or at least about 50° C.

In some embodiments, treating the plurality of template members of a1) to remove a substantial part of the forward strand of the double-stranded candidate nucleic acid agents further comprises: a2-2) treating the plurality of template members obtained in a2-1) so that a substantial part of the forward strand of the double-stranded candidate nucleic acid agents is removed, with the reverse strand of the double-stranded candidate nucleic acid agents immobilized on the solid support, forming the reverse strand of the partially double-stranded candidate nucleic acid agents of the kernel members. For example, a substantial part of the forward strand of the double-stranded candidate nucleic acid agents may be removed with an exonuclease.

In some cases, the reverse strand of the double-stranded candidate nucleic acid agents may be hybridized to a partial complement thereof attached to the solid support.

In some embodiments, a2-2) comprises treating the plurality of template members obtained in a2-1) with a site-specific nicking enzyme to generate nicked forward strand of the double-stranded candidate nucleic acid agents, which may be further treated with an exonuclease to remove a substantial part of the forward strand of the double-stranded candidate nucleic acid agents.

Any enzyme suitable for site-specifically generating a nicked forward strand may be employed, for example, a nicking enzyme may be selected from Nt.AlwI, Nt.BbvCI, Nt.BsmAI, Nt.BspQI, Nt.BstNBI, Nb.BbvCI, Nb.Bsml, Nb.BsrDI, Nb.BssSI, N b.BtsI, or a combination thereof. For example, after nicking, a nicked forward strand may be generated, rendering it susceptible to exonuclease digestion. The nicking reaction may be carried out at a temperature of at least about 30° C., at least about 35° C., at least about 40° C., at least about 45° C., at least about 46° C., at least about 47° C., at least about 48° C., at least about 49° C., at least about 50° C., at least about 51° C., at least about 52° C., at least about 53° C., at least about 54° C., at least about 55° C., at least about 56° C., at least about 57° C., at least about 58° C., at least about 59° C., at least about 60° C., at least about 65° C. or at least about 70° C.

For example, the nicking enzyme may recognize a specific site in the double-stranded candidate nucleic acid agents and hydrolyze only one of the two strands thereof (for example, hydrolyze the forward strand of the double-stranded candidate nucleic acid agents), to produce a "nicked" strand. Since the reverse strand of the double-stranded identification nucleic acid agents has been removed in the process of a1), the nicking enzyme could not recognize and hydrolyze (e.g., cut) the forward strand of the double-stranded identification nucleic acid agents (because it is single-stranded now, which cannot be recognized by the nicking enzyme). Thus, a nicked forward strand of the double-stranded candidate nucleic acid agents may be generated, which may then be digested by an exonuclease to remove a substantial part thereof, while the forward strand of the double-stranded identification nucleic acid agents may remain intact and attached to the solid support.

In some embodiments, a2-2) comprises treating the plurality of template members obtained in a2-1) with a site-specific restriction enzyme to generate double-stranded break of the double-stranded candidate nucleic acid agents, which may be further treated with an exonuclease to remove a substantial part of the forward strand of the double-stranded candidate nucleic acid agents.

Any enzyme suitable for site-specifically generating a double-stranded break of nucleic acid agents may be employed, for example, a site-specific restriction enzyme may be selected from NdeI, EcoRI, XhoI, HindIII, Ncos, AgeI, BamHI, KpnI, MfeI, SalI, or a combination thereof. For example, after treating the template members with a site-specific restriction enzyme, double-stranded breaks may be generated, rendering the forward strand of the double-stranded candidate nucleic acid agents susceptible to 5' to 3' exonuclease digestion. The site-specific restriction enzyme digestion may be carried out at a temperature of at least about 25° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 41° C., at least about 42° C., at least about 43° C., at least about 44° C., at least about 45° C., at least about 46° C., at least about 47° C., at least about 48° C., at least about 49° C., at least about 50° C., or at least about 55° C.

For example, the site-specific restriction enzyme may recognize a specific site in the double-stranded candidate nucleic acid agents and expose the 5' end of the forward strand of double-stranded candidate nucleic acid agents after generating a double-stranded break. Since the reverse strand of the double-stranded identification nucleic acid agents has been removed in the process of a1), the site-specific restriction enzyme could not recognize and digest (e.g., cut) the forward strand of the double-stranded identification nucleic acid agents (because it is single-stranded now, which cannot be recognized by the restriction enzyme). Thus, the forward strand of the double-stranded candidate nucleic acid agents may be cut with its 5' end exposed, which may then be digested by an exonuclease to remove a substantial part thereof, while the forward strand of the double-stranded identification nucleic acid agents may remain intact and attached to the solid support.

To remove a substantial part of the forward strands of double-stranded candidate nucleic acid agents, the template members may further be treated with an exonuclease. For example, after a template member is treated with a site-specific nicking enzyme or a site-specific restriction enzyme, an exonuclease (e.g., a 5' to 3'exonuclease) may be added to the reaction system or to the obtained template member. In some embodiments, after treating the template member with a nicking enzyme or a site-specific restriction enzyme, 5' ends of the forward strand of the double-stranded candidate nucleic acid agents may be exposed at the nicked or restriction enzyme recognition site and become susceptible to 5' to 3'exonuclease digestion, then, these forward strands may be digested and removed starting from the nicked site or restriction enzyme recognition site. The exonuclease digestion may be carried out at a temperature of at least about 15° C., at least about 20° C., at least about 25° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 41° C., at least about 42° C., at least about 43° C., at least about 44° C., at least about 45° C., at least about 46° C., at least about 47° C., at least about 48° C., at least about 49° C., or at least about 50° C.

In some embodiments, in a2), a remaining part of the forward strand of the double-stranded candidate nucleic acid agent is not removed and remains immobilized on the solid support, serving as the forward strand of the partially double-stranded candidate nucleic acid agent on the kernel members, and the reverse strand of the double-stranded candidate nucleic acid agent remains associated with the remaining part of the forward stand, serving as the reverse strand of the partially double-stranded candidate nucleic acid agent on the kernel members.

In some embodiments, the template member further comprises a plurality of single-stranded forward primers (e.g., immobilized forward primers complementary to the reverse strand of the double-stranded candidate nucleic acid agents) immobilized on the solid support. The single-stranded forward primers may be capable of associating with the reverse strand of the double-stranded candidate nucleic acid agent subsequent to removal of a substantial part of the forward strand of the double-stranded candidate nucleic acid agent.

For example, the single-stranded forward primers may comprise a sequence homologous or identical to a stretch of sequence at the 5' end of the forward strand of the double-stranded candidate nucleic acid agents, thereby being capable of hybridizing to a stretch of complementary sequence at or adjacent to the 3' end of the reverse strand of the double-stranded identification nucleic acid agents. A ratio between the combined number of double-stranded candidate nucleic acid agents and double-stranded identification nucleic acid agents immobilized to the solid support of a template member and that of the single-stranded forward primers immobilized to the same solid support of a template member is from about 10:1 to about 1:10. For example, such a ratio may be from about 2:1 to about 1:2, e.g., may be about 1:1. The hybridization may be carried out at a temperature of at least about 45° C., at least about 50° C., at least about 51° C., at least about 52° C., at least about 53° C., at least about 54° C., at least about 55° C., at least about 56° C., at least about 57° C., at least about 58° C., at least about 59° C., at least about 60° C., at least about 61° C., at least about 62° C., at least about 63° C., at least about 64° C., at least about 65° C., at least about 66° C., at least about 67° C., at least about 68° C., at least about 69° C., at least about 70° C., or at least about 75° C.

In some embodiments, the reverse strand of the double-stranded candidate nucleic acid agents detaches from the solid support and is re-attached by annealing to a partial complement thereof (e.g., the single-stranded forward primers) attached to the solid support. The annealing may occur at a temperature of at least about 45° C., at least about 50° C., at least about 51° C., at least about 52° C., at least about 53° C., at least about 54° C., at least about 55° C., at least about 56° C., at least about 57° C., at least about 58° C., at least about 59° C., at least about 60° C., at least about 61° C., at least about 62° C., at least about 63° C., at least about 64° C., at least about 65° C., at least about 66° C., at least about 67° C., at least about 68° C., at least about 69° C., at least about 70° C., or at least about 75° C.

In the method, the forward strand of the partially double-stranded candidate nucleic acid agents may be extended with a nucleic acid polymerase. Any suitable polymerase may be used, for example, a polymerase may be selected from Bst 3.0 DNA Polymerase, Bst 2.0 DNA Polymerase, Therminator™ DNA Polymerase, Deep VentR™ DNA Polymerase, Deep VentR™ (exo-) DNA Polymerase, OneTaq® Hot Start DNA Polymerase, Sulfolobus DNA Polymerase IV, phi29 DNA Polymerase, Klenow Fragment (3'→5' exo-), DNA Polymerase I, Large (Klenow) Fragment, KOD Hot Start DNA Polymerase, KOD Xtreme™ Hot Start DNA Polymerase, or a combination thereof. Nucleic acid strands synthesis (i.e., strand extension with incorporation of nucleotides) may be carried out at a temperature of at least about 45° C., at least about 50° C., at least about 51° C., at least about 52° C., at least about 53° C., at least about 54° C., at least about 55° C., at least about 56° C., at least about 57° C., at least about 58° C., at least about 59° C., at least about 60° C., at least about 61° C., at least about 62° C., at least about 63° C., at least about 64° C., at least about 65° C., at least about 66° C., at least about 67° C., at least about 68° C., at least about 69° C., at least about 70° C., or at least about 75° C.

After extending the forward strand of the partially double-stranded candidate nucleic acid agent, the reverse strands may be removed, and the modified candidate nucleic acid agents comprised by the modified members are then single-stranded. To remove the reverse strands of all the nucleic acid agents attached to the solid support, the members may be incubated with an alkaline solution thereby de-hybridizing the reverse strand from the forward strand. For example, the alkaline solution may comprise NaOH, Triton X-100, Sodium Dodecyl Sulfate (SDS), NaCl, Tris, EDTA, and/or Tween 20. Alternatively, or in addition, the members may be treated with heating, or an enzyme (e.g., a helicase, or an exonuclease) to de-hybridize the reverse strand from the forward strand. In some embodiments, the reverse strands are de-hybiridized by incubation with an alkaline solution (such as a solution of NaOH).

In the method for generating the pool of modified members, subsequent to a2-1), the member may be encapsulated in a compartment. The compartment may further comprise one of more of the following: a nicking enzyme, a site-specific restriction enzyme, an exonuclease, a polymerase, and modified dNTPs. For example, after removing only the reverse strand of the double-stranded identification nucleic acid agent, the member may be encapsulated into a compartment (e.g., a droplet) together with reagents necessary for removing a substantial part of the forward strands of the double-stranded candidate nucleic acid agents, for generating the nucleic acid strand complementary to the reverse strand of the double-stranded candidate nucleic acid agents, and/or for removing the reverse strand of all the nucleic acid agents attached to the solid support after strand extension. For example, the reagents may comprise one of more of the following: a nicking enzyme, a site-specific restriction enzyme, an exonuclease, a polymerase, modified dNTPs, natural dNTPs, a suitable buffer, one or more salts, and a detergent. The members may be contained in a solution, and the solution may be prepared such that each compartment (e.g., droplet) may only contain one or a few members with nucleic acid agents immobilized thereto.

The at least one nucleic acid agent comprised in the second single-stranded population (e.g., the identification nucleic acid agent comprised by the kernel member or the modified member) may be a unique identifier for the nucleic acid agent comprised in the first single-stranded population (e.g., the modified candidate nucleic acid agent, such as those comprised by the modified members). The at least one nucleic acid agent comprised in the second single-stranded population (e.g., the identification nucleic acid agent) may contain nucleic acid sequence information of the nucleic acid agent comprised in the first single-stranded population (e.g., the candidate nucleic acid agents). The nucleic acid agents of the first single-stranded population (e.g., the modified candidate nucleic acid agents, such as those comprised by the modified members) may not be capable of functioning directly as a template in a nucleic acid amplification reaction.

The identification nucleic acid agent (double-stranded or single-stranded, such as the at least one single-stranded nucleic acid agent of the second single-stranded population, or those comprised by a member from a pool according to the present application) may be capable of being amplified in a nucleic acid amplification reaction and/or being sequenced.

The identification nucleic acid agent (such as the at least one single-stranded nucleic acid agent of the second single-stranded population) may comprise the same nucleic acid sequence as that comprised in the modified candidate nucleic acid agent (e.g., the nucleic acid agent of the first single-stranded population, such as those comprised by the modified members). For example, the identification nucleic acid agent (e.g., the at least one nucleic acid agent comprised in the second single-stranded population) may be the same as the modified candidate nucleic acid agent (e.g., the nucleic acid agent of the first single-stranded population), except that the identification nucleic acid agent does not comprise any modified nucleotide while the modified candidate nucleic acid agent comprises at least one modified nucleotide.

The identification nucleic acid agent (double-stranded or single-stranded, such as the at least one single-stranded nucleic acid agent of the second single-stranded population) may consist essentially of natural nucleotides. For example, the identification nucleic acid agent (e.g., the at least one single-stranded nucleic acid agent of the second single-stranded population) may consist of natural DNA.

In the modified particles or modified members generated, the nucleic acid agents of the first single-stranded population or the modified candidate nucleic acid agents may be capable of specifically binding to a target. The target may be a protein target. The modified candidate nucleic acid agents or the nucleic acid agent comprised in the first single-stranded population may be an aptamer.

The target may be a polynucleotide, a polypeptide, a nucleic acid molecule, a protein target, a small molecule target, a whole cell, a cellular component, a liposome or a combination thereof. Suitable target may include, for example, small molecule s (e.g., organic dyes), amino acids, carbohydrates, lipids, aminoglycosides, antibiotics, peptides, proteins, post-translational modification, nucleic acids, virus, whole cells and cellular components. Small molecule targets of interest generally have a molecular weight of about 800 Daltons or less. Protein targets of interest may include, for example, cell surface receptors, signal transduction factors, and hormones. Cellular targets of interest may include, for example, mammalian cells, particularly human cells; stem cells; tumor cells and bacterial cells. In some embodiments, two or more types of targets (such as protein targets having different amino acid sequences) may be simultaneously tested against a single library of candidate nucleic acid agents or candidate aptamer sequences. In some embodiments, a target molecule or a molecule associated with a target molecule, e.g., via a binding interaction, may be detectably labeled.

Suitable labels may include radioactive isotopes, fluorescers, chemiluminescers, chromophores, enzymes, enzyme substrates, enzyme cofactors, enzyme inhibitors, dyes, metal ions, metal sols, ligands (e.g., biotin, avidin, streptavidin or haptens), affinity tags and the like.

Exemplary affinity tags suitable for use may include, but are not limited to, a monoclonal antibody for the target molecule, a polyclonal antibody for the target molecule, a fluorescent antibody, a biotinylated antibody, a monocytic adaptor protein (MONA) binding peptide, a T7 binding peptide, a streptavidin binding peptide, a polyhistidine tract, protein A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), or other antigenic epitope or binding domain. See, in general, Ford et al., Protein Expression and Purification 2:95 (1991). DNA molecule s encoding affinity tags are available from commercial suppliers (e.g., Pharmacia Biotech, Piscataway, N.J.).

Any fluorescent polypeptide (also referred to herein as a fluorescent label) may be suitable for use as a detectable label. A suitable fluorescent polypeptide will be one that will readily provide a detectable signal that can be assessed qualitatively (positive/negative) and quantitatively (comparative degree of fluorescence). Exemplary fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof. Further suitable fluorescent polypeptides, as well as specific examples of those listed herein, are provided in the art and are well known.

Biotin-based labels may also be employed. Biotinylation agents that may be used include, for example, amine-reactive and thiol-reactive agents, for the biotinylation of proteins, nucleic acids, carbohydrates, carboxylic acids; see, e.g., chapter 4, Molecular Probes Catalog, Haugland, 6th Ed. 1996, hereby incorporated by reference. A biotinylated substrate can be detected by binding of a detectably labeled biotin binding partner, such as avidin or streptavidin. Similarly, a large number of haptenylation reagents are also known.

In any aspect of the present disclosure, the single-stranded nucleic acid agent of the first single-stranded population or the modified candidate nucleic acid agent may be capable of specifically binding to a target with a Kd of from about 1 pM to about 100 μM, at least about 90 μM, at least about 80 μM, at least about 70 μM, at least about 60 μM, at least about 50 μM, at least about 40 μM, at least about 30 μM, at least about 20 μM, at least about 10 μM, at least about 1 μM, at least about 500 nM, at least about 400 nM, at least about 300 nM, at least about 200 nM, or at least about 100 nM, such as from about 1 pM to about 10 nM. For example, the single-stranded nucleic acid agent in the first single-stranded population or the modified candidate nucleic acid agent may be capable of specifically binding to a target with a Kd of at least about 90 nM, at least about 80 nM, at least about 70 nM, at least about 60 nM, at least about 50 nM, at least about 40 nM, at least about 30 nM, at least about 20 nM, at least about 10 nM, at least about 8 nM, at least about 6 nM, at least about 4 nM, at least about 2 nM, at least about 1 nM, at least about 900 pM, at least about 800 pM, at least about 700 pM, at least about 600 pM, at least about 500 pM, at least about 400 pM, at least about 300 pM, at least about 200 pM, at least about 100 pM, at least about 90 pM, at least about 80 pM, at least about 70 pM, at least about 60 pM, at least about 50 pM, at least about 40 pM, at least about 30 pM, at least about 20 pM, at least about 10 pM, at least about 5 pM, at least about 1 pM, or greater.

In some embodiments, the modified candidate nucleic acid agent or the nucleic acid agent comprised in the first single-stranded population consists essentially of modified nucleotides.

The modified nucleotide may comprise one or more chemical modifications at one or more positions independently selected from the group consisting of a ribose position, a deoxyribose position, a phosphate position, and a base position. For example, the chemical modifications are independently selected from the group consisting of a 2'position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, methylation, a 3'cap, and a 5' cap.

The 5-position modified pyrimidine may be selected from the group consisting of 5-Carboxy-2'-deoxyuridine (5-Carboxy-dU), 5-Aminoallyl-2'-deoxyuridine (5-AA-dU), 5-[(3-Indolyl)propionamide-N-allyl]-2'-deoxyuridine (Tryptamino-dU), 5-Carboxy-2'-deoxycytidine (5-Carboxy-dC), 5-Aminoallyl-2'-deoxycytidine (5-AA-dC), Biotin-16-Aminoallyl-2'-deoxycytidine (Biotin-16-AA-dC), 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

In the method for generating one or more modified particle or for generating the pool of modified members, a ratio of nucleic acid agents comprised in the first double-stranded population (e.g., double-stranded candidate nucleic acid agents) to that comprised in the second double-stranded population (e.g., double-stranded identification nucleic acid agents) may be from about $10^{10}$:1 to about 1:1. For example, in a ratio of from about $10^9$:1 to about 1:1, from about $10^8$:1 to about 1:1, from about $10^7$:1 to about 1:1, from about $10^6$:1 to about 1:1, from about $10^5$:1 to about 1:1, from about $10^4$:1 to about 1:1, from about $10^3$:1 to about 1:1, from about 100:1 to about 1:1, from about 90:1 to about 1:1, from about 80:1 to about 1:1, from about 70:1 to about 1:1, from about 60:1 to about 1:1, from about 50:1 to about 1:1, from about 40:1 to about 1:1, from about 30:1 to about 1:1, from about 20:1 to about 1:1, from about 15:1 to about 1:1, from about 10:1 to about 1:1, from about 9:1 to about 1:1, from about 8:1 to about 1:1, from about 7:1 to about 1:1, from about 6:1 to about 1:1, from about 5:1 to about 1:1, from about 4:1 to about 1:1, from about 3:1 to about 1:1, or from about 2:1 to about 1:1. In some embodiment, the nucleic acid agents comprised in the first double-stranded population (e.g., double-stranded candidate nucleic acid agents) to that comprised in the second double-stranded population (e.g., double-stranded identification nucleic acid agents) may be in a ratio of no more than 1:10, no more than about 1:100, no more than about 1:1000, or no more than about 1:10000.

In some embodiments, the nucleic acid agent comprised in the first single-stranded population or the modified candidate nucleic acid agents may exhibit a desired property, and an identity of such nucleic acid agents having the desired property may be determined from the at least one single-stranded nucleic acid agent of the second single-stranded population or the identification nucleic acid agent. For example, an identity of the nucleic acid agent having the desired property (e.g., the modified candidate nucleic acid agent) may be determined through sequencing the at least one single-stranded nucleic acid agent of the second single-stranded population or the identification nucleic acid agent.

In another aspect, the present disclosure provides a use of a particle (a library of particles, or a pool of members) according to the present disclosure in the manufacture of a reagent for identifying a nucleic acid agent having a desired property.

In the present disclosure, one or more of the nucleic acid agents immobilized to a particle or a solid support of the present disclosure may comprise a molecule conjugated thereto. For example, the molecule conjugated may be selected from the group consisting of a protein (such as an antibody), a small molecule, a fluorophore, a peptide, a therapeutically active component (e.g., a drug), a polymer (e.g., polyethylene glycol, poly(lactic-co-glycolic acid), or hydrogel), and an siRNA.

In the present disclosure, a particle or a solid support may be non-magnetic, magnetic or paramagnetic. For example, the particle or solid support may be a bead. A variety of suitable particles or solid supports may be used for generating a particle or a member of the present disclosure. Such particles or solid supports may be sized to have at least one dimension, e.g., diameter, of from about 50 nm to about 100 µm. For example, in some embodiments, a suitable particle or solid support has at least one dimension of from about 50 nm to about 1 µm, e.g., from about 50 nm to about 500 nm, or from about 50 nm to about 100 nm. In other embodiments, a suitable particle or solid support has at least one dimension of from about 500 nm to about 100 µm, e.g., from about 1 µm to about 100 µm, or from about 50 µm to about 100 µm. Suitable particles or solid supports may be generally spherical or may have any other suitable shape. In some cases, a solid support may be a flat surface, an area in a plate or a spot in an array.

A particle or a solid support according to the present disclosure may be made from a variety of suitable materials. For example, magnetic particles or solid supports may be employed in the compositions and/or methods of the present disclosure. Suitable magnetic particles or solid supports may include, for example, magnetic beads or other small objects made from a magnetic material such as a ferromagnetic material, a paramagnetic material, or a super paramagnetic material. Magnetic particles may include, e.g., iron oxide ($Fe_2O_3$ and/or $Fe_3O_4$). Additional particles or solid supports of interest may include polymer based materials, e.g., polymer based solid supports or particles. For example, polystyrene particles may be employed. In addition, ceramic particles may be employed.

A particle or solid support according to the present disclosure may include or be coated with a material which facilitates coupling of the particles or solid supports to a nucleic acid agent (e.g., to an aptamer sequence). Examples of coatings may include polymer shells, glasses, ceramics, gels, etc. In some embodiments, the coatings include or are themselves coated with a material that facilitates coupling or physical association of the particles or solid supports with a nucleic acid agent (e.g., an aptamer). For example, particles or solid supports with exposed carboxylic acid groups may be used for attachment to an amino-modified nucleotide agent, such as an aptamer. In some embodiments, a streptavidin coated particle or solid support may be used for attachment to a 5' biotinylated nucleic acid agent, such as an aptamer.

In the present disclosure, a particle or a solid support may comprise from about 10 to about $10^{10}$ double-stranded and/or single-stranded nucleic acid agents, e.g., at least about $10^2$ nucleic acid agents, at least about $10^3$ nucleic acid agents, at least about $10^4$ nucleic acid agents, at least about $10^5$ nucleic acid agents, at least about $10^6$ nucleic acid agents, at least about $10^7$ nucleic acid agents, at least about $10^8$ nucleic acid agents, at least about $10^9$ nucleic acid agents.

The nucleic acid agents immobilized to the particle or solid support may comprise single-stranded nucleic acid agents, double-stranded nucleic acid agents, or a combination thereof.

In some embodiments, the particle or a member in a pool may comprise 3, 4, 5, 6, 7, 8, or more different populations of nucleic acid agents. For example, the particle or member in a pool may comprise an even number of populations immobilized thereto, and these populations are matched and grouped into a plurality of pairs. For each pair, a first population may comprise a plurality of identical copies of a single species of nucleic acid agents (e.g., candidate nucleic acid agents), and the other population may comprise at least one nucleic acid agent enabling amplification of a nucleic acid in said first population (e.g., a corresponding identification nucleic acid agents).

The present disclosure also relates to the following embodiments.

1. A particle comprising a plurality of nucleic acid agents immobilized thereto, wherein: said plurality of nucleic acid agents comprise a first population and a second population; nucleic acid agents in said first population are different from that in said second population; said first population comprises a plurality of identical copies of a single species of nucleic acid agent; said second population comprises at least one nucleic acid agent, and said at least one nucleic acid agent enables amplification of nucleic acid agents comprising the same nucleic acid sequence as the nucleic acid agent comprised in said first population.

2. The particle according to embodiment 1, wherein said at least one nucleic acid agent comprised in said second population contains nucleic acid sequence information of the nucleic acid agent in said first population.

3. The particle according to embodiment 1 or 2, wherein said at least one nucleic acid agent comprised in said second population is a unique identifier for said nucleic acid agent comprised in said first population.

4. The particle according to any one of embodiments 1-3, wherein said single species of nucleic acid agent comprised in said first population is capable of specifically binding to a target.

5. The particle according to embodiment 4, wherein said target is a protein target.

6. The particle according to any one of embodiments 1-5, wherein said single species of nucleic acid agent comprised in said first population is an aptamer.

7. The particle according to any one of embodiments 1-6, wherein each of said nucleic acid agent comprised in said first population comprises at least one modified nucleotide.

8. The particle according to embodiment 7, wherein each of said nucleic acid agent comprised in said first population consists essentially of modified nucleotides.

9. The particle according to any one of embodiments 7-8, wherein none of said nucleic acid agent comprised in said first population is capable of functioning directly as a template in a nucleic acid amplification reaction.

10. The particle according to any one of embodiments 7-9, wherein said modified nucleotide comprises a chemical substitution or modification at one or more positions independently selected from the group consisting of a ribose position, a deoxyribose position, a phosphate position, and a base position.

11. The particle according to any one of embodiments 7-10, wherein said modified nucleotide comprises one or more modifications independently selected from the group consisting of a 2'-position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, a methylation, a 3'cap, and a 5'cap.

12. The particle according to embodiment 11, wherein said 5-position modified pyrimidine is selected from the group consisting of 5-Carboxy-2'-deoxyuridine, 5-Aminoallyl-2'-deoxyuridine, 5-[(3-Indolyl)propionamide-N-allyl]-2'-deoxyuridine, 5-Carboxy-2'-deoxycytidine, 5-Aminoallyl-2'-deoxycytidine, Biotin-16-Aminoallyl-2'-deoxycytidine, 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

13. The particle according to any one of embodiments 1-12, wherein said second population comprises a plurality of identical copies of said at least one nucleic acid agent.

14. The particle according to any one of embodiments 1-13, wherein said at least one nucleic acid agent comprised in said second population is capable of being amplified in a nucleic acid amplification reaction and/or being sequenced.

15. The particle according to any one of embodiments 1-14, wherein said at least one nucleic acid agent comprised in said second population comprises the same nucleic acid sequence as that of the nucleic acid agent in said first population.

16. The particle according to embodiment 15, wherein said at least one nucleic acid agent comprised in said second population is the same as the nucleic acid agent in said first population, except that said at least one nucleic acid agent comprised in said second population does not comprise any modified nucleotide while the nucleic acid agent in said first population comprises at least one modified nucleotide.

17. The particle according to any one of embodiments 1-16, wherein said at least one nucleic acid agent comprised in said second population consists essentially of natural nucleotides.

18. The particle according to embodiment 17, wherein said at least one nucleic acid agent comprised in said second population consists of natural DNA.

19. The particle according to any one of embodiments 1-18, wherein a ratio of nucleic acid agents comprised in said first population to that comprised in said second population is from about $10^{10}:1$ to about 1:1.

20. The particle according to any one of embodiments 1-19, wherein one or more of the nucleic acid agents immobilized to said particle comprises a molecule conjugated thereto.

21. The particle according to embodiment 20, wherein said molecule is selected from the group consisting of a small molecule, a fluorophore, a peptide, a therapeutically active component and a siRNA.

22. The particle according to any one of embodiments 1-21, wherein said particle is non-magnetic, magnetic or paramagnetic.

23. The particle according to any one of embodiments 1-22, wherein said particle has at least one dimension of from about 50 nm to about 100 µm.

24. The particle according to any one of embodiments 1-23, wherein said plurality of nucleic acid agents immobilized thereto comprises from about 10 to about $10^{10}$ nucleic acid agents.

25. The particle according to any one of embodiments 4-24, wherein said nucleic acid agent comprised in said first population is capable of specifically binding to a target with a Kd of from about 1 pM to about 100 µM.

26. The particle according to any one of embodiments 1-25, wherein said nucleic acid agents immobilized thereto comprises single-stranded nucleic acid agents, double-stranded nucleic acid agents, or a combination thereof.

27. A particle library, wherein said library comprises from about 10 to about $10^{15}$ different particles as defined in any one of embodiments 1-26.

28. The library according to embodiment 27, wherein said library is an enriched particle pool.

29. The library according to any one of embodiments 27-28, wherein for any particle comprised in said library, a nucleic acid sequence of the nucleic acid agents immobilized thereto is different from that of the nucleic acid agents immobilized to at least one other particle.

30. A method for identifying a nucleic acid agent having a desired property from a mixture of candidate nucleic acid agents, the method comprising: a) obtaining one or more particles as defined in any one of embodiments 1-26 or a particle library as defined in any one o embodiments 27-29; b) exposing said particles to a target, thereby determining a presence or absence of said desired property; c) isolating one or more particles having immobilized thereto a nucleic acid agent having the desired property; and d) identifying said nucleic acid agent having the desired property from the isolated particles.

31. The method of embodiment 30, wherein said target is a protein target, a small molecule target, a whole cell, a cellular component or a liposome.

32. The method according to any one of embodiments 30-31, wherein said desired property is a target binding activity or a target-binding induced activity.

33. The method of embodiment 32, wherein said target binding activity is affinity, specificity or bi-specificity.

34. The method of embodiment 32, wherein the target-binding induced activity is a catalytic activity, an inhibition activity, an activation activity, a structure switching activity, and/or a cooperative activity.

35. The method according to any one of embodiments 30-34, wherein said desired property is a property of the nucleic acid agent of the first population.

36. The method according to any one of embodiments 30-35, wherein an identity of said nucleic acid agent having the desired property is determined from said at least one nucleic acid agent comprised in said second population.

37. The method according to embodiment 36, wherein an identity of said nucleic acid agent having the desired property is determined through sequencing the at least one nucleic acid agent comprised in said second population.

38. A method for generating a particle as defined in any one of embodiments 1-26 or a particle library as defined in any one of embodiments 27-29.

39. A method for generating one or more modified particle with nucleic acid agents immobilized thereto, the method comprising: a) obtaining one or more template particles, each with a plurality of double-stranded nucleic acid agents immobilized thereto, each of said double-stranded nucleic acid agent comprises a forward strand and a reverse strand, wherein for each particle: said plurality of double-stranded nucleic acid agents comprise a first double-stranded population and a second double-stranded population, the nucleic acid agents comprised in said first double-stranded population are different from that in said second double-stranded population; b) treating the template particle obtained in a) so that for each particle: at least one modified nucleic acid agent is derived from said first double-stranded population, said at least one modified nucleic acid agent contains at least one modified nucleotide and is not capable of functioning directly as a template in a nucleic acid amplification reaction; and at least one identification nucleic acid agent is derived from said second double-stranded population, said at least one identification nucleic acid agent enables amplification of nucleic acid agents comprising the same nucleic acid sequence as said modified nucleic acid agent derived from said first double-stranded population.

40. The method according to embodiment 39, wherein said first double-stranded population comprises a plurality of identical copies of a single species of nucleic acid agent.

41. The method according to any one of embodiments 39-40, wherein for each of the plurality of double-stranded nucleic acid agents, said reverse strand is complementary to said forward strand, and said forward strand is attached to said particle.

42. The method according to any one of embodiments 39-41, further comprising c) amplifying said at least one identification nucleic acid agent to generate one or more said template particles of a).

43. The method according to any one of embodiments 39-42, wherein said one or more template particles comprise two or more particles, and for any one of the two or more particles, a nucleic acid sequence of the nucleic acid agents immobilized thereto is different from that of the nucleic acid agents immobilized to at least one other particle.

44. The method according to any one of embodiments 39-43, wherein b) comprises: b1) treating the template particle obtained in a) so that only the reverse strand of the at least one nucleic acid agent comprised in the second double-stranded population is removed.

45. The method according to embodiment 44, wherein b) further comprises b2) treating the particle obtained in b1) so that a substantial part of the forward strand of said nucleic acid agents in said first double-stranded population is removed.

46. The method according to embodiment 45, wherein in b2), the reverse strand of said nucleic acid agents of said first double-stranded population is hybridized to a partial complement thereof attached to the particle.

47. The method according to any one of embodiments 45-46, wherein b) further comprises b3) incorporating nucleotides to generate nucleic acid strand complementary to the reverse strand of said nucleic acid agents of the first double-stranded population.

48. The method according to embodiment 47, wherein b3) comprises extending said partial complement on the particle of b2) by incorporating nucleotides to generate nucleic acid strand complementary to said reverse strand of the nucleic acid agents of said first double-stranded population.

49. The method according to any one of embodiments 47-48, wherein the incorporated nucleotides comprise at least one modified nucleotide.

50. The method according to any one of embodiments 47-49, wherein b) further comprises b4) generating a modified particle with a plurality of single-stranded nucleic acid agents immobilized thereto, said plurality of single-stranded nucleic acid agents comprise a first single-stranded population and a second single-stranded population; said at least one modified nucleic acid agent is comprised in said first single-stranded population and said at least one identification nucleic acid agent is comprised in said second single-stranded population.

51. The method according to embodiment 50, wherein b4) comprises removing the reverse strand of all the nucleic acid agents attached to the particle obtained in b3), thereby generating the modified particle with a plurality of single-stranded nucleic acid agents immobilized thereto.

52. The method according to any one of embodiments 39-51, wherein said modified nucleic acid agent comprises a plurality of identical copies of single-stranded nucleic acids, each of which is complementary to the reverse strand of said nucleic acid agents in said first double-stranded population and comprises at least one modified nucleotide.

53. The method according to any one of embodiments 39-52, wherein said identification nucleic acid agent comprises at least one single-stranded nucleic acid agent, which is identical to the forward strand of said at least one nucleic acid agent comprised in said second double-stranded population and enables amplification of nucleic acid agents comprising the same nucleic acid sequence as the modified nucleic acid agent.

54. The method according to any one of embodiments 45-53, wherein in b2), the forward strand of said at least one nucleic acid agent of said second double-stranded population remains intact and attached to the particle.

55. The method according to any one of embodiments 39-54, wherein the reverse strand of said nucleic acid agents comprised in said first double-stranded population is resistant to 5' to 3' exonuclease digestion.

56. The method according to any one of embodiments 39-55, wherein a 5' end of the reverse strand of said nucleic acid agents in said first double-stranded population is phosphorothioated.

57. The method according to any one of embodiments 39-56, wherein the reverse strand of said at least one nucleic acid agent comprised in said second double-stranded population is susceptible to 5' to 3' exonuclease digestion.

58. The method according to any one of embodiments 44-57, wherein b1) comprises treating the particle obtained in a) with a 5' to 3' exonuclease thereby only removing the reverse strand of said at least one nucleic acid agent comprised in said second double-stranded population.

59. The method according to any one of embodiments 45-58, wherein b2) comprises treating the particle obtained in b1) with a site-specific nicking enzyme to generate nicked forward strand of nucleic acid agents comprised in said first double-stranded population.

60. The method according to any one of embodiments 45-58, wherein b2) comprises treating the particle obtained in b1) with a site-specific restriction enzyme to generate double-stranded break of nucleic acid agents comprised in said first double-stranded population.

61. The method according to any one of embodiments 45-60, wherein b2) comprises removing a substantial part of the forward strand of said nucleic acid agents in said first double-stranded population with an exonuclease.

62. The method according to any one of embodiments 45-59 or embodiment 61, wherein in b2), a remaining part of the forward strand of said nucleic acid agents in said first double-stranded population is not removed and remains attached to the particle, serving as said partial complement, and the reverse strand of the nucleic acid agents in the first double-stranded population remains hybridized to said remaining part of said forward strand of the nucleic acid agents in the first double-stranded population.

63. The method according to any one of embodiments 45-62, wherein said template particle in a) further comprises a third population containing a plurality of single-stranded nucleic acid agents attached thereto, said plurality of single-stranded nucleic acid agents of said third population serve as said partial complement in b2) and hybridize to said reverse strand of said nucleic acid agents of the first double-stranded population subsequent to removal of a substantial part of the forward strand of nucleic acid agents in the first double-stranded population.

64. The method according to any one of embodiments 47-63, wherein b3) comprises incorporating nucleotides with a nucleic acid polymerase.

65. The method according to any one of embodiments 50-64, wherein b4) comprises de-hybridizing said reverse strand by incubation with an alkaline solution.

66. The method according to any one of embodiments 45-65, wherein subsequent to b1), said particle is encapsulated in a compartment with reagents necessary for performing at least b2).

67. The method according to embodiment 66, wherein said reagents necessary for performing at least b2) comprises one or more of the following: a nicking enzyme, a site-specific restriction enzyme, an exonuclease, a polymerase, and modified dNTPs.

68. The method according to any one of embodiments 39-67, wherein said modified nucleic acid agent is capable of specifically binding to a target.

69. The method according to embodiment 68, wherein said target is a protein target.

70. The method according to any one of embodiments 39-69, wherein said at least one identification nucleic acid agent contains nucleic acid sequence information of said modified nucleic acid agent.

71. The method according to any one of embodiments 39-70, wherein said at least one identification nucleic acid agent is a unique identifier for the modified nucleic acid agent.

72. The method according to any one of embodiments 39-71, wherein said modified nucleic acid agent is an aptamer.

73. The method according to any one of embodiments 39-72, wherein said modified nucleic acid agent consists essentially of modified nucleotides.

74. The method according to any one of embodiments 39-73, wherein said modified nucleotide comprises a chemical substitution or modification at one or more positions independently selected from the group consisting of a ribose position, a deoxyribose position, a phosphate position, and a base position.

75. The method according to any one of embodiments 39-74, wherein said modified nucleotide comprises one or more modifications independently selected from the group consisting of a 2'-position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, a methylation, a 3' cap, and a 5' cap.

76. The method according to embodiment 75, wherein said 5-position modified pyrimidine is selected from the group consisting of 5-Carboxy-2'-deoxyuridine, 5-Aminoallyl-2'-deoxyuridine, 5-[(3-Indolyl)propionamide-N-allyl]-2'-deoxyuridine, 5-Carboxy-2'-deoxycytidine, 5-Aminoallyl-2'-deoxycytidine, Biotin-16-Aminoallyl-2'-deoxycytidine, 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

77. The method according to any one of embodiments 39-76, wherein said second double-stranded population comprises a plurality of identical copies of said at least one nucleic acid agent.

78. The method according to any one of embodiments 39-77, wherein said identification nucleic acid agent is capable of being amplified in a nucleic acid amplification reaction and/or being sequenced.

79. The method according to any one of embodiments 39-78, wherein said at least one nucleic acid agent comprised in said second double-stranded population comprises the same nucleic acid sequence as that comprised in said nucleic acid agent of said first double-stranded population.

80. The method according to any one of embodiments 39-79, wherein said identification nucleic acid agent comprises the same nucleic acid sequence as that comprised in said modified nucleic acid agent.

81. The method according to embodiment 80, wherein said at least one identification nucleic acid agent comprises the same nucleic acid sequence as that comprised in said modified nucleic acid agent, except that said at least one identification nucleic acid agent does not comprise any modified nucleotide while said at least one modified nucleic acid agent comprises at least one modified nucleotide.

82. The method according to any one of embodiments 39-81, wherein said at least one identification nucleic acid agent consists essentially of natural nucleotides.

83. The method according to embodiment 82, wherein said at least one identification nucleic acid agent consists of natural DNA.

84. The method according to any one of embodiments 39-83, wherein a ratio of nucleic acid agents comprised in said first double-stranded population to that comprised in said second double-stranded population is from about $10^{10}$:1 to about 1:1.

85. The method according to any one of embodiments 39-84, wherein one or more of the nucleic acid agents immobilized to said particle comprises a molecule conjugated thereto.

86. The method according to embodiment 85, wherein said molecule is selected from the group consisting of a small molecule, a fluorophore, a peptide, a therapeutically active component and an siRNA.

87. The method according to any one of embodiments 39-86, wherein said particle is non-magnetic, magnetic or paramagnetic.

88. The method according to any one of embodiments 39-87, wherein said particle has at least one dimension of from about 50 nm to about 100 μm.

89. The method according to any one of embodiments 39-88, wherein said plurality of nucleic acid agents immobilized to said particle comprises from about 10 to about $10^{10}$ nucleic acid agents.

90. The method according to any one of embodiments 39-89, wherein said modified nucleic acid agent is capable of specifically binding to a target with a Kd of from about 1 pM to about 100 μM.

91. The method according to any one of embodiments 39-90, further comprising immobilizing a plurality of double-stranded nucleic acid agents to said particle prior to a) to generate said template particle.

92. The method according to embodiment 91, wherein said immobilizing comprises using emulsion PCR.

93. The method according to any one of embodiments 39-92, wherein said at least one nucleic acid agent comprised in said second double-stranded population contains nucleic acid sequence information of the nucleic acid agent in said first double-stranded population.

94. Use of a particle according to any one of embodiments 1-26 or a particle library according to any one of embodiments 27-29 in the manufacture of a reagent for identifying a nucleic acid agent having a desired property.

95. A method for generating a pool comprising a plurality of modified members, the method comprising: a) providing a pool comprising a plurality of kernel members, with each kernel member comprising a plurality of partially double-stranded candidate nucleic acid agents immobilized to a solid support, and each of said partially double-stranded candidate nucleic acid agents comprises a forward strand and a reverse strand longer than said forward strand, wherein said forward and reverse strand associate with each other at least partially via base-paring; and b) extending said forward strand of the partially double-stranded candidate nucleic acid agents by nucleotide polymerization using the corresponding reverse strand as a template, and at least one modified nucleotide is incorporated into said forward strand during extension to form modified candidate nucleic acid agents, thereby obtaining a pool of a plurality of modified members, with each modified member comprising a plurality of said modified candidate nucleic acid agents immobilized to said solid support; wherein a nucleic acid sequence of the candidate nucleic acid agents comprised by any kernel member is different from that of the candidate nucleic acid agents comprised by at least one other kernel member in the pool.

96. The method according to embodiment 95, wherein sequence diversity of the candidate nucleic acid agents comprised by any kernel member in the pool is less than that of the total candidate nucleic acid agents comprised by all the kernel members in the pool.

97. The method according to any one of embodiments 95-96, wherein any one of the kernel members in the pool comprises at least $1 \times 10^2$ copies of candidate nucleic acid agents having the same nucleic acid sequence.

98. The method according to any one of embodiments 95-97, wherein sequence diversity of the candidate nucleic acid agents comprised by any kernel member in the pool is from 1 to 1000.

99. The method according to any one of embodiments 95-98, wherein a 5' end of said forward strand of the partially double-stranded candidate nucleic acid agents is attached directly or indirectly to the solid support.

100. The method according to any one of embodiments 95-99, wherein said modified candidate nucleic acid agent is not capable of functioning directly as a template in a nucleic acid amplification reaction.

101. The method according to any one of embodiments 95-100, wherein for each modified candidate nucleic acid agent comprised by any modified member, a corresponding identification nucleic acid agent is comprised by the same modified member, wherein said identification nucleic acid agent enables amplification of its corresponding modified candidate nucleic acid agent.

102. The method according to embodiment 101, wherein said identification nucleic acid agent is immobilized to the same solid support as its corresponding modified candidate nucleic acid agent.

103. The method according to any one of embodiments 101-102, wherein said identification nucleic acid agent contains nucleic acid sequence information of its corresponding modified candidate nucleic acid agent.

104. The method according to any one of embodiments 101-103, wherein said identification nucleic acid agent is capable of being amplified in a nucleic acid amplification reaction and/or being sequenced.

105. The method according to any one of embodiments 101-104, wherein said identification nucleic acid agent comprises the same nucleic acid sequence as that of its corresponding modified candidate nucleic acid agent.

106. The method according to any one of embodiments 101-105, wherein said identification nucleic acid agent is the same as its corresponding modified candidate nucleic acid agent, except that said identification nucleic acid agent does not comprise any modified nucleotide while said modified candidate nucleic acid agent comprises at least one modified nucleotide.

107. The method according to any one of embodiments 101-106, wherein said identification nucleic acid agent consists essentially of natural nucleotides.

108. The method according to any one of embodiments 101-107, wherein said identification nucleic acid agent consists of natural DNA.

109. The method according to any one of embodiments 101-108, wherein said identification nucleic acid agent is also comprised by the kernel member employed to generate its corresponding modified candidate nucleic acid agent.

110. The method according to any one of embodiments 101-109, wherein said identification nucleic acid agent comprised by the modified member and/or the kernel member is single-stranded.

111. The method according to any one of embodiments 101-110 wherein on any modified member, a ratio of the number of a modified candidate nucleic acid agent to that of its corresponding identification nucleic acid agent is from about $10^{10}$:1 to about 1:1.

112. The method according to any one of embodiments 95-111, wherein said modified candidate nucleic acid agent is capable of specifically binding to a target.

113. The method according to embodiment 112, wherein said target is a protein target.

114. The method according to any one of embodiments 112-113, wherein said modified candidate nucleic acid agent comprises an aptamer.

115. The method according to any one of embodiments 95-114, wherein said modified candidate nucleic acid agent is capable of specifically binding to a target with a Kd of from about 1 pM to about 100 µM.

116. The method according to any one of embodiments 95-115, wherein said modified candidate nucleic acid agent consists essentially of modified nucleotides.

117. The method according to any one of embodiments 95-116, wherein said modified nucleotide comprises a chemical substitution or modification at one or more positions independently selected from the group consisting of a ribose position, a deoxyribose position, a phosphate position, and a base position.

118. The method according to any one of embodiments 95-117, wherein said modified nucleotide comprises one or more modifications independently selected from the group consisting of a 2'-position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, a methylation, a 3' cap, and a 5' cap.

119. The method according to embodiment 118, wherein said 5-position modified pyrimidine is selected from the group consisting of 5-Carboxy-2'-deoxyuridine, 5-Aminoallyl-2'-deoxyuridine, 5-[(3-Indolyl)propionamide-N-allyl]-2'-deoxyuridine, 5-Carboxy-2'-deoxycytidine, 5-Aminoallyl-2'-deoxycytidine, Biotin-16-Aminoallyl-2'-deoxycytidine, 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

120. The method according to any one of embodiments 95-119, wherein one or more of the nucleic acid agents immobilized to said solid support comprises a molecule conjugated thereto.

121. The method according to embodiment 120, wherein said molecule is selected from the group consisting of a small molecule, a fluorophore, a peptide, a therapeutically active component and an siRNA.

122. The method according to any one of embodiments 95-121, wherein said solid support is a particle.

123. The method according to any one of embodiments 95-122, wherein said solid support is non-magnetic, magnetic or paramagnetic.

124. The method according to any one of embodiments 95-123, wherein said solid support has at least one dimension of from about 50 nm to about 100 µm.

125. The method according to any one of embodiments 95-124, wherein about $10^2$ to about $10^{10}$ nucleic acid agents are immobilized to any solid support.

126. The method according to any one of embodiments 95-125, wherein said providing a pool comprising a plurality of kernel members in a) comprises: a1) providing a pool comprising a plurality of template members, with each template member comprising a plurality of double-stranded candidate nucleic acid agents immobilized to the solid support, and each double-stranded candidate nucleic acid agent comprises a forward strand and a complementary reverse strand; a2) treating the plurality of template members of a1) to remove a substantial part of the forward strand of said double-stranded candidate nucleic acid agents, with the corresponding reverse strand immobilized on said solid support, forming said reverse strand of the partially double-stranded candidate nucleic acid agents of the kernel members.

127. The method according to embodiment 126, wherein sequence diversity of the double-stranded candidate nucleic acid agents comprised by any one of the template members in the pool is less than that of the total double-stranded candidate nucleic acid agents comprised by all the template members in the pool.

128. The method according to any one of embodiments 126-127, wherein any one of the template members in the pool comprises at least $1\times10^2$ copies of double-stranded candidate nucleic acid agents having the same nucleic acid sequence.

129. The method according to any one of embodiments 126-128, wherein sequence diversity of the double-stranded candidate nucleic acid agents comprised by any template member in the pool is from 1 to 1000.

130. The method according to any one of embodiments 126-129, wherein a 5' end of said forward strand of the double-stranded candidate nucleic acid agents is attached directly or indirectly to the solid support of the template members.

131. The method according to any one of embodiments 126-130, wherein a1) comprises generating said template members comprising the plurality of double-stranded candidate nucleic acid agents using emulsion PCR.

132. The method according to any one of embodiments 126-131, wherein for each double-stranded candidate nucleic acid agent comprised by any template member, a corresponding double-stranded identification nucleic acid agent is comprised by the same template member, the double-stranded identification nucleic acid agent comprises a forward strand and a complementary reverse strand, and wherein said double-stranded identification nucleic acid agent is different from its corresponding double-stranded candidate nucleic acid agent while enabling amplification thereof.

133. The method according to embodiment 132, wherein said double-stranded identification nucleic acid agent contains nucleic acid sequence information of its corresponding double-stranded candidate nucleic acid agent.

134. The method according to any one of embodiments 132-133, wherein said double-stranded identification nucleic acid agent comprises the same nucleic acid sequence as its corresponding double-stranded candidate nucleic acid agent.

135. The method according to any one of embodiments 132-134, wherein on any template member, a ratio of the number of a double-stranded candidate nucleic acid agent to that of its corresponding double-stranded identification nucleic acid agent is from about $10^{10}$:1 to about 1:1.

136. The method according to any one of embodiments 132-135, wherein a2) comprises: a2-1) treating the plurality of template members of a1) to remove only the reverse strand of the double-stranded identification nucleic acid agent, and the forward strand of the double-stranded identification nucleic acid agent remains immobilized on the solid support, forming the identification nucleic acid agent on the kernel member and/or the modified member.

137. The method according to embodiment 136, wherein a2) further comprises a2-2) treating the plurality of template members obtained in a2-1) so that a substantial part of the forward strand of the double-stranded candidate nucleic acid agents is removed, with the reverse strand of said double-stranded candidate nucleic acid agents immobilized on said solid support, forming said reverse strand of the partially double-stranded candidate nucleic acid agents of the kernel members.

138. The method according to any one of embodiments 95-137, wherein in b), after extending said forward strand of the partially double-stranded candidate nucleic acid agent, the reverse strands are removed, and the modified candidate nucleic acid agents comprised by the modified members are single-stranded.

139. The method according to embodiment 138, wherein after extending said forward strand of the partially double-stranded candidate nucleic acid agent, the reverse strands are removed by incubation with an alkaline solution.

140. The method according to any one of embodiments 126-139, wherein the reverse strand of said double-stranded candidate nucleic acid agent is resistant to 5' to 3' exonuclease digestion.

141. The method according to any one of embodiments 126-140, wherein a 5'end of the reverse strand of said double-stranded candidate nucleic acid agent is phosphorothioated.

142. The method according to any one of embodiments 132-141, wherein the reverse strand of said double-stranded identification nucleic acid agent is susceptible to 5' to 3' exonuclease digestion.

143. The method according to any one of embodiments 136-142, wherein a2-1) comprises treating the plurality of template members of a1) with a 5' to 3' exonuclease thereby removing only the reverse strand of the double-stranded identification nucleic acid agent.

144. The method according to any one of embodiments 126-143, wherein a2) comprises removing a substantial part of the forward strand of said double-stranded candidate nucleic acid agents with an exonuclease.

145. The method according to any one of embodiments 137-144, wherein a2-2) comprises treating the plurality of template members obtained in a2-1) with a site-specific nicking enzyme to generate nicked forward strand of the double-stranded candidate nucleic acid agents.

146. The method according to any one of embodiments 126-145, wherein in a2), a remaining part of the forward strand of the double-stranded candidate nucleic acid agent is not removed and remains immobilized on the solid support, serving as the forward strand of the partially double-stranded candidate nucleic acid agent on the kernel members, and the reverse strand of the double-stranded candidate nucleic acid agent remains associated with said remaining part of said forward stand, serving as the reverse strand of the partially double-stranded candidate nucleic acid agent on the kernel members.

147. The method according to any one of embodiments 137-144, wherein a2-2) comprises treating the plurality of template members obtained in a2-1) with a site-specific restriction enzyme to generate double-stranded break of the double-stranded candidate nucleic acid agents.

148. The method according to any one of embodiments 126-147, wherein said template member further comprises a plurality of single-stranded forward primers immobilized on the solid support, said single-stranded forward primers are capable of associating with said reverse strand of the double-stranded candidate nucleic acid agent subsequent to removal of a substantial part of the forward strand of the double-stranded candidate nucleic acid agent.

149. The method according to any one of embodiments 95-148, wherein b) comprises extending said forward strand of the partially double-stranded candidate nucleic acid agents with a nucleic acid polymerase.

150. The method according to any one of embodiments 136-149, wherein subsequent to a2-1), said member is encapsulated in a reaction compartment.

151. The method according to embodiment 150, wherein the reaction compartment further comprises one or more of the following: a nicking enzyme, a site-specific restriction enzyme, an exonuclease, a polymerase, and modified dNTPs.

152. A pool comprising a plurality of kernel members, with each kernel member comprising a plurality of partially double-stranded candidate nucleic acid agents immobilized to a solid support, and each of said partially double-stranded candidate nucleic acid agents comprises a forward strand and a reverse strand longer than said forward strand, wherein said forward and reverse strand associate with each other at least partially via base-paring; wherein a nucleic acid sequence of the candidate nucleic acid agents comprised by any kernel member is different from that of the candidate nucleic acid agents comprised by at least one other kernel member in the pool.

153. The pool according to embodiment 152, wherein sequence diversity of the candidate nucleic acid agents comprised by any kernel member in the pool is less than that of the total candidate nucleic acid agents comprised by all the kernel members in the pool.

154. The pool according to any one of embodiments 152-153, wherein any one of the kernel members in the pool comprises at least $1 \times 10^2$ copies of candidate nucleic acid agents having the same nucleic acid sequence.

155. The pool according to any one of embodiments 152-154, wherein sequence diversity of the candidate nucleic acid agents comprised by any kernel member in the pool is from 1 to 1000.

156. The pool according to any one of embodiments 152-155, wherein a 5' end of said forward strand of the partially double-stranded candidate nucleic acid agents is attached directly or indirectly to the solid support.

157. The pool according to any one of embodiments 152-156, wherein for each partially double-stranded candidate nucleic acid agents comprised by any kernel member, a corresponding identification nucleic acid agent is comprised by the same kernel member, wherein said identification nucleic acid agent enables amplification of its corresponding candidate nucleic acid agent.

158. The pool according to embodiment 157, wherein said identification nucleic acid agent is immobilized to the same solid support as its corresponding candidate nucleic acid agent.

159. The pool according to any one of embodiments 157-158, wherein the identification nucleic acid agent is single-stranded.

160. The pool according to any one of embodiments 157-159, wherein said identification nucleic acid agent contains nucleic acid sequence information of its corresponding candidate nucleic acid agent.

161. The pool according to any one of embodiments 157-160, wherein said identification nucleic acid agent is capable of being amplified in a nucleic acid amplification reaction and/or being sequenced.

162. The pool according to any one of embodiments 157-161, wherein said identification nucleic acid agent comprises the same nucleic acid sequence as that of its corresponding candidate nucleic acid agent.

163. The pool according to any one of embodiments 157-162, wherein said identification nucleic acid agent consists essentially of natural nucleotides.

164. The pool according to any one of embodiments 157-163, wherein said identification nucleic acid agent consists of natural DNA.

165. The pool according to any one of embodiments 157-164, wherein on any kernel member, a ratio of the number of a candidate nucleic acid agent to that of its corresponding identification nucleic acid agent is from about $10^{10}$:1 to about 1:1.

166. The pool according to any one of embodiments 152-165, wherein said solid support is a particle.

167. The pool according to any one of embodiments 152-166, wherein said solid support is non-magnetic, magnetic or paramagnetic.

168. The pool according to any one of embodiments 152-167, wherein said solid support has at least one dimension of from about 50 nm to about 100 µm.

169. The pool according to any one of embodiments 152-168, wherein about $10^2$ to about $10^{10}$ nucleic acid agents are immobilized to any solid support.

170. A pool comprising a plurality of modified members, with each modified member comprising a plurality of modified candidate nucleic acid agents immobilized to a solid support, and each modified candidate nucleic acid agent comprises at least one modified nucleotide; wherein a nucleic acid sequence of the modified candidate nucleic acid agents comprised by any modified member is different from that of the modified candidate nucleic acid agents comprised by at least one other modified member in the pool.

171. The pool according to embodiment 170, wherein sequence diversity of the modified candidate nucleic acid agents comprised by any modified member in the pool is less than that of the total modified candidate nucleic acid agents comprised by all the modified members in the pool.

172. The pool according to any one of embodiments 170-171, wherein any one of the modified members in the pool comprises at least $1 \times 10^2$ copies of modified candidate nucleic acid agents having the same nucleic acid sequence.

173. The pool according to any one of embodiments 170-172, wherein sequence diversity of the modified candidate nucleic acid agents comprised by any modified member in the pool is from 1 to 1000.

174. The pool according to any one of embodiments 170-173, wherein the modified candidate nucleic acid agents are single-stranded.

175. The pool according to embodiment 174, wherein a 5' end of said single-stranded modified candidate nucleic acid agent is attached directly or indirectly to the solid support.

176. The pool according to any one of embodiments 170-175, wherein said modified candidate nucleic acid agent is not capable of functioning directly as a template in a nucleic acid amplification reaction.

177. The pool according to any one of embodiments 170-176, wherein for each modified candidate nucleic acid agent comprised by any modified member, a corresponding identification nucleic acid agent is comprised by the same modified member, wherein said identification nucleic acid agent enables amplification of its corresponding modified candidate nucleic acid agent.

178. The pool according to embodiment 177, wherein said identification nucleic acid agent is immobilized to the same solid support as its corresponding modified candidate nucleic acid agent.

179. The pool according to any one of embodiments 177-178, wherein said identification nucleic acid agent contains nucleic acid sequence information of its corresponding modified candidate nucleic acid agent.

180. The pool according to any one of embodiments 177-179, wherein said identification nucleic acid agent is capable of being amplified in a nucleic acid amplification reaction and/or being sequenced.

181. The pool according to any one of embodiments 177-180, wherein said identification nucleic acid agent comprises the same nucleic acid sequence as that of its corresponding modified candidate nucleic acid agent.

182. The pool according to any one of embodiments 177-181, wherein said identification nucleic acid agent is the same as its corresponding modified candidate nucleic acid agent, except that said identification nucleic acid agent does not comprise any modified nucleotide while said modified candidate nucleic acid agent comprises at least one modified nucleotide.

183. The pool according to any one of embodiments 177-182, wherein said identification nucleic acid agent consists essentially of natural nucleotides.

184. The pool according to any one of embodiments 177-183, wherein said identification nucleic acid agent consists of natural DNA.

185. The pool according to any one of embodiments 177-184, wherein said identification nucleic acid agent is single-stranded.

186. The pool according to any one of embodiments 177-185, wherein on any modified member, a ratio of the number of a modified candidate nucleic acid agent to that of its corresponding identification nucleic acid agent is from about $10^{10}:1$ to about 1:1.

187. The pool according to any one of embodiments 170-186, wherein said modified candidate nucleic acid agent is capable of specifically binding to a target.

188. The pool according to embodiment 187, wherein said target is a protein target.

189. The pool according to any one of embodiments 187-188, wherein said modified candidate nucleic acid agent comprises an aptamer.

190. The pool according to any one of embodiments 170-189, wherein said modified candidate nucleic acid agent is capable of specifically binding to a target with a Kd of from about 1 pM to about 100 μM.

191. The pool according to any one of embodiments 170-190, wherein said modified candidate nucleic acid agent consists essentially of modified nucleotides.

192. The pool according to any one of embodiments 170-191, wherein said modified nucleotide comprises a chemical substitution or modification at one or more positions independently selected from the group consisting of a ribose position, a deoxyribose position, a phosphate position, and a base position.

193. The pool according to any one of embodiments 170-192, wherein said modified nucleotide comprises one or more modifications independently selected from the group consisting of a 2'-position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, a methylation, a 3' cap, and a 5' cap.

194. The pool according to embodiment 193, wherein said 5-position modified pyrimidine is selected from the group consisting of 5-Carboxy-2'-deoxyuridine, 5-Aminoallyl-2'-deoxyuridine, 5-[(3-Indolyl)propionamide-N-allyl]-2'-deoxyuridine, 5-Carboxy-2'-deoxycytidine, 5-Aminoallyl-2'-deoxycytidine, Biotin-16-Aminoallyl-2'-deoxycytidine, 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

195. The pool according to any one of embodiments 170-194, wherein one or more of the modified candidate nucleic acid agents immobilized to said solid support comprises a molecule conjugated thereto.

196. The pool according to embodiment 195, wherein said molecule is selected from the group consisting of a small molecule, a fluorophore, a peptide, a therapeutically active component and an siRNA.

197. The pool according to any one of embodiments 170-196, wherein said solid support is a particle.

198. The pool according to any one of embodiments 170-197, wherein said solid support is non-magnetic, magnetic or paramagnetic.

199. The pool according to any one of embodiments 170-198, wherein said solid support has at least one dimension of from about 50 nm to about 100 μm.

200. The pool according to any one of embodiments 170-199, wherein about $10^2$ to about $10^{10}$ nucleic acid agents are immobilized to any solid support.

201. A pool comprising a plurality of template members, with each template member comprising a plurality of double-stranded candidate nucleic acid agents immobilized to a solid support, and each of said double-stranded candidate nucleic acid agents comprises a forward strand and a complementary reverse strand;
wherein a nucleic acid sequence of the double-stranded candidate nucleic acid agents comprised by any template member is different from that of the double-stranded candidate nucleic acid agents comprised by at least one other template member in the pool.

202. The pool according to embodiment 201, wherein sequence diversity of the double-stranded candidate nucleic acid agents comprised by any template member in the pool is less than that of the total double-stranded candidate nucleic acid agents comprised by all the template members in the pool.

203. The pool according to any one of embodiments 201-202, wherein any one of the template members in the pool comprises at least $1\times10^2$ copies of double-stranded candidate nucleic acid agents having the same nucleic acid sequence.

204. The pool according to any one of embodiments 201-203, wherein sequence diversity of the double-stranded candidate nucleic acid agents comprised by any template member in the pool is from 1 to 1000.

205. The pool according to any one of embodiments 201-204, wherein a 5' end of said forward strand of the double-stranded candidate nucleic acid agents is attached directly or indirectly to the solid support of the template members.

206. The pool according to any one of embodiments 201-205, wherein for each double-stranded candidate nucleic acid agent comprised by any template member, a corresponding double-stranded identification nucleic acid agent is comprised by the same template member, the double-stranded identification nucleic acid agent comprises a forward strand and a complementary reverse strand, and wherein said double-stranded identification nucleic acid agent is different from its corresponding double-stranded candidate nucleic acid agent while enabling amplification thereof.

207. The pool according to embodiment 206, wherein said double-stranded identification nucleic acid agent is immobilized to the same solid support as its corresponding double-stranded candidate nucleic acid agent.

208. The pool according to any one of embodiments 206-207, wherein said double-stranded identification nucleic acid agent contains nucleic acid sequence information of its corresponding double-stranded candidate nucleic acid agent.

209. The pool according to any one of embodiments 206-208, wherein said double-stranded identification nucleic acid agent comprises the same nucleic acid sequence as its corresponding double-stranded candidate nucleic acid agent.

210. The pool according to any one of embodiments 206-209, wherein on any template member, a ratio of the number of a double-stranded candidate nucleic acid agent to that of its corresponding double-stranded identification nucleic acid agent is from about $10^{10}$:1 to about 1:1.

211. The pool according to any one of embodiments 201-210, wherein the reverse strand of said double-stranded candidate nucleic acid agent is resistant to 5' to 3' exonuclease digestion.

212. The pool according to any one of embodiments 201-211, wherein a 5'end of the reverse strand of said double-stranded candidate nucleic acid agent is phosphorothioated.

213. The pool according to any one of embodiments 206-212, wherein the reverse strand of said double-stranded identification nucleic acid agent is susceptible to 5' to 3' exonuclease digestion.

214. The pool according to any one of embodiments 206-213, wherein said double-stranded identification nucleic acid agent consists essentially of natural nucleotides.

215. The pool according to any one of embodiments 206-214, wherein said double-stranded identification nucleic acid agent consists of natural DNA.

216. The pool according to any one of embodiments 201-215, wherein said solid support is a particle.

217. The pool according to any one of embodiments 201-216, wherein said solid support is non-magnetic, magnetic or paramagnetic.

218. The pool according to any one of embodiments 201-217, wherein said solid support has at least one dimension of from about 50 nm to about 100 µm.

219. The pool according to any one of embodiments 201-218, wherein about $10^2$ to about $10^{10}$ double-stranded nucleic acid agents are immobilized to any solid support.

220. The pool according to any one of embodiments 201-219, wherein said template member further comprises a plurality of single-stranded forward primers immobilized on the solid support, said single-stranded forward primers are capable of hybridizing with said reverse strand of the double-stranded candidate nucleic acid agent at least partially via base-paring.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1 Particle Generation and Validation

An example for generating a pool of modified members (also referred to as MAPs) according to the present disclosure is shown in FIGS. 1a-1f. A library of $3 \times 10^8$ random DNA molecules was first transformed into a library of monoclonal template particles through a process of in vitro compartmentalization and emulsion PCR (ePCR) with particles displaying forward primers (FPs) (FIG. 1a). The single-stranded DNA (ssDNA) library and primers were purchased from Integrated DNA Technologies (IDT). The library was synthesized with hand mixing method and PAGE-purified. Each 81-nucleotide (nt) library member featured a 40-nt randomized sequence flanked by 23-nt forward PCR primer and 18-nt reverse PCR primer (5'-ATCCAGAGTGACGCTCTTCAGCA-[40N]-TGCACACCGTCGCTTAGT-3') (SEQ ID NO: 1). Both the forward primers and reverse primers used in this ePCR were specially designed. The forward primer contained a nicking endonuclease cutting site near its 3' end, GCTCTTC, that can be specifically recognized by nicking endonuclease Nt.BspQI. The reverse primers were a 9:1 mixture of synthesized primers with (protected) and without (unprotected) nuclease-resistant phosphorothioated (PS) backbone respectively.

Before the DNA library can be displayed on the particles, the forward primers (FP) need to be coupled to the particles first. To do so, 500 µL of 1-µm MyOne carboxylic acid magnetic particles ($10^7$/µL, Life Technologies) were washed once with 500 µL of 0.01N NaOH, and then three times with 1 mL of nuclease-free water. After the last wash, the particles were resuspended in a 150 µL reaction mixture containing 200 mM NaCl, 0.2 mM 5'-amino-modified FP (5'-amino-PEG18-ATCCAGAGTGACGCTCTTCAGCA-3') (SEQ ID NO: 2), 1 mM imidazole chloride, 50% v/v dimethyl sulfoxide (DMSO) and 250 mM 1-ethyl-3-(3-dimethylaminopropyl)carbodiimide (EDC) (Pierce Biotechnology). Amino group modification enables covalent coupling, keeping FPs attached to the particles during thermal cycling, with the PEG18 at the 5' end serving as a spacer between displayed aptamers and the particle.

The particles were mixed well with reagents, vortexed, sonicated and incubated overnight at room temperature on a rotator. In order to reduce non-specific interaction between the particles and target molecules, remaining carboxyls on the particles were converted into amino-reactive NHS-ester in the presence of 250 mM EDC and 100 mM N-hydroxysuccinimide (NHS) in 2-(N-morpholino)ethanesulfonic acid (MES) buffer (100 mM, PH 4.7) (Pierce Biotechnology) for 30 minutes at room temperature, followed by conjugation with 20 mM amino-PEG12 (Pierce Biotechnology) in MES buffer for one hour. The particles were then washed four times with 500 µL of TET buffer (10 mM Tris, pH 8.0, 0.1 mM EDTA, 0.1% Tween-20), and finally suspended in 500 µL of TE buffer and stored at 4° C. To test conjugation efficiency, we incubated 1 µM Alexa Fluor 647-modified FP complementary sequence (FPC) with 0.2 µL of FP particles in 100 µL of STE buffer (10 mM Tris pH 8.0, 50 mM NaCl, 1 mM EDTA) at 59° C. for 10 minutes, then snap cooled on ice for 2 minutes. The particles were washed twice with 100 µL STE buffer and analyzed by Accuri C6 Flow Cytometer (BD Biosciences). The prepared 500 µL FP particles can be stored at 4° C. and are stable for 6-12 months.

Next, monoclonal template particles were generated via emulsion PCR. The emulsion PCR (ePCR) was performed as described before (see, e.g., Dressman et al. (2003) *Proceedings of the National Academy of Sciences of the United States of America* 100:8817-22; Diehl, F. et al. (2006) *Nature methods* 3: 551-9). Briefly, the oil phase was composed of 4.5% Span 80, 0.40% Tween 80 and 0.05% Triton X-100 in mineral oil, all of which were purchased from Sigma-Aldrich. The oil phase was prepared in bulk and stored at 4° C. for 2 months. The aqueous phase for ePCR had a total volume of 100 µL and consisted of 1× GoTaq PCR Master Mix (Promega), 10 mM $MgCl_2$, 0.8 mM of each dNTP (Promega), 40 nM FP, 2.7 µM protected RP with nuclease-resistant PS backbone, 0.3 µM unprotected RP without nuclease-resistant PS backbone, 0.1 U/µL of GoTaq Hot Start Polymerase (Promega), $3 \times 10^8$ template DNA, and $10^8$ FP-coated particles. Water-in-oil emulsions were prepared by adding 100 µL of the aqueous phase to 500 µL of oil phase in a 1.5 mL tube, and mixing the 1.5 mL tube at 3000 rpm using IKA Vortex 4 digital (IKA, 4050100) for 10 minutes. The emulsions were distributed in 100 µL aliquots into 6 PCR tubes. 25 cycles of PCR were then performed under the following cycling conditions: 95° C. for 3 min, followed by 25 cycles of 95° C. for 15 sec, 60° C. for 15 sec and 72° C. for 45 sec.

After ePCR, particles with a plurality of double-stranded nucleic acid agents immobilized thereto were generated. The plurality of double-stranded nucleic acid agents comprised a first double-stranded population and a second double-stranded population, the first double-stranded population comprised nucleic acid agents containing the protected reverse primer, and the second double-stranded population comprised nucleic acid agents containing the unprotected reverse primer. Because the ratio of unprotected and protected reverse primers was controlled at about 1 to 9 during the ePCR, about 10% of the PCR products displayed on the particle presented unprotected reverse strands (i.e., nucleic acid agents of the second double-stranded population) (FIG. 1b). Accordingly, template particles displaying about 90% of the first double-stranded population and about 10% of the second double-stranded population were obtained.

Next, the template particles/members were translated into Modified Particles/Members (e.g., modified aptamer particles, or MAPs). After PCR, the emulsions were collected from the PCR tubes into a 1.5 mL tube. The emulsion was broken by adding 600 µL 2-butanol to the emulsion, mixed well by vortexing. After vortexing for 30 sec, the particles were centrifuged at 13,000×g for 2 min. After carefully removing the oil phase, the particles were resuspended in 500 µL of emulsion breaking (EB) buffer (100 mM NaCl, 1% Triton X-100, 10 mM Tris-HCl, pH 7.5, and 1 mM EDTA) and transferred them to a new 1.5 mL tube. After vortexing for 30 sec and centrifugation for 90 sec at 13,000× g, the supernatant was removed. The tube was then placed on a magnetic separator (DynaMag-2 Magnet, Life Technologies), and pipetted off remaining supernatant. Particles were washed three times with TET buffer using magnetic separation, then resuspended in 100 µL TE buffer. Quantitative PCR was performed with a CFX96 Touch™ Real-Time PCR Detection System (Bio-Rad) to estimate amplified template copy number for each monoclonal template particle. Calibration samples were prepared by adding $10^6$, $10^7$, $10^8$, $10^9$ or $10^{10}$ templates into a 20 µL reaction containing 250 nM each of FP and RP, 1,000 FP-coated particles, 10 µL GoTaq PCR Master Mix (Promega) and 0.5×SYBR green (Life Technologies). Test samples were prepared identically, but with 1,000 monoclonal template particles. From the threshold cycle, about $4.8 \times 10^7$ sequences on 1,000 particles were quantified. Since only 20% of template particles displayed template sequences, the average copy number of sequences on each template-bearing particle was around $2.4 \times 10^5$.

Then, 50 units of T7 5' to 3' exonuclease (New England Biolabs, M0263) were mixed with the monoclonal template particles displaying double-stranded DNA (dsDNA) templates in 100 µL of CutSmart® Buffer (New England Biolabs, B7204), and incubated for 15 minutes at 25° C. The T7 exonuclease digested only the unprotected reverse strands (~10%) (i.e., the reverse strand of nucleic acid agents in the second double-stranded population) from the 5' end, and left the PS backbone protected reverse strands (i.e., the reverse strand of nucleic acid agents in the first double-stranded population) (90%) intact (FIG. 1c).

Figure 3:
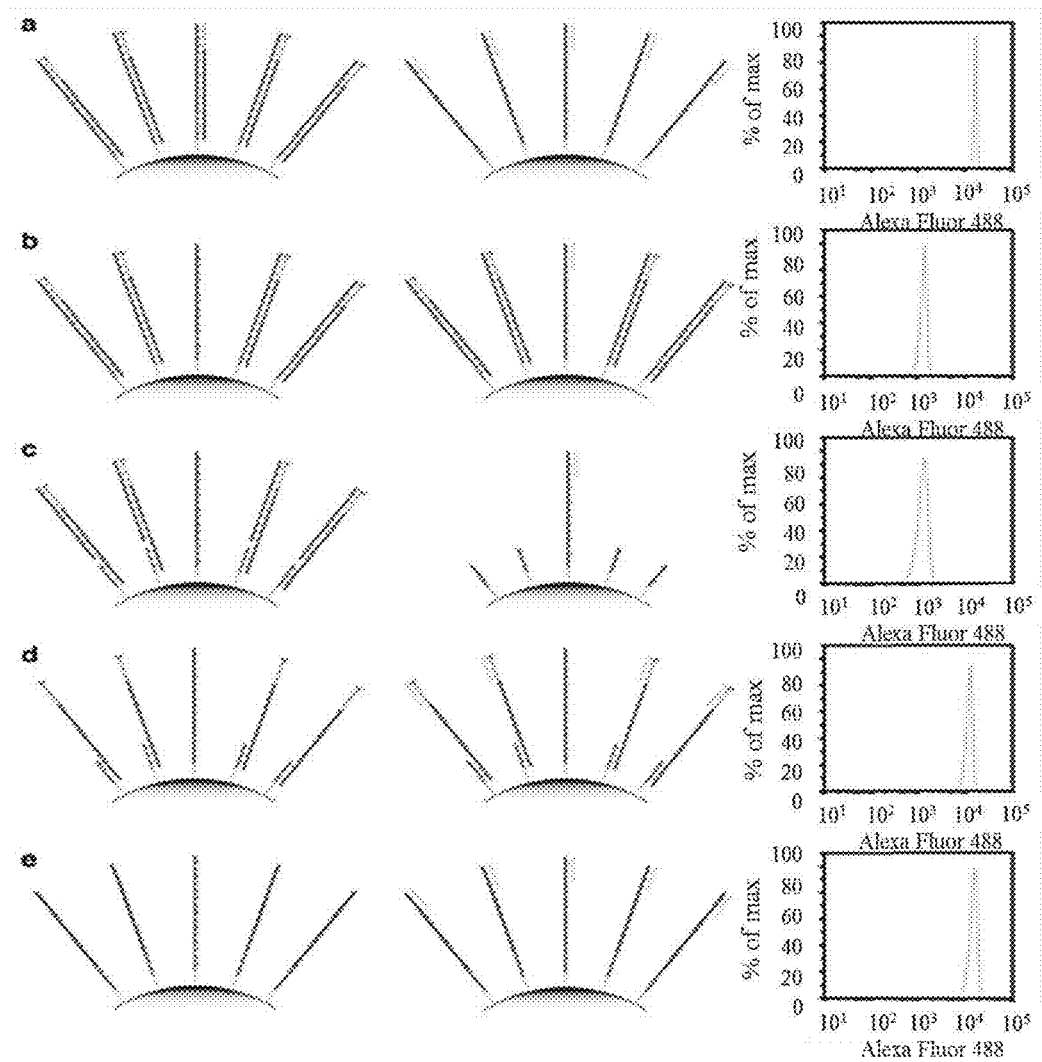
FIGS. 3a-3e illustrate a scheme for validating intermediate products generated in a process for obtaining a pool comprising a plurality of modified members according to the present disclosure.

Fluorescently labeled probes were used to validate intermediate products generated after each step of the process for obtaining a Modified Aptamer Particle (MAP, or modified member according to the present disclosure). For all the tests described in FIGS. 3a-3e, either fluorescently labeled (i.e., Alexa Fluor 488-modified) reverse primer (RP) or RP complementary sequence (RPC) probe was used to quantify the forward or reverse strand of the templates displayed on the particles. After each step during the process, 0.2 µL of the particles were sampled and washed once with 100 µL TET buffer, and incubated the particles with 1 µM of the appropriate fluorescent probes (either Alexa Fluor 488-modified RP or RPC) in 100 µL of STE buffer (10 mM Tris pH 8.0, 50 mM NaCl, 1 mM EDTA) at 50° C. for 10 minutes, then snap cooled on ice for 2 minutes. The particles were then washed twice with 100 µL STE buffer and analyzed by Accuri C6 Flow Cytometer (BD Biosciences) to quantify their fluorescence intensity. As shown in FIG. 3a, when the reverse strand of all the nucleic acid agents immobilized to the particle dissociated from the forward strand by washing twice with 100 mM NaOH, the fluorescently labeled probes (Alexa Fluor 488 RP) hybridized to the forward strands and accordingly, a fluorescent signal was detected, which represented both double-stranded populations. The test in FIG. 3b was done after the first T7 exonuclease digestion (FIG. 1c), when only the reverse strand of nucleic acid agents in the second double-stranded population (e.g., the double-stranded identification nucleic acid agents) was removed by the T7 exonuclease. The fluorescently labeled probe (Alexa Fluor 488 RP) was added without de-hybridizing the reverse strands using NaOH and only hybridized to the forward strand of nucleic acid agents in the second double-stranded population (identification nucleic acid agents, now single stranded after T7 digestion), and a much weaker fluorescent signal was detected.

Figure 6:
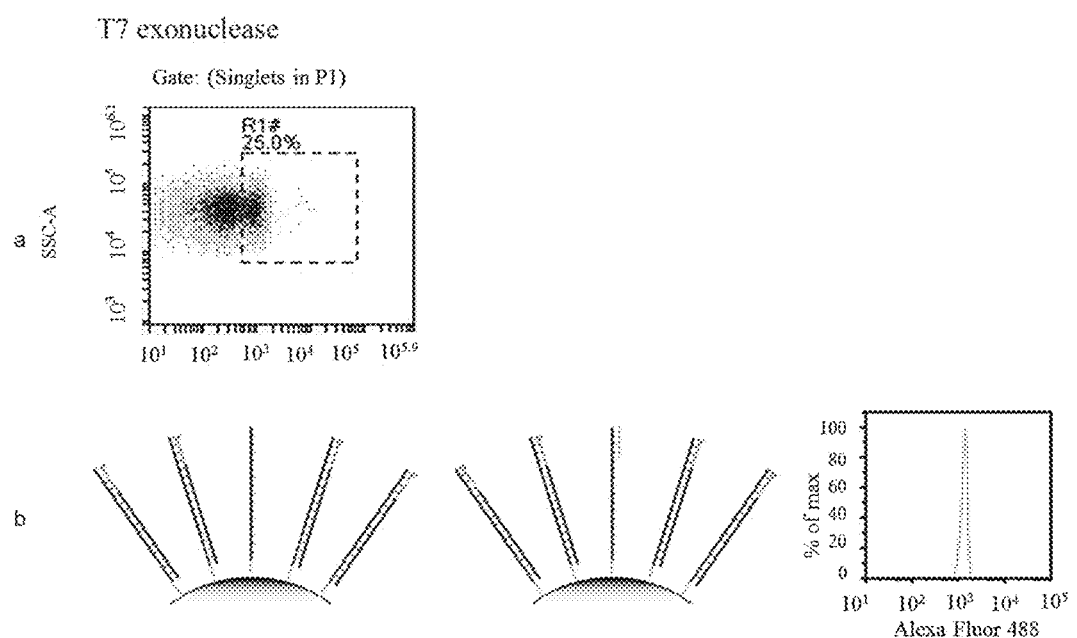
FIGS. 6a-6b illustrate the effects of removing reverse strands using exonucleases.

Moreover, as shown in FIGS. 6a-6b, when the T7 exonuclease (NEB, M0263) was used (FIG. 6a), the reverse strand of nucleic acids in the second double-stranded population (double-stranded identification nucleic acid agents, unprotected at 5'end) was removed, as verified with fluorescent probes complementary to 3' end of a forward strand of the second double-stranded population (i.e., Alexa Fluor 488 RP) (FIG. 6b).

Next, 20 units of Nt.BspQI nicking endonuclease (New England Biolabs, R0644) was added to the template particles in 100 µL of NEBuffer 3.1 (New England Biolabs, B7203) and incubated for 30 minutes at 50° C. in order to cleave only one strand of DNA at the Nt.BspQI recognition site (after nucleotide 20, i.e., after GCTCTTCA) on the double stranded candidate nucleic acid agents (i.e., the forward strand of nucleic acid agents in the first double-stranded population), producing "nicked" candidate nucleic acid agents (FIG. 1d). In this step, ~10% of immobilized nucleic acid agents was single-stranded (i.e., identification nucleic acid agents, comprising the forward strand of nucleic acid agents in the second double-stranded population) due to the previous T7 digestion, and could not be cleaved by the nicking enzyme (FIG. 1d).

As reflected by FIG. 3c, after nicking, the forward strand of nucleic acid agents in the first double-stranded population (double-stranded candidate nucleic acid agents) was nicked (FIG. 1d). After washing twice with 100 mM NaOH to de-hybridize the reverse strands, only the forward strand of nucleic acid agents in the second double-stranded population (identification nucleic acid agents) remained intact and attached to the particle, which hybridized to the fluorescently labeled probe (Alexa Fluor 488 RP), and the signal detected was similar to that in FIG. 3b. Therefore, the effect of nicking was confirmed.

Figure 5:
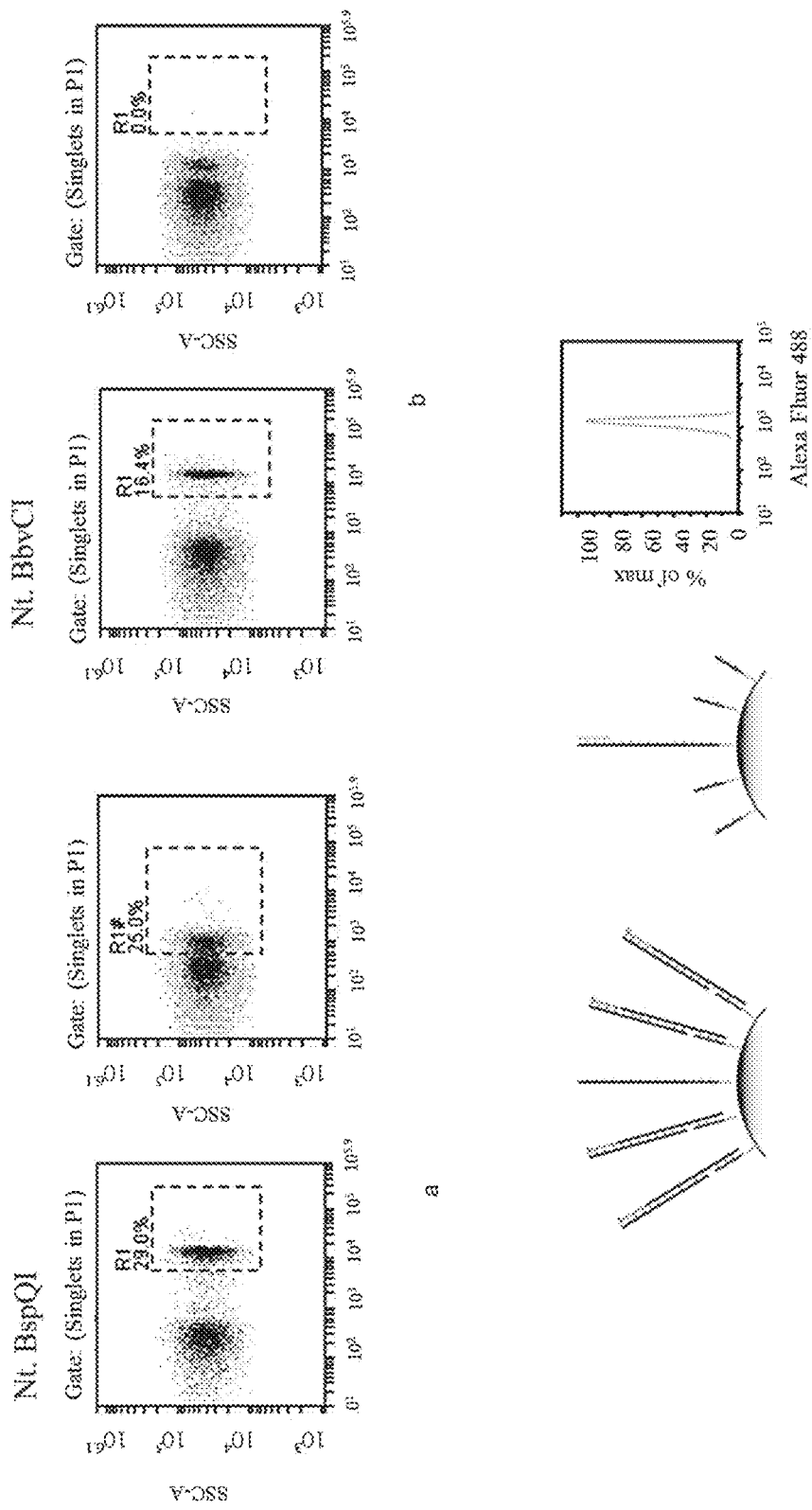
FIGS. 5a-5c illustrate the effects of nicking using various nicking enzymes.

In addition, the effects of the nicking enzyme were also verified when a plurality of different nicking enzymes were used. For example, as shown in FIGS. 5a-5c, when the nicking enzymes Nt. BspQI (NEB, R0644) (FIG. 5a) and Nt. BbvCI (NEB, N0632) (FIG. 5b) were used respectively, nicked forward strand of nucleic acid agents of the first double-stranded population (double-stranded candidate nucleic acid agents) were successfully generated, as verified with fluorescent probes complementary to 3' end of a forward strand of nucleic acid agents in the second double-stranded population (double-stranded identification nucleic acid agents) (FIG. 5c). The nicking reaction buffer, temperature, and time were the same as the ones described above in Example 1.

Figure 8:
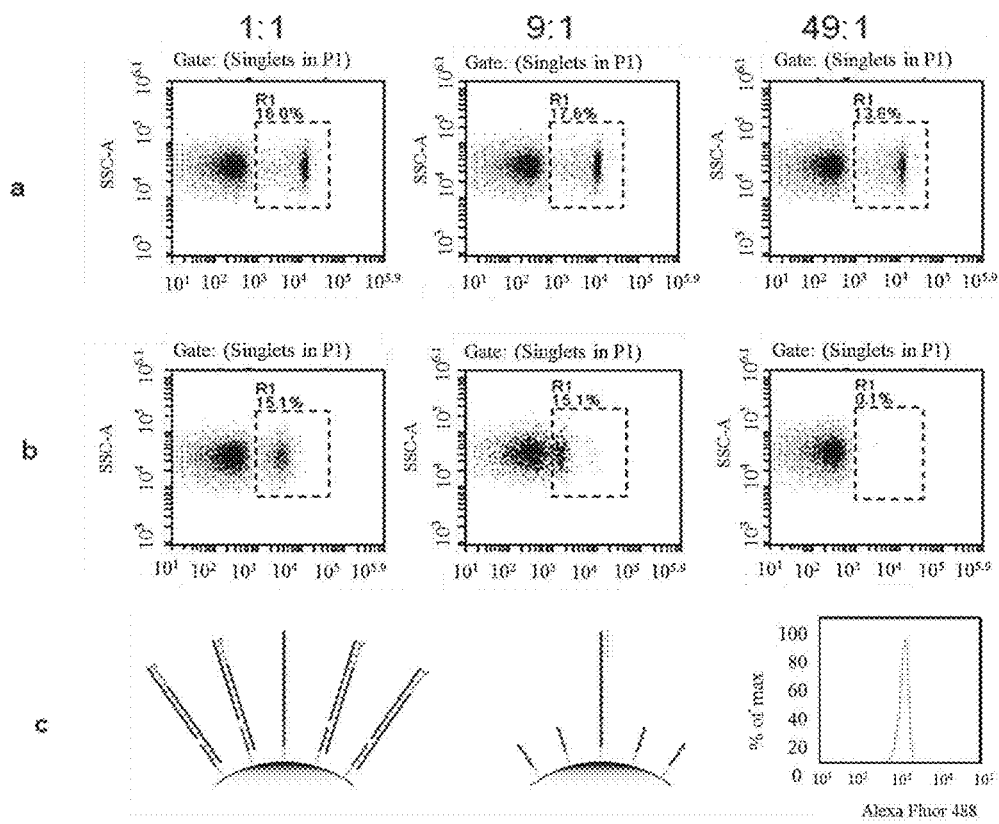
FIGS. 8a-8c illustrate the effects of nicking when the number of candidate nucleic acid agents and that of identification nucleic acid agents are of different ratios.

In addition, as shown in FIGS. 8a-8c, for particles comprising different ratios of nucleic acid agents in the first double-stranded population (double-stranded candidate nucleic acid agents) and the second double-stranded population (double-stranded identification nucleic acid agents), the fluorescent signals detected before nicking (FIG. 8a) and after nicking (FIG. 8b) were changed accordingly, as reflected with fluorescent probes complementary to 3' end of a forward strand of nucleic acid agents in the second double-stranded population (double-stranded identification nucleic acid agents) (FIG. 8c).

The "nicked" particles were then exposed to a second T7 exonuclease (New England Biolabs, M0263) digestion (same condition as the first digestion) to remove only the forward strands (i.e., the forward strand of nucleic acid agents in the first double-stranded population or the double-stranded candidate nucleic acid agents) from the 5' end that is now exposed after the "nicking" (FIG. 1e). After this step, each monoclonal particle displayed 10% natural forward strand identification nucleic acid agent (i.e., the forward strand of nucleic acid agents in the second double-stranded population) and 90% reverse strands (i.e., the reverse strand of nucleic acid agents in the first double-stranded population or double-stranded candidate nucleic acid agents) annealed to forward primers (i.e., the partial complement of the reverse strand of nucleic acid agents in the first double-stranded population, or the remaining part of the forward strand of the double-stranded candidate nucleic acid agents) on the particle (FIG. 1e).

As shown in FIG. 3d, when the reverse strand of nucleic acid agents in the second double-stranded population was removed and the forward strand of nucleic acid agents of the first double-stranded population was partially removed (FIG. 1e), fluorescently labeled probes (Alexa Fluor 488 RPC) only hybridized to the reverse strand of nucleic acid agents in the first double-stranded population.

Next, the particles were washed twice with TET buffer and ready for extension. KOD Xtreme™ Hot Start DNA Polymerase (EMD Millipore, 71975) was used for incorporating natural and modified dNTPs encoded by the reverse template strand (i.e., the reverse strand of nucleic acid agents in the first double-stranded population or the double-stranded candidate nucleic acid agents) (FIG. 1f). 100 μL, extension reaction was prepared for every $10^8$ particles, which consisted of 100 mM KHPO$_4$ (pH 7.4), 10 mM MgCl$_2$, 1 mM DTT, 40 units of KOD Xtreme™ Hot Start DNA Polymerase, dATP, dGTP, dCTP or one of the modified dCTP derivatives, and dTTP or one of the modified dUTP derivatives (final concentration 50 μM for each of the natural dNTP and 100 μM for each of the modified dNTP derivatives). Extension reactions were carried out at 70° C. for 30 min.

Figure 7:
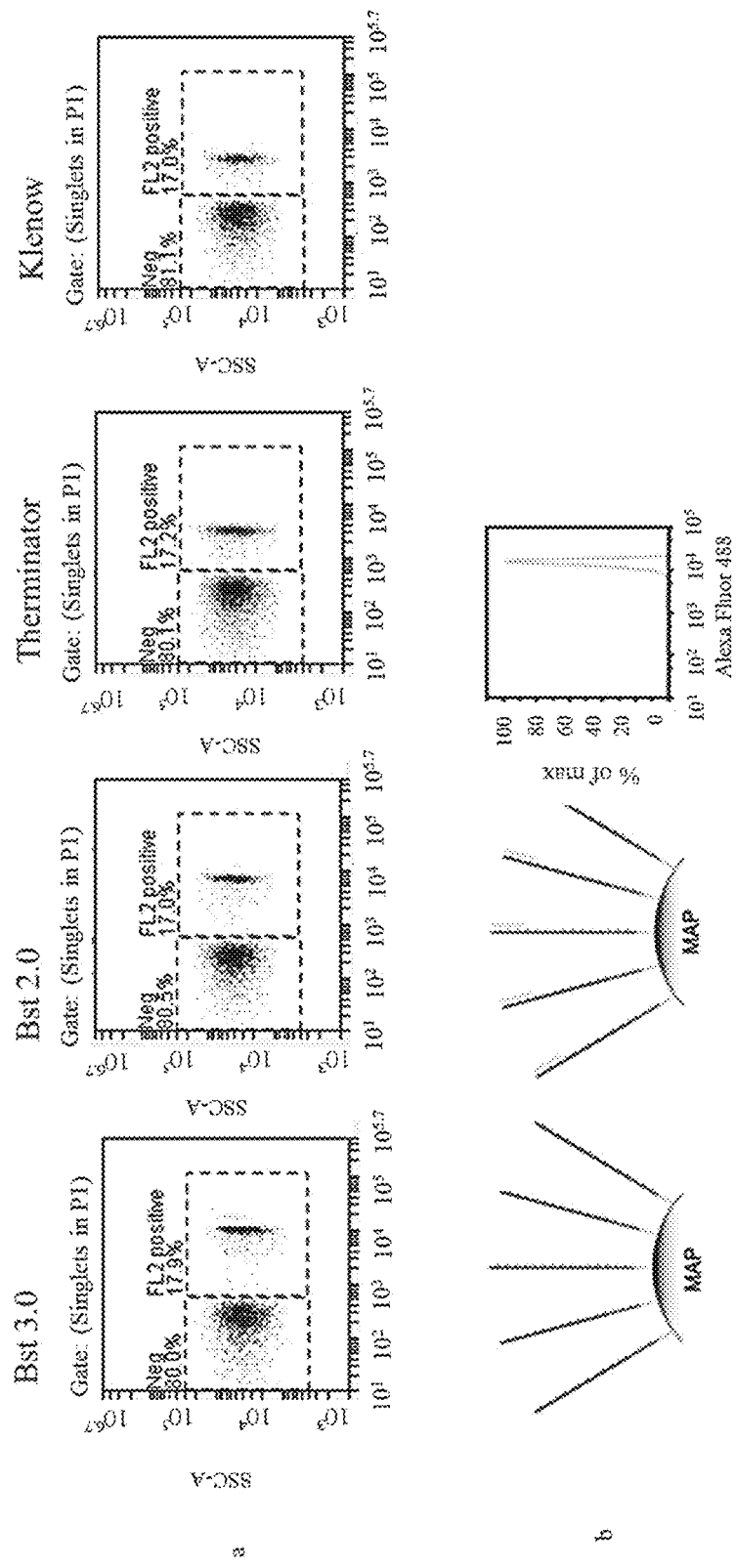
FIGS. 7a-7b illustrate results of nucleic acid strand extension using various polymerases.

The effects of the polymerases were also verified when a plurality of different polymerases were used. For example, as shown in FIGS. 7a-7b, when the polymerase Therminator 9N (NEB, M0261), Klenow (NEB, M0210), BST2.0 (NEB, M0537) and BST3.0 (NEB, M0374) were used, respectively (FIG. 7a), intended nucleic acid agent (e.g., nucleic acid agents in the first single-strand population) extension was successfully achieved, as verified with fluorescent probes complementary to 3' end of the fully synthesized nucleic acid agents (i.e., Alexa Fluor 488 RP) (FIG. 7b).

Figure 4:
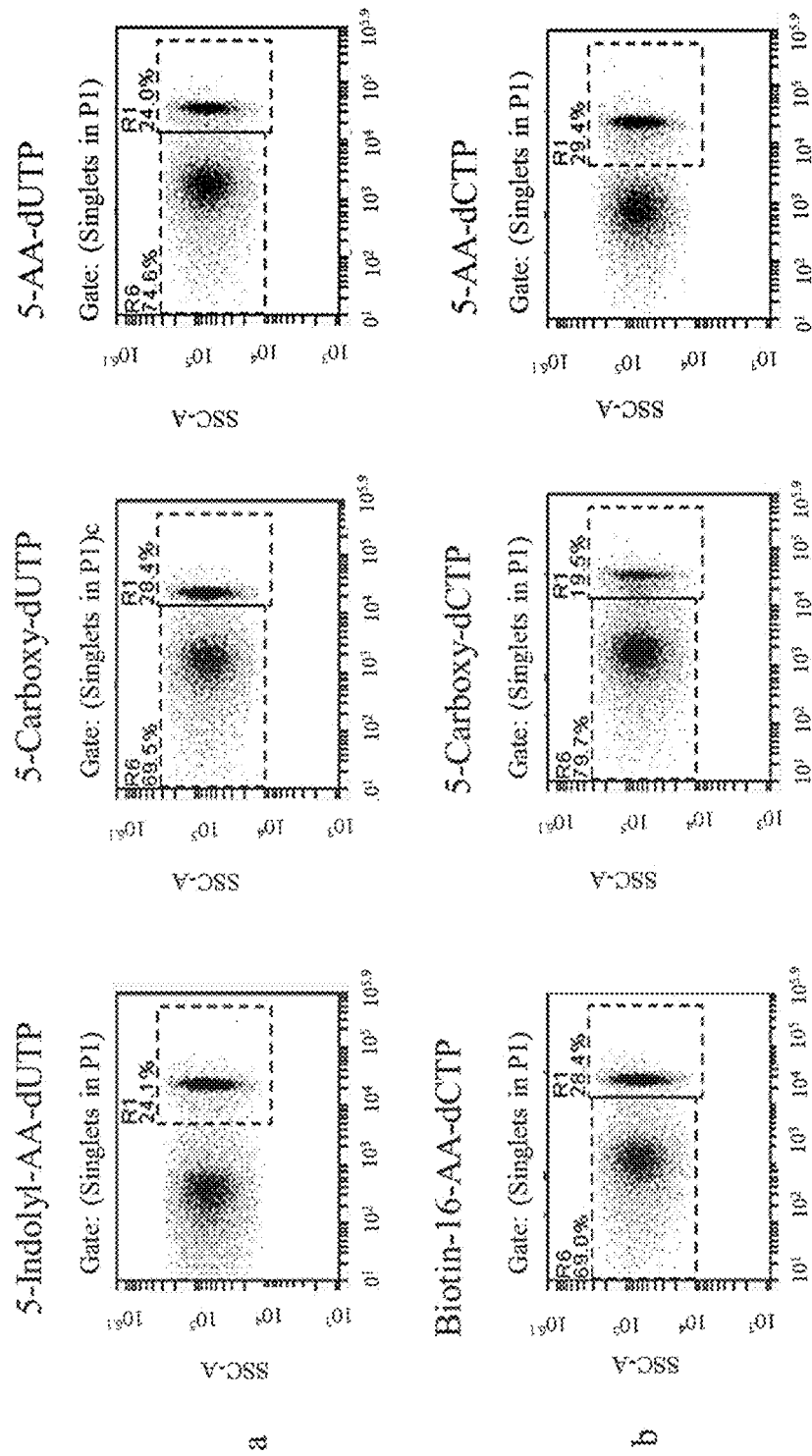
FIGS. 4a-4f illustrate validation results for the generation of intended nucleic acid agents with various modified nucleotides.
Figure 4:
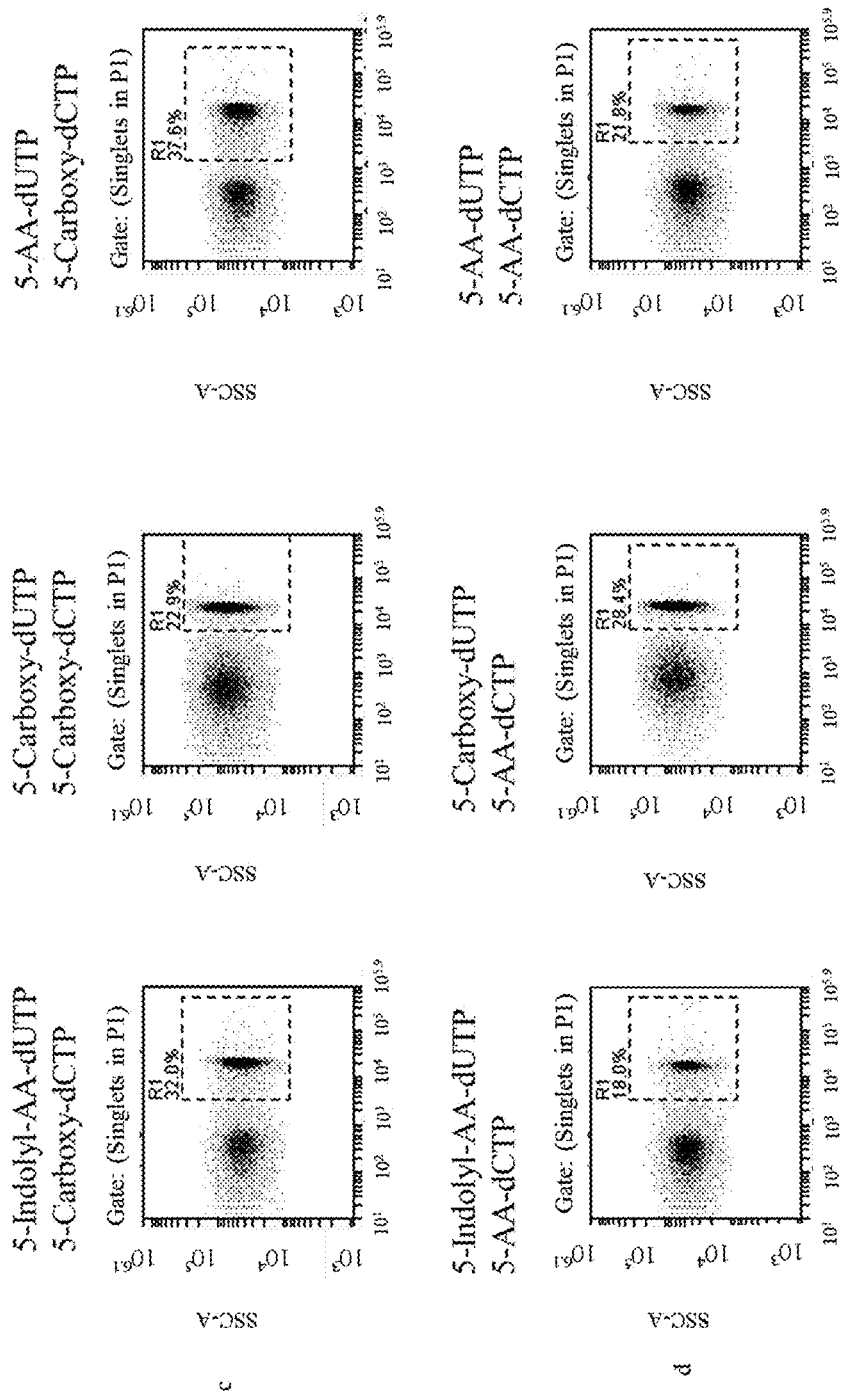
Figure 4:
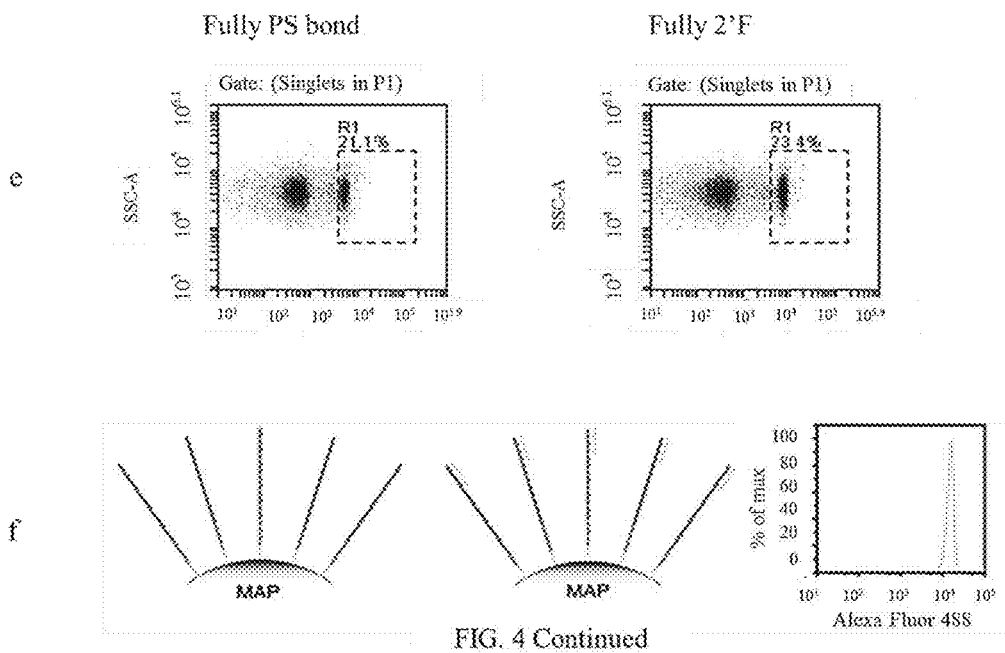

Various modified nucleotides were used to generate particles according to the present disclosure. As can be seen from FIGS. 4a-4f, when modified dUTPs (FIG. 4a), modified dCTPs (FIG. 4b), modified dUTPs and dCTPs (FIG. 4c and FIG. 4d) and 100% modified nucleotides (FIG. 4e) were used, intended nucleic acid agent (e.g., nucleic acid agents in the first single-strand population) extension was successfully achieved, as verified with fluorescent probes complementary to 3' end of the fully synthesized nucleic acid agents (i.e., Alexa Fluor 488 RP) (FIG. 4f). In all experiments described in FIG. 4, final concentration of natural dNTP, side chain-modified dNTP derivatives (FIG. 4a-d), and backbone-modified dNTPs (FIG. 4e-f) were kept at 50 μM, 100 μM and 1 mM respectively.

Figure 11:
FIGS. 11a-11b illustrate the results for incorporation of modified nucleotides.

As shown in FIGS. 11a-11b, when modified nucleotides were used for extension of the nucleic acid strands complementary to the reverse strand of nucleic acid agents in the first double-stranded population (e.g., to generate modified candidate nucleic acid agents), the intended nucleic acid agents were generated in the presence of the modified nucleotide (FIG. 11b, wherein dATP, dGTP, dCTP and modified dUTP were added in the polymerization reaction), in contrast to the control (FIG. 11a, wherein only dATP, dGTP and dCTP were added in the polymerization reaction), indicating that the modified nucleotides were successfully incorporated.

After extension, the emulsion was broken and the reverse strands were de-hybridized, leaving single-strand modified aptamers (i.e., nucleic acid agents of the first single-stranded population or modified candidate nucleic acid agents) (~90%) and natural DNA template sequences (i.e., nucleic acid agents of the second single-stranded population, or identification nucleic acid agents) (~10%) on the particles, completing the formation of modified particles (e.g., MAPs), which were ready for screening. Briefly, the particles were collected by centrifugation in a tube and then resuspended in 200 µM of 0.1 M NaOH and incubated for 2 min. The tube was placed in the magnetic separator for 1 min and the supernatant was carefully removed. After repeating this step twice, the particles were resuspended in 300 µL of TE buffer.

Like the template particles, modified particles/members (e.g., MAPs) are monoclonal wherein each particle displays about $2\times10^5$ copies of a single modified aptamer sequence (i.e., nucleic acid agents of the first single-stranded population, also referred to as the modified candidate nucleic acid agents in the present disclosure) and about $2\times10^4$ copies of amplifiable natural DNA sequences (i.e., nucleic acid agents of the second single-stranded population, also referred to as the identification nucleic acid agents in the present disclosure).

As shown in FIG. 3e, after strand extension (FIG. 1f) and removal of the reverse strand of all the nucleic acid agents immobilized to the particle by washing twice with 100 mM NaOH, the particle comprised a plurality of single-stranded nucleic acid agents, the plurality of single-stranded nucleic acid agents comprised a first single-stranded population (e.g., comprising the modified nucleic acid agents) and a second single-stranded population (e.g., comprising the identification nucleic acid agents), wherein each of the nucleic acid agents in the first single-stranded population was complementary to the reverse strand of nucleic acid agents in the first double-stranded population and comprised modified nucleotides, and the nucleic acid agent in the second single-stranded population was identical to the forward strand of the nucleic acid agent in the second double-stranded population, the fluorescently labeled probe (Alexa Fluor 488 RP) hybridized to nucleic acid agents in both the first and the second single-stranded population.

Figure 9:
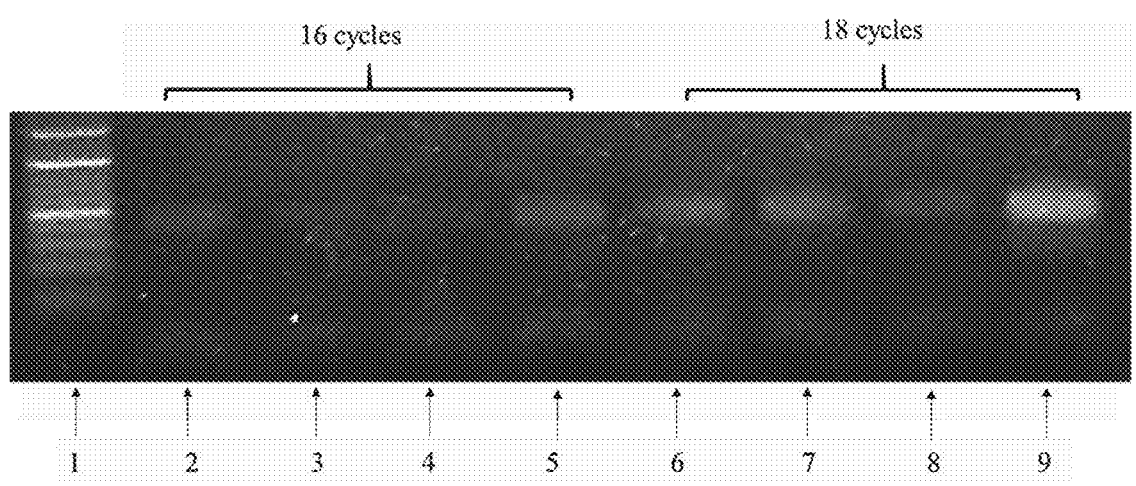
FIG. 9 illustrates amplification results when the number of candidate nucleic acid agents and that of identification nucleic acid agents are of different ratios.

For a particle generated according to the method of the present disclosure, amplification products were also successfully generated when particles having various different ratios of nucleic acid agents in the first single-stranded population and the second single-stranded population were used, as shown in FIG. 9. Lane 1 is a ladder marker; in lane 2 and lane 6, the ratio of nucleic acid agents in the first single-stranded population and the second single-stranded population is 1:1; in lane 3 and lane 7, the ratio of nucleic acid agents in the first single-stranded population and the second single-stranded population is 9:1; in lane 4 and lane 8, the ratio of nucleic acid agents in the first single-stranded population and the second single-stranded population is 49:1; lane 5 and lane 9 demonstrate results from positive controls using reference DNA aptamers.

Figure 10:
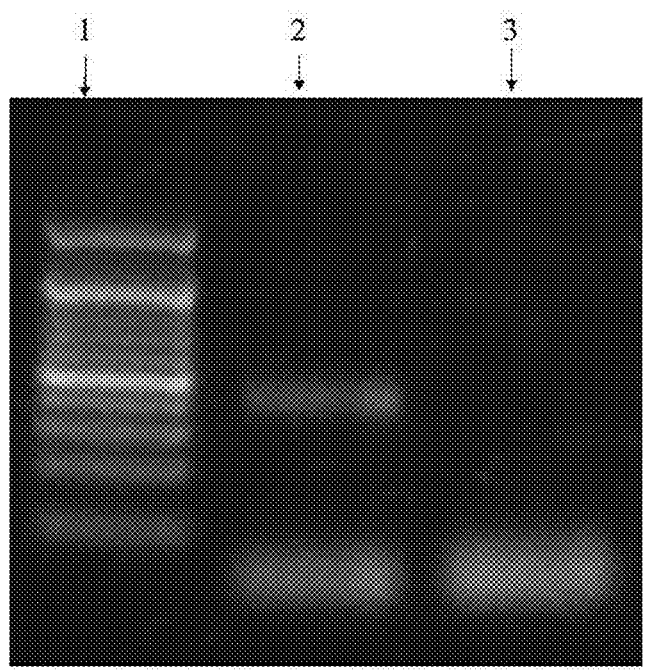
FIG. 10 illustrates amplification results with the presence and absence of natural DNA.

Furthermore, as shown in FIG. 10, for a particle generated according to the method of the present disclosure, amplification products can be produced only when nucleic acid agents of the second single-stranded population (e.g., the identification nucleic acid agents) are present. Lane 1 is the DNA ladder marker, lane 2 shows amplification results from particles comprising nucleic acids agents from both the first and the second single-stranded population, and lane 3 shows amplification results from particles comprising only nucleic acid agents of the first single-stranded population (e.g., modified candidate nucleic acid agents).

Figure 12:
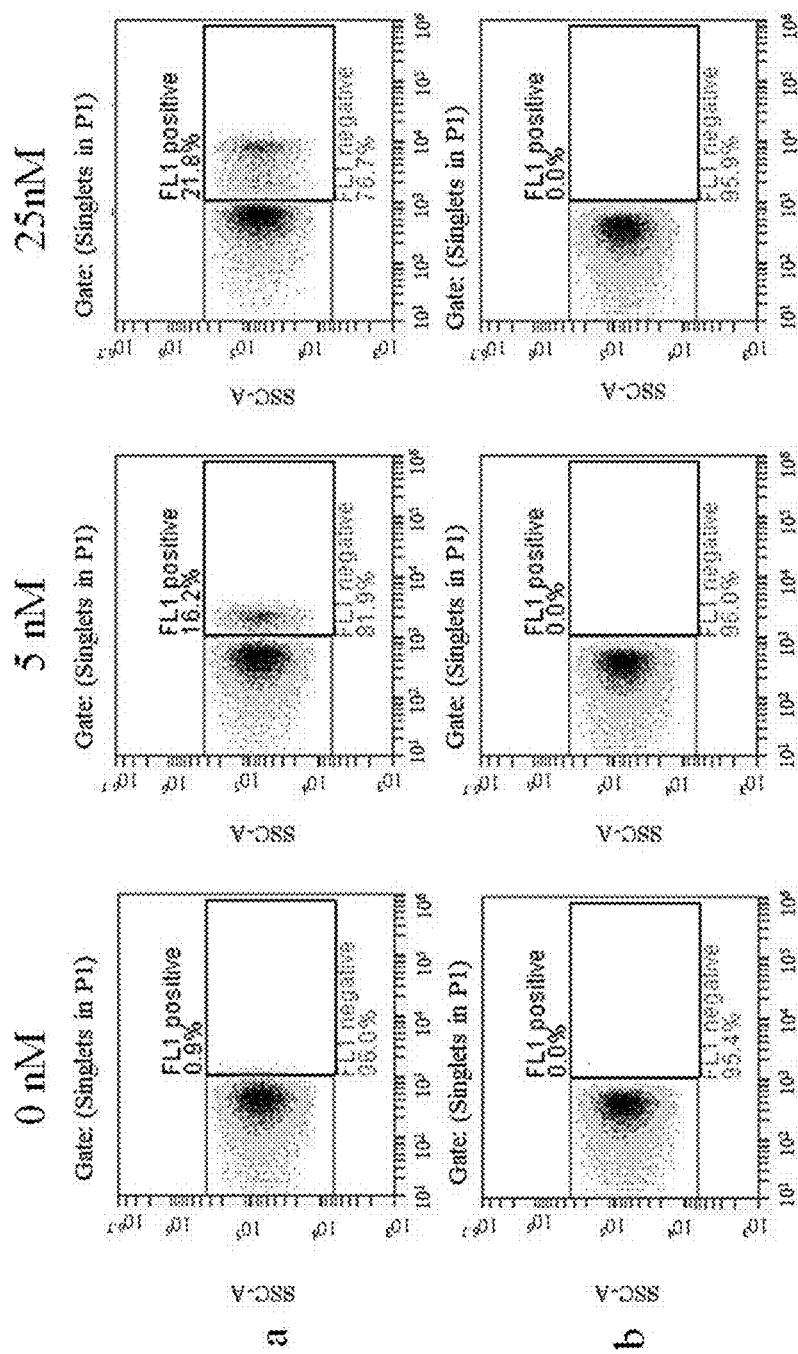
FIGS. 12a-12b illustrate the results of target binding using modified and unmodified nucleotide agents.

In addition, as shown in FIGS. 12a-12b, for a particle generated according to the method of the present disclosure, target binding ability of nucleic acid agents of the first single-stranded population (e.g., the modified candidate nucleic acid agent) was tested using the protein target Neutrophil gelatinase-associated lipocalin (NGAL). Specifically, about $10^6$ Modified Aptamer Particles (MAPs or modified members) were incubated in 100 µL of PBSMCT (DPBS with 2.5 mM $MgCl_2$, 1 mM $CaCl_2$), 0.01% TWEEN-20) with 0 nM, 5 nM or 25 nM NGAL with a Histag. 0.1 mg/ml salmon sperm DNA (Life Technologies) was also added to the reaction to block nonspecific interactions between random DNA and NGAL. 10 µM of His-Tag peptide (GenScript) was also added to eliminate binding to the His-Tag attached to the NGAL proteins. After 1 hour of incubation with the NGAL, the MAPs were washed twice with PBSMCT and the MAP-captured NGAL proteins was labeled with 5 nM fluorescently labeled monoclonal antibody (iFluor 488 His-Tag antibody) for 20 minutes. The MAPs were then washed with PBSMCT twice and measured by FACS for the Alexa 488 signals. For targets at different concentrations (5 nM and 25 nM), only nucleic acid agents with modified nucleotides (FIG. 12a) could generate a binding signal, while natural DNA nucleic acid agents of the same nucleic acid sequence did not bind to the targets (FIG. 12b), indicating that the binding activity results from nucleic acid agents of the first single-stranded population (e.g., modified candidate nucleic acid agents).

Figure 13:
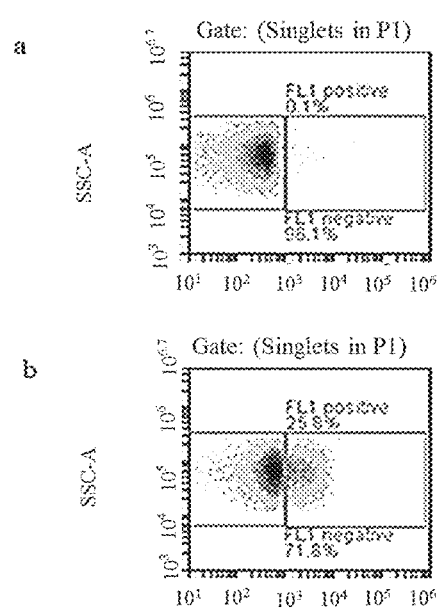
FIGS. 13a-13b illustrate the results of target binding using unmodified and modified nucleotide agents.

Moreover, as shown in FIGS. 13a-13b, target binding ability of nucleic acid agents in a particle library was also tested using the protein target NGAL. The library comprises either particles with modified nucleic acid agents (e.g., the nucleic acid agents comprise modified nucleotides, FIG. 13a) or particles with natural DNA of the same nucleic acid sequence (e.g., the nucleic acid agents only comprising natural nucleotides, FIG. 13b). For the target at a concentration of 100 nM, only the library comprising particles with modified nucleic acid agents (FIG. 13a) showed a strong binding signal, while the library comprising particles with only natural DNA nucleic acid agents did not show much binding signals (FIG. 13b), suggesting that modified nucleic acid agents may be used to generate agents with better binding activity.

Example 2 Particle Generation

Figure 2:
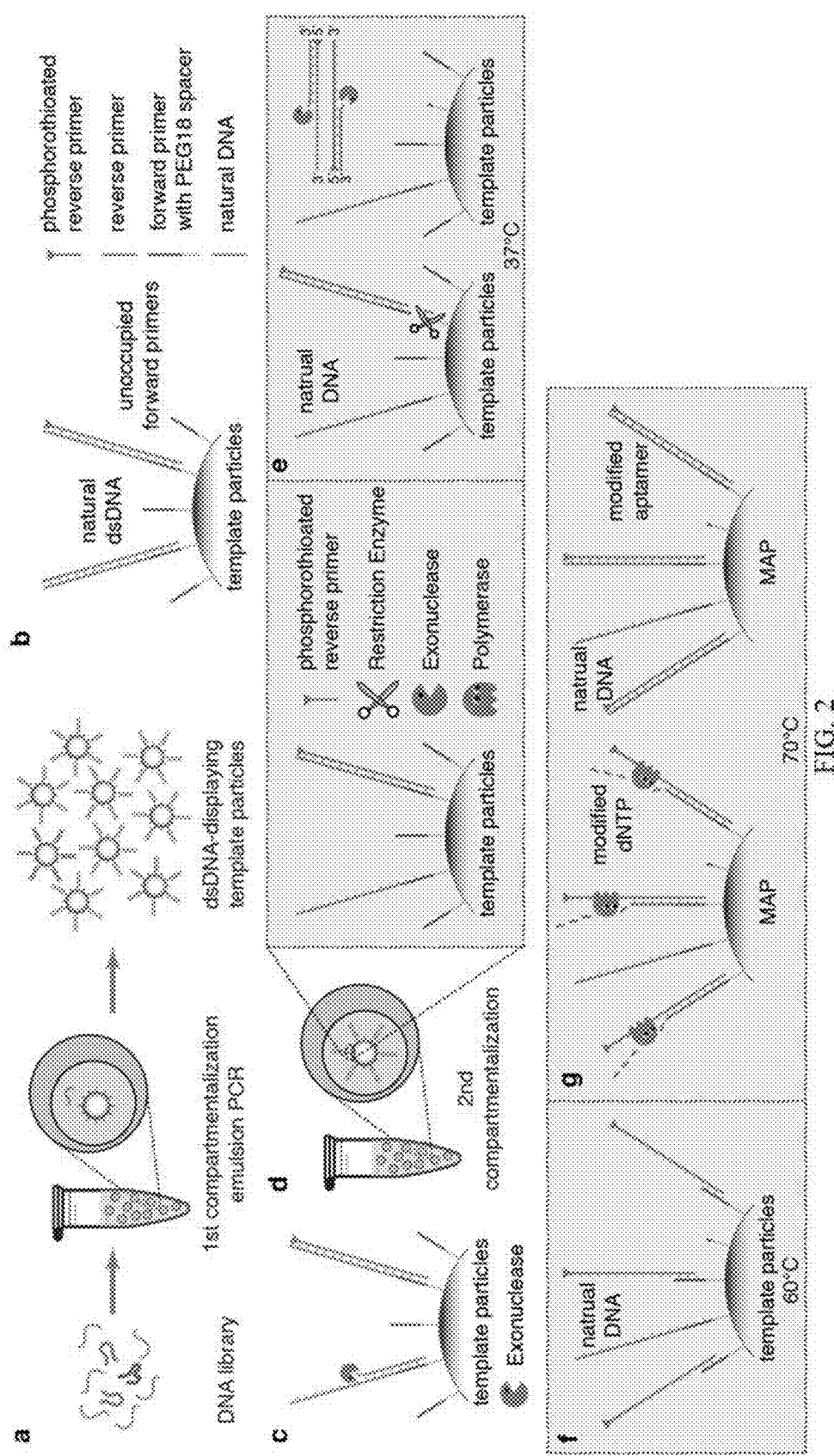
FIGS. 2a-2g illustrate another example of a process for generating a pool comprising a plurality of modified members according to the present disclosure.

FIGS. 2a-2g show another example for generating a particle according to the present disclosure. A library of of $3\times10^8$ random DNA was first transformed into a library of monoclonal template particles through a process of in vitro compartmentalization and emulsion PCR (ePCR) with particles displaying forward primers, performed similarly as described in Example 1 (FIG. 2a). The number of PCR cycles and reagent quantity (i.e. primers and polymerase) in each emulsion compartment were controlled so that about 50% of the forward primers displayed on the particle were utilized to synthesize the PCR products (FIG. 2a). In this way, there would be equal amount of DNA template strands (i.e., double-stranded nucleic acid agents of the first and the second double-stranded population) (50%) and available forward primers (i.e., single-stranded nucleic acid agents of a third population) (about 50%) for the extension reaction in the second stage compartmentalization.

Figure 14:
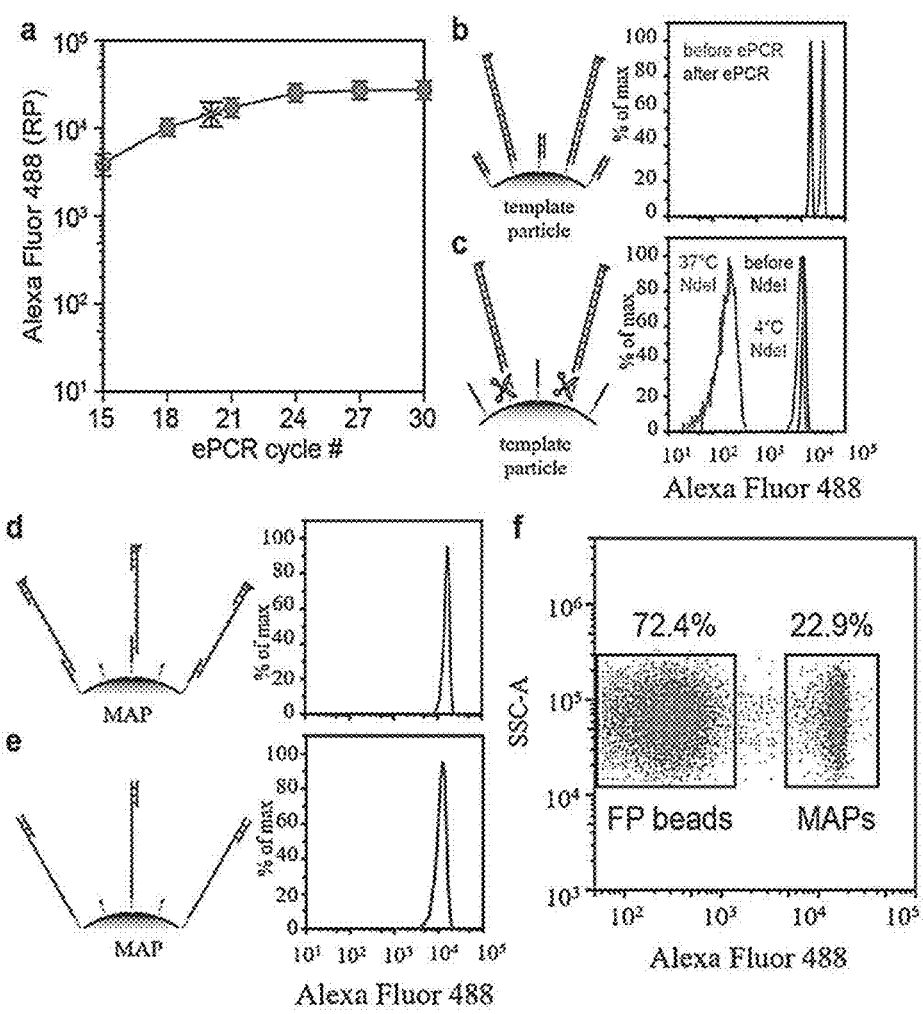
FIGS. 14a-14f illustrates the results of pool generation using a method according to the present disclosure.

In order to precisely control ePCR cycle number to achieve about 50% of maximum coverage on the template particles, a series of ePCR using different PCR cycle numbers were performed. After ePCR, the emulsion was broken and the reverse strand of all the nucleic acid agents immobilized to the particle was de-hybridized using NaOH. Then, the coverage of fully extended nucleic acid agents was quantified using FACS after annealing the AF-488 labeled reverse primers complementary to the 3'end of the fully extended nucleic acid forward strands to the particle generated. The median fluorescent intensity of the positive population after different cycles of ePCR was analyzed (as shown in FIG. 14a), and 20 ePCR-cycle was chosen to generate the DNA template particles so that about 50% of the available forward primers are occupied by PCR products (i.e., double-stranded candidate and identification nucleic acid agents). After this ePCR, about 50% of the forward primers of each DNA template particle were unoccupied and this was verified by simply annealing an AF-488 labeled strand that is complementary to the forward primer. This was done before and after ePCR and measured their fluorescence intensity using FACS, confirming about 50% ratio (13342/29365) (FIG. 14b).

The single-stranded DNA (ssDNA) library and primers were purchased from Integrated DNA Technologies (IDT). The library was synthesized with hand mixing method and PAGE-purified. Each 81-nucleotide (nt) library member featured a 40-nt randomized sequence flanked by 26-nt forward PCR primer and 20-nt reverse PCR primer (5'-CATATGAGCAGCACAGAGGTCAGATG-[40N]-CC-TATGCGTGCTACCGTGAA-3') (SEQ ID NO: 3). Both the forward primers and reverse primers used in this ePCR were specially designed. The forward primers contained a restriction enzyme cutting site at its 5' end, CATATG, that can be specifically recognized by restriction endonuclease NdeI (New England Biolabs, R0111) and cleaved at CA|TATG. The reverse primers were a 9:1 mixture of synthesized primers with (protected) and without (unprotected) nuclease-resistant phosphorothioated (PS) backbone respectively. The ratio of unprotected and protected reverse primers was controlled at 1 to 9 for ePCR so that about 10% of PCR products (i.e., nucleic acid agents of the second double-stranded population) displayed on the particle present unprotected reverse strands (FIG. 2b).

After breaking the emulsion and removing unreacted PCR reagents (same method as described in Example 1), the monoclonal template particles displayed dsDNA template (i.e., nucleic acid agents of the first and the second double-stranded population) on half of the primer sites. Accordingly, template particles displaying about 45% of the first double-stranded population (double-stranded candidate nucleic acid agents), about 5% of the second double-stranded population (double-stranded identification nucleic acid agents) and about 50% of the single-stranded third population (single-stranded forward primers) were obtained.

Next, the template particles were translated into modified particles, e.g., MAPs (or modified members).

The monoclonal template particles obtained were then mixed with 50 units of T7 5' to 3' exonuclease (New England Biolabs, M0263) in 100 µL of CutSmart® Buffer (New England Biolabs, B7204), and incubated 15 minutes at 25° C. The T7 exonuclease digested only the unprotected reverse strands (i.e., the reverse strand of nucleic acid agents in the second double-stranded population, about 5%) from the 5' end, and leaved the PS backbone protected reverse strands (i.e., reverse strand of the nucleic acid agents in the first double-stranded population, about 45%) intact (FIG. 2c). Then, $10^8$ template particles were mixed on ice a 100 µL reaction mixture consisted of CutSmart® Buffer (New England Biolabs, B7204), dATP, dGTP, dCTP or one of the modified dCTP derivatives, and dTTP of one of the modified dUTP derivatives (final concentration 50 µM for each of the natural dNTP and 100 µM for each of the modified dNTP derivatives), as well as three different enzymes (i.e., 80 units of NdeI restriction enzyme (New England Biolabs, R0111), 10 units of T7 5' to 3' exonuclease (New England Biolabs, M0263), and 40 units of KOD Xtreme™ Hot Start DNA Polymerase (EMD Millipore, 71975)). This reaction mixture was then separated into emulsion compartments in the second stage of in vitro compartmentalization (FIG. 2d) wherein each compartment comprises no more than one DNA template particle (same in vitro compartmentalization method as described in Example 1).

Next, the emulsion compartments were incubated at 37° C. for 60 minutes in a thermocycler (FIG. 2e). Here, the restriction enzyme released the DNA template (i.e., nucleic acid agents of the first double-stranded population) from the particles and the T7 exonuclease digested only the forward strand (i.e., the forward strand of nucleic acid agents in the first double-stranded population) from the 5' end that was now exposed after the release from the particle (FIG. 2e). The reverse strand (i.e., the reverse strand of nucleic acid agents in the first double-stranded population) was protected from the T7 exonuclease by the PS backbone. In this step, about 5% of template DNA was single-stranded (i.e., the forward strand of nucleic acid agents of the second double-stranded population) due to the previous T7 digestion, and would not be cut by the restriction enzyme (FIG. 2e). In this way, there would remain about 5% natural DNA template strands (i.e., the forward strand of nucleic acid agents of the second double-stranded population) on each modified particle (e.g., MAP) that can be directly amplified using PCR. The temperature was then raised to about 90° C. for 10 minutes to inactivate the NdeI restriction enzyme and activate the KOD Xtreme™ Hot Start DNA Polymerase. The temperature was then decreased to 60° C. for 30 seconds to allow the reverse strands (i.e., the reverse strand of nucleic acid agents in the first double-stranded population or the double-stranded candidate nucleic acid agents) to anneal to the available unoccupied single-stranded forward primers (i.e., partial complements, which are the single-stranded nucleic acid agents of the third population) on the particle (FIG. 2f). The temperature was then raised to 70° C. for 30 minutes to facilitate extension. KOD Xtreme™ Hot Start DNA Polymerase incorporates natural and modified dNTPs encoded by the template strand (i.e., the reverse strand of nucleic acid agents of the first double-stranded population) (FIG. 2g). Then, the emulsion was broken and the reverse strands were de-hybridized, leaving only the single strand modified aptamers (i.e., nucleic acid agents of the first single-stranded population) on the particles, completing the formation of modified particles (e.g., MAPs), which were then ready for screening. Like the template particles, modified particles (e.g., MAPs) are monoclonal wherein each particle displays about $10^5$ copies of a single modified aptamer (i.e., nucleic acid agents of the first single-stranded population) sequence and about $10^4$ copies of amplifiable natural DNA (i.e., nucleic acid agents of the second single-stranded population) sequences.

The conditions for each step in the second compartmentalization reaction were also carefully monitored and optimized. To test the NdeI restriction enzyme cutting step, the ePCR was done using AF-488 labeled reverse primers yielding fluorescent double-stranded DNA on the template particles (FIG. 14c). The NdeI activity was inhibited at low temperature, which is necessary to prevent double-stranded DNA from being released when preparing for the second compartmentalized reaction (FIG. 14c). Then, it was verified that cutting at 37° C. for 60 minutes using NdeI was able to release all double-stranded DNA template from the particles (FIG. 14c). Next, the T7 exonuclease activity was tested and the successful hybridization between PS-protected reverse strands (i.e., reverse strands of nucleic acid agents in the double-stranded population) and the unoccupied forward primers on the template particles were verified. This was done by breaking the emulsion and annealing the particles with AF-488 labeled reverse primer complement, and measuring fluorescence intensity in FACS (FIG. 14d). Their high fluorescence demonstrated that the T7 completely digested the forward strands and that the reverse strands are successfully captured by the available forward primer on the particles. Next, BST3.0 polymerase incorporated the natural and modified dNTPs in the reaction, successfully yielding the modified fully-extended nucleic acid agent (e.g., the aptamer), concluding the translation of template DNA particles into modified particles (e.g., MAPs). Then, the emulsion was broken and the reverse strands were removed using NaOH. The quality of the modified particles (e.g., MAPs) was tested using FACS by annealing the particles with fluorescently labeled reverse primers, such that only correctly-extended aptamers would yield signal (FIG. 14e). Based on the Poisson distribution, modified particles (e.g., MAPs) are highly monoclonal when <30% of the particles display modified aptamers, while the rest are unoccupied forward primer-particles. It was then able to consistently control the input ratios to yield an output of about 20% positive modified particles (e.g., MAPs or modified members), as confirmed by FACS (FIG. 14f).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for generating a pool comprising a plurality of modified members, the method comprising:
   a) providing a pool comprising a plurality of kernel members, with each kernel member comprising a plurality of partially double-stranded candidate nucleic acid agents immobilized to a solid support, and each of said partially double-stranded candidate nucleic acid agents comprising a forward strand and a reverse strand longer than said forward strand, wherein said forward and reverse strands associate with each other at least partially via base-paring;
   b) extending said forward strand of the partially double-stranded candidate nucleic acid agents by nucleotide polymerization using the corresponding reverse strand as a template, and at least one modified nucleotide is incorporated into said forward strand during extension to form modified candidate nucleic acid agents, thereby obtaining a pool of a plurality of modified members, with each modified member comprising a plurality of said modified candidate nucleic acid agents immobilized to said solid support;
   wherein for each modified candidate nucleic acid agent comprised by any modified member, a corresponding identification nucleic acid agent is comprised by the same modified member, wherein said identification nucleic acid agent enables amplification of its corresponding modified candidate nucleic acid agent, and
   a nucleic acid sequence of the candidate nucleic acid agents comprised by any kernel member is different from that of the candidate nucleic acid agents comprised by at least one other kernel member in the pool.

2. The method according to claim 1, wherein sequence diversity of the candidate nucleic acid agents comprised by any kernel member in the pool is less than that of the total candidate nucleic acid agents comprised by all the kernel members in the pool.

3. The method according to claim 1, wherein sequence diversity of the candidate nucleic acid agents comprised by any kernel member in the pool is from 1 to 1000.

4. The method according to claim 1, wherein said identification nucleic acid agent comprises the same nucleic acid sequence as that of its corresponding modified candidate nucleic acid agent.

5. The method according to claim 1, wherein said identification nucleic acid agent consists essentially of natural nucleotides.

6. The method according to claim 1, wherein said identification nucleic acid agent is also comprised by the kernel member employed to generate its corresponding modified candidate nucleic acid agent.

7. The method according to claim 1, wherein said modified candidate nucleic acid agent is capable of specifically binding to a protein target.

8. The method according to claim 7, wherein said modified candidate nucleic acid agent comprises an aptamer.

9. The method according to claim 1, wherein said modified candidate nucleic acid agent consists essentially of modified nucleotides.

10. The method according to claim 1, wherein said modified nucleotide comprises one or more modifications independently selected from the group consisting of a 2'-position sugar modification, a 2'-amino (2'-NH2) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution of 5-bromouracil, a substitution of 5-bromodeoxyuridine, a substitution of 5-bromodeoxycytidine, a backbone modification, a methylation, a 3' cap, and a 5' cap.

11. The method according to claim 1, wherein said providing a pool comprising a plurality of kernel members in a) comprises:
   a1) providing a pool comprising a plurality of template members, with each template member comprising a plurality of double-stranded candidate nucleic acid agents immobilized to the solid support, and each double-stranded candidate nucleic acid agent comprises a forward strand and a complementary reverse strand;
   a2) treating the plurality of template members of a1) to remove a substantial part of the forward strand of said double-stranded candidate nucleic acid agents, with the corresponding reverse strand immobilized on said solid support, forming said reverse strand of the partially double-stranded candidate nucleic acid agents of the kernel members.

12. The method according to claim 11, wherein sequence diversity of the double-stranded candidate nucleic acid agents comprised by any one of the template members in the pool is less than that of the total double-stranded candidate nucleic acid agents comprised by all the template members in the pool.

13. The method according to claim 11, wherein for each double-stranded candidate nucleic acid agent comprised by any template member, a corresponding double-stranded identification nucleic acid agent is comprised by the same template member, the double-stranded identification nucleic acid agent comprises a forward strand and a complementary reverse strand, and wherein said double-stranded identification nucleic acid agent is different from its corresponding double-stranded candidate nucleic acid agent while enabling amplification thereof.

14. The method according to claim 13, wherein said double-stranded identification nucleic acid agent comprises the same nucleic acid sequence as its corresponding double-stranded candidate nucleic acid agent.

15. The method according to claim 13, wherein a2) comprises:
   a2-1) treating the plurality of template members of a1) to remove only the reverse strand of the double-stranded identification nucleic acid agent, and the forward strand of the double-stranded identification nucleic acid agent remains immobilized on the solid support, forming the identification nucleic acid agent on the kernel member and/or the modified member.

16. The method according to claim 15, wherein a2) further comprises a2-2) treating the plurality of template members obtained in a2-1) so that a substantial part of the forward strand of the double-stranded candidate nucleic acid agents is removed, with the reverse strand of said double-stranded candidate nucleic acid agents immobilized on said solid support, forming said reverse strand of the partially double-stranded candidate nucleic acid agents of the kernel members.

17. The method according to claim 11, wherein the reverse strand of said double-stranded candidate nucleic acid agent is resistant to 5' to 3' exonuclease digestion.

18. The method according to claim 13, wherein the reverse strand of said double-stranded identification nucleic acid agent is susceptible to 5' to 3' exonuclease digestion.

19. The method according to claim 16, wherein a2-2) comprises treating the plurality of template members obtained in a2-1) with a site-specific nicking enzyme to generate nicked forward strand of the double-stranded candidate nucleic acid agents.

20. The method according to claim 16, wherein a2-2) comprises treating the plurality of template members obtained in a2-1) with a site-specific restriction enzyme to generate double-stranded break of the double-stranded candidate nucleic acid agents.

21. The method according to claim 11, wherein said template member further comprises a plurality of single-stranded forward primers immobilized on the solid support, said single-stranded forward primers are capable of associating with said reverse strand of the double-stranded candidate nucleic acid agent subsequent to removal of a substantial part of the forward strand of the double-stranded candidate nucleic acid agent.

* * * * *